(12) United States Patent
O'Donnell-Maloney et al.

(10) Patent No.: US 6,818,394 B1
(45) Date of Patent: Nov. 16, 2004

(54) HIGH DENSITY IMMOBILIZATION OF NUCLEIC ACIDS

(75) Inventors: Maryanne J. O'Donnell-Maloney, Boston, MA (US); Charles R. Cantor, Boston, MA (US); Hubert Köster, La Jolla, CA (US)

(73) Assignee: Sequenom, Inc., San Diego, CA (US)

( * ) Notice: Subject to any disclaimer, the term of this patent is extended or adjusted under 35 U.S.C. 154(b) by 88 days.

(21) Appl. No.: 09/297,575

(22) PCT Filed: Nov. 6, 1997

(86) PCT No.: PCT/US97/20195

§ 371 (c)(1),
(2), (4) Date: Jan. 4, 1999

(87) PCT Pub. No.: WO98/20020

PCT Pub. Date: May 14, 1998

Related U.S. Application Data

(63) Continuation-in-part of application No. 08/947,801, filed on Oct. 8, 1997, and a continuation-in-part of application No. 08/787,639, filed on Jan. 23, 1997, now Pat. No. 6,024,925, and a continuation-in-part of application No. 08/786,988, filed on Jan. 23, 1997, and a continuation-in-part of application No. 08/746,055, filed on Nov. 6, 1996, now abandoned.

(51) Int. Cl.[7] .............................................. C12Q 1/68
(52) U.S. Cl. ....................... 435/6; 435/89; 435/91.1; 435/174; 435/177; 436/501
(58) Field of Search ........................... 435/89, 6, 91.1, 435/174, 177; 436/501

(56) References Cited

U.S. PATENT DOCUMENTS

| | | | |
|---|---|---|---|
| 3,568,735 A | 3/1971 | Lancaster | 141/238 |
| 3,776,700 A | 12/1973 | Gallant | 422/65 |
| 3,807,235 A | 4/1974 | Lefkovitz | 73/863.32 |
| 3,999,689 A | 12/1976 | Ciantro | 222/108 |
| 4,139,346 A | 2/1979 | Rabbani | 422/56 |
| 4,214,159 A | 7/1980 | Hillenkamp et al. | 250/288 |
| 4,442,354 A | 4/1984 | Hurst et al. | 250/281 |
| 4,461,328 A | 7/1984 | Kenney | 422/100 |
| 4,548,245 A | 10/1985 | Crandell et al. | 141/237 |
| 4,554,839 A | 11/1985 | Hewett et al. | 73/864.16 |
| 4,582,789 A | 4/1986 | Sheldon, III et al. | 435/6 |
| 4,683,194 A | 7/1987 | Saiki et al. | 435/6 |
| 4,683,195 A | 7/1987 | Mullis et al. | 435/6 |
| 4,725,677 A | 2/1988 | Köster et al. | 536/27 |
| 4,729,947 A | 3/1988 | Middendorf et al. | 435/6 |
| 4,731,335 A | 3/1988 | Brigati | 436/180 |
| 4,740,692 A | 4/1988 | Yamamoto et al. | 250/282 |
| 4,749,742 A | 6/1988 | Elmore | 525/54.11 |
| 4,757,141 A | 7/1988 | Fung et al. | 536/27 |
| 4,778,993 A | 10/1988 | Waugh | 250/287 |
| 4,779,467 A | 10/1988 | Rainin et al. | 73/863.32 |
| 4,794,150 A | 12/1988 | Steel | 525/54.11 |
| 4,797,355 A | 1/1989 | Stabinsky | 435/6 |
| 4,798,706 A | 1/1989 | Brigati | 422/102 |
| 4,806,546 A | 2/1989 | Carrico et al. | 536/27 |
| 4,844,298 A | 7/1989 | Ohoka et al. | 222/58 |
| 4,855,225 A | 8/1989 | Fung et al. | 435/6 |
| 4,877,745 A | 10/1989 | Hayes et al. | 436/166 |
| 4,882,127 A | 11/1989 | Rosenthal et al. | 422/50 |
| 4,902,481 A | 2/1990 | Clark et al. | 422/101 |
| 4,920,264 A | 4/1990 | Becker | 250/282 |
| 4,925,629 A | 5/1990 | Schramm | 422/82.05 |
| 4,931,400 A | 6/1990 | Jitsukawa | 435/287 |
| 4,948,442 A | 8/1990 | Manns | 156/73.1 |
| 4,948,882 A | 8/1990 | Ruth | 536/27 |
| 4,952,518 A | 8/1990 | Johnson et al. | 436/518 |
| 4,983,521 A | 1/1991 | Lingappa et al. | 435/172.3 |
| 4,994,373 A | 2/1991 | Stavrianopoulos et al. | 435/6 |

(List continued on next page.)

FOREIGN PATENT DOCUMENTS

| | | |
|---|---|---|
| DE | 3221681 A1 | 12/1983 |
| DE | 3930312 | 4/1990 |
| DE | 4011991 | 10/1990 |

(List continued on next page.)

OTHER PUBLICATIONS

Lee, et al., Direct Measurement of the Forces Between Complemetary Strands of DNA, Science, vol. 266, Nov. 4, 1994, 771–773.

(List continued on next page.)

*Primary Examiner*—Bennett Celsa
(74) *Attorney, Agent, or Firm*—Stephanie L. Seidman; Heller Ehrman White & McAuliffe, LLP

(57) ABSTRACT

Processes and kits for immobilizing a high density of nucleic acids on an insoluble surface, which are particularly useful for mass spectrometric detection of nucleic acids, are disclosed. Arrays containing the immobilized nucleic acids and use of the immobilized nucleic acids in a variety of solid phase nucleic acid chemistry applications, including nucleic acid synthesis (chemical and enzymatic), hybridization and/or extension, and sequencing, are provided. Serial and parallel dispensing tools that can deliver defined volumes of fluid to generate multi-element arrays of sample material on a substrate surface are further provided. Tools provided herein can include an assembly of vesicle elements, or pins, wherein each of the pins can include a narrow interior chamber suitable for holding nanoliter volumes of fluid. Methods for dispensing tools that can be employed to generate multi-element arrays of sample material on a substrate surface are also provided. The tool can dispense a spot of fluid to a substrate surface by spraying the fluid from the pin, contacting the substrate surface or forming a drop that touches against the substrate surface. The tool can form an array of sample material by dispensing sample material in a series of steps, while moving the pin to different locations above the substrate surface to form the sample array, The prepared sample arrays may be passed to a plate assembly that disposes the sample arrays for analysis by mass spectrometry.

8 Claims, 20 Drawing Sheets

U.S. PATENT DOCUMENTS

| | | | |
|---|---|---|---|
| 5,000,921 A | 3/1991 | Hanaway et al. | 422/100 |
| 5,003,059 A | 3/1991 | Brennan | 536/27 |
| 5,023,187 A | 6/1991 | Koebler et al. | 436/180 |
| 5,037,882 A | 8/1991 | Steel | 525/54.11 |
| 5,045,694 A | 9/1991 | Beavis et al. | 250/287 |
| 5,047,215 A | 9/1991 | Manns | 422/101 |
| 5,062,935 A | 11/1991 | Schlag et al. | 204/157.41 |
| 5,064,754 A | 11/1991 | Mills | 435/6 |
| 5,077,210 A * | 12/1991 | Eigler et al. | 435/176 |
| 5,082,935 A | 1/1992 | Cruickshank | 536/27 |
| 5,108,703 A | 4/1992 | Pfost et al. | 422/65 |
| 5,118,605 A | 6/1992 | Urdea | 435/6 |
| 5,118,937 A | 6/1992 | Hillenkamp et al. | 250/282 |
| 5,135,870 A | 8/1992 | Williams et al. | 436/173 |
| 5,143,854 A | 9/1992 | Pirrung et al. | 436/518 |
| 5,149,625 A | 9/1992 | Church et al. | 435/6 |
| 5,171,989 A | 12/1992 | Williams et al. | 250/288 |
| 5,175,209 A | 12/1992 | Beattie et al. | 525/54.11 |
| 5,195,657 A | 3/1993 | Wells | 222/330 |
| 5,198,531 A | 3/1993 | Webber et al. | 525/332.2 |
| 5,202,561 A | 4/1993 | Giessmann et al. | 250/281 |
| 5,210,412 A | 5/1993 | Levis et al. | 250/288 |
| 5,221,518 A | 6/1993 | Mills | 422/62 |
| 5,234,824 A | 8/1993 | Mullis | 435/91 |
| 5,237,016 A | 8/1993 | Ghosh et al. | 525/329.4 |
| 5,242,974 A | 9/1993 | Holmes | 525/54.11 |
| 5,262,128 A | 11/1993 | Leighton et al. | 422/100 |
| 5,283,342 A | 2/1994 | Gustavson et al. | 548/304.1 |
| 5,288,644 A | 2/1994 | Beavis et al. | 436/94 |
| 5,312,233 A | 5/1994 | Tanny et al. | 417/316 |
| 5,338,688 A | 8/1994 | Deeg et al. | 436/180 |
| 5,350,676 A | 9/1994 | Oberhardt et al. | 435/13 |
| 5,373,156 A | 12/1994 | Franzen | 250/288 |
| 5,376,788 A | 12/1994 | Standing et al. | 250/287 |
| 5,380,833 A | 1/1995 | Urdea | 536/22.1 |
| 5,381,008 A | 1/1995 | Tanner et al. | 250/288 |
| 5,382,793 A | 1/1995 | Weinberger et al. | 250/288 |
| 5,399,501 A | 3/1995 | Pope et al. | 436/532 |
| 5,410,068 A | 4/1995 | Coull et al. | 548/545 |
| 5,430,136 A | 7/1995 | Urdea et al. | 536/243 |
| 5,436,327 A | 7/1995 | Southern et al. | 536/25.34 |
| 5,439,649 A | 8/1995 | Tseung et al. | 422/99 |
| 5,457,041 A | 10/1995 | Ginaven et al. | 435/172.1 |
| 5,474,895 A | 12/1995 | Ishii et al. | 435/6 |
| 5,478,893 A | 12/1995 | Ghosh et al. | 525/329.4 |
| 5,484,701 A | 1/1996 | Cocuzza et al. | 435/6 |
| 5,492,821 A | 2/1996 | Callstrom et al. | 435/188 |
| 5,498,545 A | 3/1996 | Vestal | 436/47 |
| 5,503,980 A | 4/1996 | Cantor | 435/6 |
| 5,506,348 A | 4/1996 | Pieles | 536/23.1 |
| 5,510,613 A | 4/1996 | Reilly et al. | 250/287 |
| 5,512,295 A | 4/1996 | Kornberg et al. | 424/450 |
| 5,512,439 A | 4/1996 | Hornes et al. | 435/6 |
| 5,514,548 A | 5/1996 | Krebber et al. | 435/6 |
| 5,527,675 A | 6/1996 | Coull et al. | 435/6 |
| 5,541,313 A | 7/1996 | Ruth | 536/24.3 |
| 5,545,539 A | 8/1996 | Miller | 435/91.2 |
| 5,547,835 A | 8/1996 | Koster | 435/6 |
| 5,552,535 A | 9/1996 | McLean et al. | 536/23.1 |
| 5,571,902 A | 11/1996 | Ravikumar et al. | 536/22.1 |
| 5,580,434 A | 12/1996 | Robotti et al. | 204/451 |
| 5,580,733 A | 12/1996 | Levis et al. | 435/6 |
| 5,583,042 A | 12/1996 | Roth | 435/288.1 |
| 5,589,136 A | 12/1996 | Northrup et al. | 422/102 |
| 5,599,500 A | 2/1997 | Jones | 422/62 |
| 5,601,982 A | 2/1997 | Sargent et al. | 435/6 |
| 5,605,662 A | 2/1997 | Heller | 422/68.1 |
| 5,605,798 A | 2/1997 | Köster | 435/6 |
| 5,609,907 A | 3/1997 | Natan | 427/2.12 |
| 5,612,474 A | 3/1997 | Patel | 536/27.14 |
| 5,616,698 A | 4/1997 | Krepinsky et al. | 536/18.6 |
| 5,616,700 A | 4/1997 | Reddy et al. | 536/25.3 |
| 5,622,824 A | 4/1997 | Köster | 435/6 |
| 5,624,711 A | 4/1997 | Sundberg et al. | 427/261 |
| 5,625,184 A | 4/1997 | Vestal et al. | 250/287 |
| 5,627,369 A | 5/1997 | Vestal et al. | 250/287 |
| 5,631,134 A | 5/1997 | Cantor | 435/6 |
| 5,635,598 A | 6/1997 | Lebl et al. | 530/334 |
| 5,639,633 A | 6/1997 | Callstrom et al. | 435/68.1 |
| 5,641,862 A | 6/1997 | Rutter et al. | 530/334 |
| 5,641,959 A | 6/1997 | Holle et al. | 250/287 |
| 5,643,722 A | 7/1997 | Rothschild et al. | 435/6 |
| 5,643,798 A | 7/1997 | Beavis et al. | 436/94 |
| 5,643,800 A | 7/1997 | Tarantino et al. | 436/518 |
| 5,648,462 A | 7/1997 | Funakoshi et al. | 530/344 |
| 5,648,480 A | 7/1997 | Letsinger et al. | 536/25.34 |
| 5,652,358 A | 7/1997 | Pfleiderer et al. | 536/25.3 |
| 5,654,545 A | 8/1997 | Holle et al. | 250/287 |
| 5,663,242 A | 9/1997 | Ghosh et al. | 525/329.4 |
| 5,668,266 A | 9/1997 | Ruth | 536/25.3 |
| 5,670,322 A | 9/1997 | Eggers et al. | 435/6 |
| 5,670,381 A | 9/1997 | Jou et al. | 436/518 |
| 5,677,195 A | 10/1997 | Winkler et al. | 436/518 |
| 5,679,773 A | 10/1997 | Holmes | 530/334 |
| 5,688,642 A * | 11/1997 | Chrisey et al. | 435/6 |
| 5,691,141 A | 11/1997 | Köster | 435/6 |
| 5,700,642 A | 12/1997 | Monforte et al. | 435/6 |
| 5,716,825 A | 2/1998 | Hancock et al. | 435/286.5 |
| 5,726,243 A | 3/1998 | Fields | 525/54.11 |
| 5,736,625 A | 4/1998 | Callstrom et al. | 530/402 |
| 5,736,626 A | 4/1998 | Mullah et al. | 536/25.3 |
| 5,742,049 A | 4/1998 | Holle et al. | 250/282 |
| 5,743,960 A | 4/1998 | Tisone | 118/683 |
| 5,746,373 A | 5/1998 | Sanada | 239/102.2 |
| 5,756,050 A | 5/1998 | Ershow et al. | 422/100 |
| 5,757,392 A | 5/1998 | Zhang | 347/14 |
| 5,760,393 A | 6/1998 | Vestal et al. | 250/282 |
| 5,770,860 A | 6/1998 | Franzen | 250/288 |
| 5,777,324 A | 7/1998 | Hillenkamp | 250/288 |
| 5,777,325 A | 7/1998 | Weinberger et al. | 250/287 |
| 5,795,714 A | 8/1998 | Cantor et al. | 435/6 |
| 5,807,522 A | 9/1998 | Brown et al. | 422/50 |
| 5,812,272 A | 9/1998 | King et al. | 356/445 |
| 5,828,063 A | 10/1998 | Koster et al. | 250/288 |
| 5,830,655 A | 11/1998 | Monforte et al. | 435/6 |
| 5,864,137 A | 1/1999 | Becker et al. | 250/287 |
| 5,869,240 A | 2/1999 | Patterson | 435/6 |
| 5,869,242 A | 2/1999 | Kamb | 435/6 |
| 5,872,010 A | 2/1999 | Karger et al. | 436/173 |
| 5,885,775 A | 3/1999 | Haff et al. | 435/6 |
| 5,894,063 A | 4/1999 | Hutchens et al. | 436/155 |
| 5,900,481 A | 5/1999 | Lough et al. | 536/55.3 |
| 5,925,520 A | 7/1999 | Tully et al. | 435/6 |
| 5,927,547 A | 7/1999 | Papen et al. | 222/57 |
| 5,969,350 A | 10/1999 | Kerley et al. | 250/287 |
| 5,981,185 A | 11/1999 | Matson et al. | 435/6 |
| 5,985,356 A | 11/1999 | Schultz et al. | 427/8 |
| 6,024,925 A | 2/2000 | Little et al. | 422/100 |
| 6,040,193 A | 3/2000 | Winkler et al. | 436/180 |
| 6,079,283 A | 6/2000 | Papen et al. | 73/864.11 |
| 6,083,762 A | 7/2000 | Papen et al. | 436/180 |
| 6,110,426 A | 8/2000 | Shalon et al. | 422/68.1 |
| 6,121,048 A | 9/2000 | Zaffaroni et al. | 436/45 |
| 6,136,269 A | 10/2000 | Winkler et al. | 422/61 |
| 6,268,131 B1 * | 7/2001 | Kang et al. | 435/6 |

FOREIGN PATENT DOCUMENTS

| | | | |
|---|---|---|---|
| DE | 9617011 | 4/1996 | H01J/49/10 |
| DE | 9618032 | 5/1996 | H01J/49/16 |
| DE | 9628178 | 7/1996 | H01J/49/00 |
| DE | 9754978 | 12/1997 | H01J/49/04 |

| | | |
|---|---|---|
| DE | 19731479 A1 | 8/1998 |
| EP | 0268237 B1 | 5/1988 |
| EP | 0339781 A2 | 11/1989 |
| EP | 0360677 A1 | 3/1990 |
| EP | 0396116 A2 | 11/1990 |
| EP | 0412883 A1 | 2/1991 |
| EP | 0455905 A2 | 11/1991 |
| EP | 0456304 A1 | 11/1991 |
| EP | 0500506 A1 | 8/1992 |
| EP | 0543550 A1 | 5/1993 |
| EP | 0684315 A1 | 11/1995 |
| EP | 0701001 A2 | 3/1996 |
| FR | 2597260 A1 | 10/1987 |
| GB | 2017105 | 3/1979 |
| GB | 2233654 A | 1/1991 |
| GB | 2312782 | 11/1997 ............ H01J/49/16 |
| GB | 2332273 | 6/1999 ............ H01J/49/04 |
| JP | 63230086 | 9/1988 |
| JP | 2215399 | 8/1990 |
| JP | 6294796 | 10/1994 |
| JP | 8290377 | 11/1996 |
| WO | 8402579 | 7/1984 |
| WO | 8805074 A1 | 7/1988 |
| WO | 8909282 | 10/1989 |
| WO | 8909406 | 10/1989 |
| WO | 8910786 | 11/1989 |
| WO | 8911270 | 11/1989 |
| WO | 8912624 | 12/1989 |
| WO | 8912694 | 12/1989 |
| WO | 9001564 | 2/1990 |
| WO | 9003382 | 4/1990 |
| WO | 9007582 | 7/1990 |
| WO | 9014148 | 11/1990 |
| WO | 9015883 | 12/1990 |
| WO | 9106678 | 5/1991 |
| WO | 9113075 | 9/1991 |
| WO | 9203575 | 3/1992 |
| WO | 9207879 | 5/1992 |
| WO | 9210092 | 6/1992 |
| WO | 9213629 | 8/1992 |
| WO | 9215712 | 9/1992 |
| WO | 9306925 | 4/1993 |
| WO | 9309668 | 5/1993 |
| WO | 9314108 A1 | 7/1993 |
| WO | 9320236 | 10/1993 |
| WO | 9403774 | 1/1994 |
| WO | 9403774 A1 | 2/1994 |
| WO | 9411529 | 5/1994 |
| WO | 9411530 | 5/1994 |
| WO | 9411735 | 5/1994 |
| WO | 9416101 | 7/1994 |
| WO | 9421822 | 9/1994 |
| WO | 9427719 | 12/1994 ............ B01J/19/00 |
| WO | 9504524 | 2/1995 |
| WO | 9507361 | 3/1995 |
| WO | 9511755 A1 | 5/1995 |
| WO | 9513538 | 5/1995 |
| WO | 9525116 | 9/1995 |
| WO | 9525175 | 9/1995 ............ C12Q/1/26 |
| WO | 9530773 | 11/1995 |
| WO | 9531429 | 11/1995 |
| WO | 9535505 A1 | 12/1995 |
| WO | 9602836 | 2/1996 |
| WO | 9637630 | 5/1996 |
| WO | 9619587 | 6/1996 |
| WO | 9629431 | 9/1996 |
| WO | 9632504 | 10/1996 |
| WO | 9636731 | 11/1996 |
| WO | 9636732 | 11/1996 |
| WO | 9636986 | 11/1996 |
| WO | 9636987 | 11/1996 |
| WO | 9708306 | 3/1997 |
| WO | 9716699 | 5/1997 |
| WO | 9733000 | 9/1997 |
| WO | 9737041 | 10/1997 |
| WO | 9742348 | 11/1997 |
| WO | 9743617 | 11/1997 |
| WO | 9803257 | 1/1998 |
| WO | 9805965 A1 | 2/1998 |
| WO | 9812355 | 3/1998 |
| WO | 9820019 | 5/1998 |
| WO | 9820020 | 5/1998 |
| WO | 9820166 | 5/1998 |
| WO | 9822541 A2 | 5/1998 |
| WO | 9826179 | 6/1998 |
| WO | 9834116 | 6/1998 |
| WO | 9834116 A1 | 8/1998 |
| WO | 9854751 | 12/1998 |
| WO | 9912040 | 3/1999 |

OTHER PUBLICATIONS

Vorm, et al, Improved Mass Accuracy in Matrix–Assisted Laser Desorption/Ionization Time–Of–Flight Mass Spectrometry of Peptides. Journal of The American Society For Mass Spectrometry, Nov., 1994, V5(N11): 955–958.

Certified English Language translation of the PCT Application filed under No. PCT/EP97/03571, published under No. WO 98/03257, provide by the Australian Patent Office, for application No. AU 3541997.

Debitsudo, A. "121:109581h Preparation of oligonucleotide monolayer," *Chemical Abstracts 121*: 1163:1163 (1994).

Debitsudo, A. "121:83891g Preparation of nucleotide thio–alkyl esters and monomolecular membrane," *Chemical Abstracts 121*: 1166 (1994).

Debitsudo, A. "122:291447q Organic super–thin fim of oligonucleotide derivative and method for its preparation," *Chemical Abstracts 122*: 1100 (1995).

Derwent No. 011716230, WPI Acc. No. 1998–133140/ 199813 for PCT Patent Application WO9805965 A1, "Identification of characteristics of eukaryotic cells –after covalent immobilisation on solid support,".

Derwent No. 011999582, WPI Acc. No. 1998–416492/ 199836 for PCT Patent Application WO9834116 A1, "Isolation and determination of analyte –by capture on specific binding particles and concentration of these on second, limited binding surface before detection, used e.g. for detecting RNA,".

Derwent No. 012012061, WPI Acc. No. 1998–428971/ 199837 for German Patent Application DE19731479 A, "Device for analysis of target chemicals has light emitting array—with chemical binder elements attached to array to capture target chemicals which change emitted light pattern accordingly,".

Emmett, M.R. and R.M. Caprioli. "Micro–Electrospray Mass Spectrometry: Ultra–High–Sensitivity Analysis of Peptides and Proteins," *J. Am. Soc. Mass Spectrometry 5*: 605–613 (1994).

Hofstadler et al. "Capillary Electrophoresis—Electrospray Ionization Fourier Transform Ion Cyclotron Resonance Mass Spectrometry for Direct Analysis of Cellular Proteins," *Anal. Chem. 67*: 1477–1480 (1995).

Jespersen et al. "Attomole Detection of Proteins by Matrix–assisted Laser Desorption/Ionization Mass Spectrometry with the Use of Picolitre Vials," *Rapid Communications in Mass Spectrometry 8(8)*: 581–584 (1994).

Li et al. "Analysis of Single Mammalain Cell Lysates by Mass Spectrometry," *J. Am. Chem. Soc. 118*: 11662–11663 (1996).

Lyttle, M.H. "126:235533k Versatile Linker Chemistry for Synthesis of 3'-Modified DNA," *Chemical Abstracts 126(18)*: 314 (1997).

Solouki et al. "Attomole Biomolecule Mass Analysis by MAtrix–Assisted Laser Desorption/Ionization Fourier Transform Ion Cyclotron Resonance," *Anal. Chem.* 67:4139–4144 (1995).

Wilm et al. "Electrospray and Taylor–Cone theory, Dole's beam of macromolecules at last," *International Journal of Mass Spectrometry and Ion Processes 136*: 167–180 (1994).

Valaskovic et al. "Attomole Protein Characterization by Capillary Electrophoresis– Mass Spectrometry," *Science 273*: 1199–1202 (1996).

Valaskovic et al. "Attomole–Sensitivity Electrospray Source for Large–Molecule Mass Spectrometry," *Anal. Chem. 67*: 3802–3805 (1995).

Wahl et al. "Use of small–diameter capillaries for increasing peptide and protein detection sensitivity in capillary electrophoresis–mass spectrometry," *Electrophoresis 14*: 448–457 (1993).

Zhang et al. "Micro–preparation Procedure for High–sensitivity Matrix–assisted Laser Desorption Ionization Mass Spectrometry," *Journal of Mass Spectrometry 30*: 1768–1771 (1995).

Asseline et al. "New Solid–Phase For Automated Synthesis of Oligonucleotides Containing An Amino–Alkyl Linker at Their 3'–End," *Tetrahedron Letters 31(1)*: 81–84 (1990).

Beattie et al. "123:112593k Synthesis and use of oligonucleotide libraries," *Chemical Abstracts 123*: 1172 (1995).

Bonfils, E. and N.T. Thuong. "Solid Phase Synthesis of 5', 3'–Bifunctional Oligodeoxyribonucleotides Bearing a Masked Thiol Group at the 3'–End," *Tetrahedron Letters 32(26)*: 3053–3056 (1991).

Day et al. "Immobilization of polynucleotides on magnetic particles," *Biochem. J. 278*: 735–740 (1991).

Beattie et al., "Synthesis and use of oligonucleotide libraries", *Chem. Abst., 123*:1172 (1995).

Debitaudo, A., "Organic super–thin film of oligonucleotide derivative and method for its preparation", *Chem. Abst., 122*:1100 (1995).

Certified English Language Translation of PCT Application 98/03257 (Item L).

Lyttle et al., "Versatile Linker Chemistry for Synthesis of 3'–Modified DNA", *Chem. Abst., 128*(18):314 (1997).

Pon et al., "Derivatization of Controlled Pore Glass Beads for Solid Phase Oligonucleotide Synthesis", *BioTechnique, 6*(8):768–770, 773–775 (1988).

Agrawal et al., Efficient methods for attaching non–radioactive labels to the 5' ends of synthetic oligodeoxyribonucleotides, *Nucleic Acids Res. 14*:6227–6245 (1986).

Alderton et al., Magnetic bead purification of M13 DNA sequencing templates, *Anal. Biochem. 201*:166–169 (1992).

Allin, S.M. and Shuttleworth, S.J., "The Preparation and First Application of a Polymer–Supported "Evans" Oxazolidinone", *Tetrahedron Lett., 37*(44):8023–8026 (1996).

Andersen, et al., Electrospray ionization and matrix assisted laser desorption/ionization mass spectrometry: Powerful analytical tools in recombinant protein chemistry. *Nature Biotech. 14*:449–457 (1996).

Ardey, Electrospray mass spectrometry, *Spectroscopy Europe, 4*:10–20 (1992).

Arlinghaus et al., Applications of resonance ionization spectroscopy for semiconductor, environmental and biomedical analysis, and for DNA sequencing, *SPIE*, vol. 1435, *Opt. Methods Ultrasensitive Detect. Anal. Tech. Appl.* pp. 26–35 (1991).

Arshady, Reza, Beaded polymer supports and gels: I. Manufacturing techniques, *Journal of Chromatography*, 586:181–197 (1991).

Arshady, Reza, Beaded polymer supports and gels: II. Physico–chemical criteria and functionalization, *Journal of Chromatography*, 586:199–219 (1991).

Backes, B.J. et al., "Activation Method to Prepare a Highly Reactive Acylsulfonamide "Safety Catch" Linker for Solid– Phase Synthesis[1]", *J. Am. Chem. Soc.*, 118:3055–3056 (1996).

Bains, DNA sequencing by mass spectrometry: Outline of a potential future application, *Chimicaoggi 9*:13–16 (1991).

Bains, Setting a sequence to sequence a sequence, *Biotechnology 10*:757–758 (1992).

Bannwarth, Solid–phase synthesis of oligodeoxynucleotides containing phosphoramidate internucleotide linkages and their specific chemical cleavage, *Helvetica Chimica Acta 71*:1517–1527 (1988).

Barrell, DNA sequencing: present limitations and prospects for the future, *FASEB J. 5*: 40–45 (1991).

Batista–Viera et al., A new method for reversible immobilization of thiol biomolecules bsed on solid–phase bound thiolsulfonate groups, *App. Biochem and Biotech*, 31:175–195 (1991).

Beaucage et al., The synthesis of modified oligonucleotides by the phosphoramidite approach and their applications, *Tetrahedron 49*:6123–6194 (1993).

Beck and Köster, Applications of dioxetane chemiluminescent probes to molecular biology, *Anal. Chem.* 62:2258–2270 (1990).

Beck et al., Chemiluminescent detection of DNA: application of DNA sequencing and hybridization, *Nucleic Acids Res. 17*(13):5115–5123 (1989).

Berkenkamp et al., Infrared MALDI mass spectrometry of large nucleic acids, *Science 281*:260–2 (1998).

Bishop and Waldholz, *Genome: The story of the most astonishing scientific adventure of our time—The attempt to map all the genes in the human body*, Simon & Schuster, New York (1991).

Braun et al., "Improved Analysis of Microsatellites Using Mass Spectrometry", *Genomics 46*:18–23 (1997).

Braun et al., Detecting *CFTR* gene mutations by using primer oligo base extension and mass spectrometry, *Clinical Chemistry 43*:1151–1158 (1997).

Bray, A.M. et al., "Direct Cleavage of Peptides from a Solid Support into Aqueous Buffer. Application in Simultaneous Multiple Peptide Synthesis", *J. Org. Chem.*, 56:6659–6666 (1991).

Brennan et al., New methods to sequence DNA by mass spectrometry, *SPIE*, vol. 1206, *New Technol. Cytom. Mol. Biol.* pp. 60–77 (1990).

Broude et al., Enhanced DNA sequencing by hybridization, *Proc. Natl. Acad. Sci. 91*:3072–3076 (1994).

Brown et al., A single–bead decode strategy using electrospray ionization mass spectrometry and a new photolabile linker: 3–Amino–3–(2–nitrophenyl)propionic acid, *Molec. Diversity 1*:4–12 (1995).

Burgess, K. et al., "An Approach to Photolabile, Fluorescent Protecting Groups", *J. Org. Chem.*, 62:5165–5168 (1997).

Caldwell et al., Mid–infrared matrix assisted laser desorption ionization with a water/glycerol matrix, *Applied Surface Science* 127–129:242–247 (1998).

Cantor CR, How will the Human Genome Project improve our quality of life? *Nat Biotechnol.* 16(3):212–3 (1998).

Cantor CR et al., Instrumentation in molecular biomedical diagnostics: an overview, *Genet Anal.* 14(2):31–6 (1997).

Cantor CR et al., Massive attck on high–throughput biology, *Nat Genet.* 20(1):5–6 (1998).

Chen and Seeburg, Supercoil sequencing: A fast and simple method for sequencing plasmid DNA, *DNA* 4(2):165–170 (1985).

Chorush RA et al., Surface–induced dissociation of multiply–protonated proteins, *Anal Chem.* 67(6):1042–6 (1995).

Chrisey et al., Covalent attachment of synthetic DNA to self–assembled monlayer films, *Nucl. Acids Res.* 24:3031–3039 (1996).

Chrisey et al., Fabrication of patterned DNA surfaces, *Nucl. Acids. Res.* 24:3040–3047 (1996).

Church et al., "Multiplex DNA Sequencing", *Science* 240:185–188 (1988).

Covey et al., The determination of protein, oligonucleotide and peptide molecular weights by ionspray mass spectrometry, *Rapid Communications in Mass Spectrometry* 2(11):249–256 (1988).

Crain, "Mass spectrometric techniques in nucleic acid research", *Mass Spectr. Rev.* 9:505–554 (1990).

Damha, Masad J. et al.; An Improved Procedure for Derivatization of Controlled–Pore Glass Beads for Solid–Phase Oligonucleotide Synthesis; Nucleic Acids Research vol. 18, No. 13 (1990); pp. 3813–3821.

Database WPI, Derwent Publications #199703, citing Japanese Patent No. 8290377 published Nov. 5, 1996.

Database WPI, Derwent Publications #198942, citing International PCT Application No. WO 89/09406 published Oct. 5, 1989.

Database WPI, Derwent Publications #199830, citing International PCT Application No. WO 98/26179 published Jun. 18, 1998.

Database WPI, Derwent Publications #199018, citing German Patent No. DE 3930312 published Apr. 26, 1990.

Database WPI, Derwent Publications #199015, citing European Patent No. EP 0360677 published Mar. 28, 1990.

Database WPI, Derwent Publications #199043, citing German Patent No. DE 4011991 published Oct. 18, 1990.

Database WPI, Derwent Publications #198844, citing Japanese Patent No. JP 63230086 published Sep. 26, 1988.

Database WPI, Derwent Publications #199040, citing Japanese Patent No. JP 2215399 published Aug. 28, 1990.

Database WPI, Derwent Publications #199516, citing Wo 9507361 A, Detecting presence and position of mutation(s) in double stranded DNA—by amplification, labelling strands with different markers, hybridisation and detecting heteroduplex by cleavage of unpaired strands.

DeGrado, W.F. and Kaiser, E.T., "Polymer–Bound Oximie Esters as Supports for Solid–Phase Peptide Synthesis. Preparation of Protected Peptide Fragments", *J. Org. Chem.*, 45:1295–1300 (1980).

Drmanac, et al., Sequencing of megabase plus DNA by hybridization: Theory of the method, *Genomics* 4:114–128 (1989).

Eckstein and Goody, Synthesis and properties of diastereoisomers of adenosine 5'–(O–1–thiotriphosphate) and adenosine 5'–(O–2–thiotriphosphate), *Biochemistry* 15(8):1685–1691 (1976).

Eckstein, F., Phosphorothioate analogues of nucleotides, *Accounts Chem. Res.* 12:204–210 (1979).

Eckstein, Nucleoside phosphorothioates, *Ann. Rev. Biochem.* 54:367–402 (1985).

Edmonds et al., Thermospray liquid chromatography–mass spectrometry of nucleosides and of enzymatic hydrolysates of nucleic acids, *Nucleic Acids Research* 13:8197–8206 (1985).

Eggers et al., A microchip for quantitative detection of molecules utilizing luminescent and radioisotope reporter groups, *BioTechniques* 17:516–524 (1994).

Ehring et al., Photochemical versus thermal mechanisms in matrix–assisted laser desorption/ionization probed by back side desorption, *Rapid Comm in Mass Spect* 10:821–824 (1996).

Eperon, I. C., Rapid preparation of bacteriophage DNA for sequence analysis in sets of 96 clones, using filtration, *Anal. Biochem* 156:406–412 (1986).

Fattom et al., *Infection & Immun.* 60:584–589 (1992).

Foster, *Organic Charge Transfer Complexes*, Academic Press (1969).

Frank and Köster, DNA chain length and the influence of base composition on electrophoretic mobility of oligodeoxyribonucleotides in polyacrylamide–gels, *Nucl. Acids Res.* 6:2069–2087 (1979).

Fu et al., Sequencing double–stranded DNA by strand displacement, *Nucl Acids Res* 25:677–679 (1997).

Fu et al., Sequencing exons 5 to 8 of the p53 gene by MALDI–TOF mass spectrometry, *Nat Biotechnol* 16:381–4 (1998).

Fu et al., A DNA sequencing strategy which requires only five bases of known terminal sequence for priming, Paper presented, Genome Mapping and Sequencing, Cold Spring Harbor Laboratory.

Fu et al., Efficient preparation of short DNA sequence ladders potentially suitable for MALDI–TOF DNA sequencing, *Genetic Analysis* 12:137–142 (1996).

Fu et al., "A DNA sequencing strategy that requires only five bases of known terminal sequencing for priming", *Proc. Natl. Acad. Sci.* 92:10162–10166 (1995).

Fujita et al., Surprising lability of biotin–streptavidin bond during transcription of biotinylated DNA bound to paramagnetic beads, *BioTechniques* 14:608–617 (1993).

Gait, M.J., ed., "*Oligonucleotide Synthesis : A Practical Approach*", IRL Practical Approach Series, IRL Press, Oxford, 1984.

Ganem et al., Detection of oligonucleotide duplex forms by ion–spray mass spectrometry, *Tetrahedron Letters* 34(9):1445–1448, (1993).

Gayo, L.M. and Suto, M.J., "Traceless Linker: Oxidative Activation and Displacement of a Sulfur–Based Linker", *Tetrahedron Lett.*, 38(2):211–214 (1997).

Ghosh and Musso, Covalent attachment to solid supports, *Nucl. Acids Res.* 15:5353–5372 (1987).

Gildea et al., A versatile acid–labile linker for modification of synthetic biomolecules, *Tetrahedron Letters* 31:7095–7398 (1990).

Goldmacher et al., Photoactivation of toxin conjugates, *Bioconjugate Chem.* 3:104–107, (1992).

Graber JH et al., Advances in DNA diagnostics, *Curr Opin Biotechnol.* 9(1):14–8 (1998).

Graber JH et al., Differential sequencing with mass spectrometry, *Genet Anal.* 14(5–6):215–9 (1999).

Greene, *Protective Groups in Organic Synthesis*, 2nd Edition, Wiley & Sons (1991).

Gross et al., Investigations of the metastable decay of DNA under ultraviolet matrix–assisted laser desorption/ionization conditions with post–source–decay analysis and hydrogen/deuterium exchange, *J Amer Soc for Mass Spect* 9:866–878 (1998).

Gruić–Sovulj I. et al., Matrix–assisted laser desorption/ionisation mass spectrometry of transfer ribonucleic acids isolated from yeast, *Nucleic Acids Res.* 25(9):1859–61 (1997).

Haglund et al., Marix–assisted laser–desorption mass spectrometry of DNA using an infrared free–electron laser, *SPIE* 1854:117–128.

Han, Y. et al., "Silicon Directed *ipso*–Substitution of Polymer Bound Arylsilanes: Preparation of Biaryls *via* the Suzuki Cross–Coupling Reaction", *Tetrahedron Lett.*, 37(16):2703–2706 (1996).

Hayashi et al., Immobilization of thiol proteases onto porous poly(vinyl alcohol) beads, *Polymer Journal*, 25:5, 489–497 (1993).

Hazum et al., A photocleavable protecting group for the thiol function of cysteine, *Pept., Proc. Eur. Pept. Symp., 16th*, Brunfeldt, K (Ed), pp. 105–110 (1981).

Hermanson, *Bioconjugate Techniques*, Academic Press (1996).

Higgins GS et al., Competitive oligonucleotide single–base extension combined with mass spectrometric detection for mutation screening, *Biotechniques* 23(4):710–4 (1997).

Higuchi et al., A general method of in vitro preparation and mutagenesis of DNA fragments: Study of protein and DNA interactions, *Nucleic Acids Res.* 16:7351–7367 (1988).

Higuchi et al., Kinetic PCR analysis: Real–time monitoring of DNA amplification reactions, *Bio/Technology* 11:1026–1030 (1993).

Hillenkamp and Ehring, Laser desorption mass spectrometry Part 1: Basic mechanisms and techniques, *Mass Spectrometry in the Biological Sciences: A tutorial*, pp. 165–179 (1992).

Hillenkamp et al., "Matrix Assisted UV–Laser Desorption/ionization: A New Approach to Mass Spectrometry of Large Biomolecules", *Bio Mass Spectr.*, Burlingame and McCloskey (eds.), pp. 49–61, Elsevier Science Publishers B.V., Amsterdman (1989).

Hobbs and Eckstein, A general method for the synthesis of 2'–azido–2'deoxy–and 2'–amino–2'–deoxyribofuranoxyl purines, *J. Org. Chem.* 42:714–719 (1976).

Hornes and Korsnes, Magnetic DNA hybridization of oligonucleotide probes attached to superparamagnetic beads and their use in the isolation of Poly(A) mRNA from eukaryotic cells, *GATA* 7:145–150, (1990).

Hsiung et al., A new simpler photoaffinity analogue of peptidyl rRNA, *Nucl Acids Res* 1:1753–1762 (1974).

Hultman et al., Direct solid phase sequencing of genomic and plasmid DNA using magnetic beads as solid support, *Nucl. Acids Res.* 17:4937–4946 (1989).

Huth–Fehre et al., Matrix–assisted laser desorption mass spectrometry of oligodeoxythymidulic acids, *Rapid Communications in Mass Spectrometry* 6(3):209–213 (1992).

Hyman, A new method of sequencing DNA, *Anal. Biochem.* 174:423–436 (1988).

Innis et al., DNA sequencing with *Thermus aquaticus* DNA polymerase and direct sequencing of polymerase chain reaction–amplified DNA, *Proc. Natl. Acad. Sci. USA* 85:9436–9440 (1988).

Innis et al., editors, *PCR Protocols: A guide to methods and applications*, Academic Press, San Diego (1990).

Jacobson, et al. Applications of mass spectrometry to DNA sequencing, *GATA* 8:223–229 (1991).

Jett et al., "High–Speed DNA Sequencing: An Approach Based Upon fluorescence Detection of Single Molecules", *J. Bio Strut & Dynam.* 7(2):301–09 (1989).

Ji et al., Two–dimensional electrophoretic analysis of proteins expressed by normal and cancerous human crypts: Application of mass spectrometry to peptide–mass fingerprinting, *Electrophoresis* 15:391–405 (1994).

Juhasz et al., Applications of delayed extraction matrix–assisted laser desorption ionization time–of–flight mass spectrometry to oligonucleotide analysis, *Analy Chem* 68:941–946 (1996).

Jurinke et al., Analysis of ligase chain reaction products via matrix–assisted laser desorption/ionization time–of–flight–mass spectrometry, *Anal Biochem* 237:174–181 (1996).

Jurinke et al., Detection of hepatitis B virus DNA in serum samples via nested PCR and MALDI–TOF mass spectrometry, *Genetic Analysis* 13:67–71 (1996).

Jurinke et al., Application of nested PCR and mass spectrometry for DNA–based virus detection: HBV–DNA detected in the majority of isolated anti–HBc positive sera, *Genetic Analysis* 14:97–102 (1998).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Kaldor, S.W. et al., "Use of Solid Supported Nucleophiles and Electrophiles for the Purification of Non–Peptide Small Molecule Libraries", *Tetrahedron Lett.*, 37(40):7193–7196 (1996).

Khrapko et al., An oligonucleotide hybridization approach to DNA sequencing, *FEB* 256(1,2):118–122 (1989).

Khrapko et al., "A method for DNA sequencing by hybridization with oligonucleotide matrix", *J. DNA Sequencing and Mapping* 1:375–388 (1991).

Kirpekar et al., DNA sequence analysis by MALDI mass spectrometry, *Nucleic Acids Res.* 26:2554–9 (1998).

Kirpekar et al., "7–deaza purine bases offer a higher ion stability in the analysis of DNA by matrix–assisted laser desorption/ionization mass spectrometry" *Rapid Commun. Mass Spectrom.* 9:525–531 (1995).

Köster et al., "A strategy for rapid and efficient DNA sequencing by mass spectrometry", *Nature Bio* 14:1123–1128 (1996).

Köster et al. Oligonucleotide synthesis and multiplex DNA sequencing using chemiluminescent detection, *Nucl. Acids Res., Symposium Series No.* 24:318–321, (1991).

Köster et al., N–acyl protecting groups for deoxynucleotides: A quantitative and comparative study, *Tetrahedron* 37:363–369 (1981).

Köster et al., Some improvements in the synthesis of DNA of biological interest, *Nucl Acids Res* 7:39–59 (1980).

Köster et al., Well–defined insoluble primers for the enzymatic synthesis of oligo– and polynucleotides, *Hoppe Seylers Z. Physiol. Chem.* 359(11):1579–1589 (1978).

Köster et al., Polymer support oligonucleotide synthesis—XV[1,2], *Tetrahedron* 40:102–112 (1984).

Kozal et al., "Extensive polymorphisms observed in HIV–1 clade B protease gene using high–density oligonucleotide arrays", *Nature Medicine* 2(7):753–759 (1996).

Kumar, G. and Poonian, M.S., "Improvements in Oligodeoxyribonucleotide Synthesis: Methyl N,N–Dialkylphosphoramidite Dimer Units for Solid Support Phosphite Methodology", *J. Org. Chem.*, 49:4905–4912 (1984).

Kussmann, et al., Matrix–assisted laser desorption/ionization mass spectrometry sample preparation techniques designed for various peptide and protein analytes, *J. Mass Spec.* 32:593–601 (1997).

Labeit et al., Laboratory methods: A new method of DNA sequencing using deoxynucleoside α–thiotriphophates, *DNA* 5:173–177 (1986).

Lamture et al., Direct detection of nucleic acid hybridization on the surface of a charge coupled device, *Nucl. Acids Res.* 22:2121–2125 (1994).

Landegren et al., "DNA Diagnostics—Molecular techniques and automation", *Science* 242:229–237 (1988).

Lawrance et al., Megabase–scale mapping of the HLA gene complex by pulsed field gel electrophoresis, *Science* 235:1387–1389 (1987).

Leznoff, C.C. and Wong, J.Y., "The Use of Polymer Supports in Organic Synthesis. The Synthesis of Monotrityl Ethers of Symmetrical Diols", *Can. J. Chem.*, 50:2892–2893 (1972).

Li et al., "Analysis of single mammalian cell lysates by mass spectrometry", *J. Am. Chem. Soc.* 118:11662–11663 (1996).

Li et al., "High–Resolution MALDI Fourier Transform Mass Spectrometry of Oligonucleotides", *Anal Chem* 68(13):2090–2096 (1996).

Little et al., "Direct detection of synthetic and biologically generated double–stranded DNA by MALDI–TOF MS", *J. Mass Spec* 17:1–8 (1997).

Little et al., Verification of 50– to 100–mer DNA and RNA sequences with high–resolution mass spectrometry, *Proc. Natl. Acad. Sci. USA* 92:2318–2322 (1995).

Little et al., Identification of apolipoprotein E polymorphisms using temperature cycled primer oligo base extension and mass spectrometry, *Short Communication, Eur J Clin Chem Clin Biochem* 35(7):545–8 (1997).

Little et al., "Mass spectrometry from miniaturized arrays for full comparative DNA analysis", *Nature Med* 3(12):1413–1416 (1997).

Little et al., Detection of RET proto–oncogene codon 634 mutations using mass spectrometry, *J. Mol Med.* 75:745–750 (1997).

Little et al., "MALDI on a Chip: Analysis of Arrays of Low–Femtomole to Subfemtomole Quantities of Synthetic Oligonucleotides and DNA Diagnostic Products Dispensed by a Piezoelectric Pipet", *Anal chem* 69:4540–4546 (1997).

Lloyd–Williams, P. et al., "Convergent Solid–Phase Peptide Synthesis", *Tetrahedron*, 49(48):11065–11133 (1993).

Lorsbach, B.A. et al., "Reissert–Based "Traceless" Solid–Phase Synthesis: Isoquinoline, and Isoxazoline–Containing Heterocycles", *J. Org. Chem.*, 61:8716–8717 (1996).

Lund et al., Assessment of methods for covalent binding of nucleic acids to magnetic beads, Dynabeads™ and the characteristics of the bound nucleic acids in hybridization reactions, *Nucl. Acids Res.* 16:10861–10880 (1988).

Manoharan et al., A 2'–O–thiol tether in the ribose moiety of nucleic acids for conjugation chemistry, *Gene*, 149:147–156 (1994).

Marshall and Hodgson, "DNA chips: An array of possibilities", *Nature Biotechnology* 16:27–31 (1998).

Martin, "New technologies for large–genome sequencing", *Genome* 31:1073–1080 (1989).

Matteucci et al., Synthesis of deoxyoligonucleotides on a polymer support, *J. A. Chem. Soc. 103*:3185–3195, 1981.

Maxam and Gilbert, Sequencing end–labeled DNA with base–specific chemical cleavages, *Methods in Enzymology* 65:499–560 (1980).

McCray and Trentham, "Properties and uses of photoreactive caged compounds", *Annu. Rev. Biophys. Biophys. Chem.* 18:239–270 (1989).

Miyazaki, et al., The first Japanese case of Hb Santa Ana, an unstable abnormal hemoglobin, identified rapidly by electrospray ionization mass spectrometry. *Internal Medicine* 36:365–370 (1997).

Moini et al., "A Moving Belt Device to Couple High–Performance Liquid Chromatography and Chemical Reaction Interface Mass Spectrometry", *Bio Mass Spect* 20:308–312 (1991).

*Molecular Cloning: A laboratory manual*, 2nd, ed., Ch. 11: Synthetic oligonucleotide probes, Sambrook, Cold Spring Harbor Laboratory Press New York, pp. 11.1–11.61 (1989).

Monforte and Becker, High–throughput DNA analysis by time–of–flight mass spectrometry, *Nature Medicine* 3:360–362 (1997).

Morphy, J.R. et al., "A Novel Linker Strategy for Solid–Phase Synthesis", *Tetrahedron Lett.*, 37(18):3209–3212 (1996).

Mosca et al., Mass spectrometry and DNA analysis, *Hemoglobin* 17(3):261–268 (1993).

Murray, "DNA sequencing by mass spectrometry", *J. Mass. Spect.* 31:1203–1215 (1996).

Nakamaye et al., "Direct sequencing of polymerase chain reaction amplified DNA fragments through the incorporation of deoxymucleoside α–thiotriphosphates", *Nucleic Acids Res.* 16(21):9947–9959 (1988).

Nelson et al., "Volatilization of High Molecular Weight DNA by Pulsed Laser Ablation of Frozen Aqueous Solutions", *Science* 246:1585–1587 (1989).

Nelson et al., Time–of–flight mass spectrometry of nucleic acids by laser ablation and ionization from a frozen aqueous matrix, *Rapid Communications in Mass Spectrometry* 4:348–351 (1990).

Newlander, K.A. et al., "Simple Silyl Linker for the Solid Phase Organic Synthesis of Aryl–Containing Molecules", *J. Org. Chem.*, 62:6726–6732 (1997).

Newton et al., The production of PCR products with 5' single–stranded tails using primers that incorporate novel phosphoramidite intermediates, *Nucl. Acids. Res.* 21:1155–1162 (1993).

Nikiforov and Rogers, The use of 96–well polystyrene plates for DNA hybridization–based assays: An evaluation of different approaches to oligonucleotide immobilization, *Anal. Biochem.* 227:201–209 (1995).

Nordhoff et al., "Ion stability of nucleic acids in infrared matrix–assisted laser desorption/ionization mass spectrometry", *Nuc Acids Res.* 21(15):3347–3357 (1993).

Nordoff et al., "Matrix–assisted laser desorption/ionization mass spectrometry of nucleic acids with wavelength in the ultraviolet and infrared", *Rapid Comm. Mass Spectrom.* 6:771–776 (1992).

Norton, J.C. et al., "Targeting Peptide Nucleic Acid–Protein Conjugates to Structural Features within Duplex DNA", *Bioorg. Med. Chem.*, 3(4):437–445 (1995).

O'Connor PB et al., Isotopic assignment in large–molcule mass spectra by fragmentation of a selected isotopic peak, *Anal Chem.* 68(3):542–5 (1996).

O'Donnell et al., "High–Density, Covalent Attachment of DNA to Siliocn Wafers for Analysis by MALDI–TOF Mass Spectrometry", *Analytical Chemistry* 69(13):2438–2443 (1997).

O'Donnell et al., "MassArray as an Enabling Technology for the Industrial–Scale Analysis of DNA", *Genetic Engineering News* 17(21) (1997).

O'Donnell–Maloney et al., "Microfabrication and array technologies for DNA sequencing and diagnostics", *Genetic Analysis: Biomolecular Engineering* 13:151–157 (1996).

O'Donnell–Maloney et al., "The development of microfabricated arrays for DNA sequencing and analysis" *TIBTECH* 14:401–407 (1996).

Olejnik et al, Photocleavable biotin phosphoramidite for 5'–end–labeling, affinity purification and phosphorylation of synthetic oligonucleotides, *Nucleic Acids Res.* 24:351–366 (1996).

*Oligonucleotides and Analogues: A Practical Approach*, Eckstein, edr., Oxford University Press Ch. 3, pp. 49–59, 137–139, 255–259 (1991).

*Oligonucleotides and Analogues, A Practical Approach*, F. Eckstein, editor, IRL Press Oxford, 1991.

Ornstein et al., Sequencing DNA using $^{35}$S–labeling: A troubleshooting guide, *Biotechniques* 3:476–483 (1985).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial* 181–197 (1992).

Patek, M. and Lebl, M., "Safety–Catch Anchoring Linkage for Synthesis of Peptide Amides by Boc / Fmoc Strategy", *Tetrahedron Lett.*, 32(31):3891–3894 (1991).

Pieles et al., Matrix–assisted laser desorption ionization time–of–flight mass spectrometry: a powerful tool for the mass and sequence analysis of natural and modified oligonucleotides, *Nucleic Acids Res.* 21(14):3191–3196 (1993).

Pierce ImmunoTechnology Catalog, p. 57 (1993).

Pierce Catalog, pp. T123–T154, 1994.

Plunkett, M.J. and Ellman, J.A., "A Silicon–Based Linker for Traceless Solid–Phase Synthesis", *J. Org. Chem.*, 60:6006–6007 (1995).

Pomerantz et al., Determination of oligonucleotide composition from mass spectrometrically measured molecular weight, *Am. Soc. Mass Spectrom.* 4:204–09 (1993).

Pon, et al., Derivation of controlled pore glass beads fo rsolid phase oligonucleotide synthesis, *BioTechniques*, 6:8, 770–775 (1988).

Prome et al., Use of combined mass spectrometry methods for the characterization of a new variant of human hemoglobin: The double mutant hemoglobin villeparisis beta 77(EF1), *J. American Society for Mass Spect* 7(2):163–167 (1996).

Qiagen Catalog, pp. 6–7, Feb. (1991).

Raftery, et al., Characterization of a mutant recombinant S100 protein using electrospray ionization mass spectrometry. *Rapid Comm. Mass Spec.* 11:405–409 (1997).

Rasmussen et al., Covalent immobilization of DNA onto polystyrene microwells: The molecules are only bound at the 5'end, *Anal. Biochem.* 198:138–142 (1991).

Rink, "Solid–phase synthesis of protected peptide fragments using a trialkoxy–diphenyl–methlester resin", *Tetrahedron Lett.* 28:3787–3790 (1987).

Rolfs et al., *PCR: Clinical Diagnostics and Research*, Springer– Verlag (1992).

Rothschild et al., *Nucleic Acids Res.* 24:361–66 (1996).

Routledge, A. et al., "The Use of a Dithiane Protected Benzoin Photolabile Safety Catch Linker for Solid Phase Synthesis", *Tetrahedron Lett.*, 38(7):1227–1230 (1997).

Running and Urdea, A procedure for productive coupling of synthetic oligonucleotides to polystyrene microtiter wells for hybridization capture, *Biotechniques* 8:276–277 (1990).

Ruppert et al., "A rapid and high throughput method for plasmid isolations", Presented: Automation in Mapping and DNA Sequencing Conference, Aug. 31–Sep. 2 1994.

Ruppert et al., "Preparation of plasmid DNA as Sequencing Templates in a Microtiter Plate Format", Paper presented, Cold Spring Harbor Laboratory.

Ruppert et al., "A filtration method for plasmid isolation using microtiter filter plates", *Anal. Biochem.* 230:130–134 (1995).

Saha et al., *J. Org. Chem.* 48:7827–7831 (1993).

Saiki et al., Genetic analysis of amplified DNA with immobilized sequence–specific oligonucleotide probes, *Proc. Natl. Acad. Sci.* 86:6230–6234 (1989).

Salmon, S.E. et al., "Discovery of Biologically Active Peptides in Random Libraries: Solution Phase Testing after Staged Orthogonal Release from Resin Beads", *Proc. Natl. Acad. Sci. USA*, 90:11708–11712 (1993).

Sanger et al., DNA sequencing with chain–terminating inhibitors, *Proc. Natl. Acad. Sci.* 74:5463–67 (1977).

Sasaki et al., Introduction of an azide group into some uridine derivatives via 2',3'–benzoxonium and 2',3'–azidonium intermediates, *J. Org. Chem.* 41:3138–3143 (1976).

Schneider and Chait, Increased stability of nucleic acids containing 7–deaza–guanosine and 7–deaza–adenosine may enable rapid DNA sequencing by matrix–assisted laser desorption mass spectrometry, *Nucleic Acids Res.* 23(9):1570–1575 (1995).

Schram, Karl H., "Mass Spectrometry of Nucleic Acid Components", *Bio Appl of Mass Spect.* 34:203–287 (1990).

Senter et al., Novel photocleavable protein crosslinking reagents and their use in the preparation of antibody–toxin conjugates, Photochem. Photobiol. 42:231–237, (1985).

SEQUENOM Advances the Industrial Genomics Revolution with the Launch of Its DNA MassArray™ Automated Process Line, Press Release: Sep. 28, 1998, http://www.sequenom.com/pressrelease.htm.

SEQUENOM Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

SEQUENOM Reports On Use of Its DNA MassArray™Technology to Analyze Genes Associated with Alzheimer's Disease adn Arteriosclerosis: Technology Has Applications in Drug Development, Press Release: Sep. 22, 1997, http://www.sequenom.com/pressrelease.htm.

SEQUENOM Obtains Important New Patent for DNA MassArray Technology, , Press Release: May 24, 1999, http://www.sequenom.com/pr/pressreleases/52499.html.

SEQUENOM Signs Agreement With Bruker–Franzen Analytik to Develop Mass Spectrometer for DNA Massarray Analysis, Press Release, Jan. 12, 1998, http://www.sequenom.com/pressrelease.htm.

SEQUENOM Uses DNA MassArray™ to Sequence Section of Human Cancer–Related p53 Gene, Press Release: Mar. 27, 1998, http://www.sequenom.com/pressrelease.htm.

SEQUENOM Obtains Patents for DNA MassArraym$^{(SM)}$ Technology, Press Release: Apr. 27, 1999, http://www.sequenom.com/pressrelease/42799.htm.

Shaler et al., "Effect of Impurities on the matrix–Assisted Laser Desorption Mass Spectra of Single–Stranded Oligodeoxynucleotides", *Anal. Chem.* 68:576–579 (1996).

Shaler et al., "Analysis of enzymatic DNA sequencing reactions by matrix–assisted laser desorption/ionization time–of–flight mass spectometry", *Rapid Commun Mass Spectrom 9(10)*:942–947 (1995).

Siegert et al., "Matrix–assisted laser desorption/ionization time–of–flight mass spectrometry for the detection of polymerase chain reaction products containing 7–deazapurine moieties", *Analytical Biochemistry 243*:55–65 (1996).

Singh et al., Oligonucleotides, part 5+: synthesis and fluorescence studies of DNA oligomers d(AT)$_5$ containing adenines covalently linked at C–8 with dansyl fluorophore, *Nucleic Acids Res.* 18(11):3339–3345 (1990).

Sinha et al., β–cyanoethyl N,N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Sinha et al., Polymer support oligonucleotide synthesis XVIII: use of β–cyanoethyl–N,N–dialkylamino–/N–morpholino phosphoramidite of deoxynucleosides for the synthesis of DNA fragments simplyfying deprotection and isolation of the final product, *Nucleic Acids Res.* 12:4539–4557 (1984).

Siuzdak, Gary, "The emergence of mass spectrometry in biochemical research", *Proc. natl. Acad. Sci. USA* 91:11290–11297 (1994).

Slim et al., Configurationally defined phosphorothioate–containing oligoribonucleotides in the study of the mechanism of cleavage of hammerhead ribozymes, *Nucleic Acids Res.* 19:1183–1188 (1991).

Smith et al., Fluorescence detection in automated DNA sequence analysis, *Nature 321*:674–679 (1986).

Smith et al., Capillary zone electrophoresis–mass spectrometry using an electrospray ionization interface, *Anal. Chem.* 60:436–441 (1988).

Smith, Cassandra L., "cDNA Fingerprinting of Breast Cancer Tumor Cells", Boston Univ., MA (1996).

Smith R. D., "New Developments in Biochemical Mass Spectrometry: Electrospray Ionization", *Anal. Chem.* 62:882–899 (1990).

Sproat et al., The synthesis of protected 5'–mercapto–2', 5'–dideoxyribonucleoside–3'–O–phosphoramidites; uses of 5'mercapto–oligodeoxyribonucleotides, *Nucleic Acids Res.* 15:4837–4848 (1987).

Sproat et al., The synthesis of protected 5'–amino–2', 5'–dideoxyribonucleoside–3'–O–phosphoramidites; applications of 5'–amino–oligodeoxyribonucleotides, *Nucleic Acids Res.* 15:6181–6196 (1987).

Stahl et al., Solid Phase DNA Sequencing using the Biotin–Avidin System, *Nucleic Acids Research*, vol. 16, No. 7, pp. 3025–3039 (1988).

Strezoska et al., DNA sequencing by hybridization: 100 bases read by a non–gel–based method, *Proc. Natl. Acad. Sci. 88*:10089–10093 (1991).

Stults and Marsters, *Rapid Comm. Mass Spetrom.* 5:359–363 (1991).

Swerdlow and Gesteland, Capillary gel electrophoresis for rapid, high resolution DNA sequencing, *Nucleic Acids Res.* 18(6):1415–1419 (1990).

Tabor and Richardson, DNA sequence analysis with a modified bacteriophage T7 DNA polymerase, *Proc. Natl. Acad. Sci. 84*:4767–4771 (1987).

Tang et al., Improving mass resolution in MALDI/TOF analysis of DNA.

Tang et al., "Matrix–assisted laser desorption/ionization mass spectrometry of immobilized duplex DNA probes", *Nucleic Acids Research 23*:3126–3131 (1995).

Tang et al., Detection of 500–nucleotide DNA by laser desorption mass spectrometry, *Rapid Commun. Mass Spectrom.* 8:727–730 (1994).

Thuong and Asseline, Oligonucleotides attached to intercalators, photoreactive and cleavage agents, *Oligonucleotides and Analogues: A Practical Approach*, Eckstein, edr., Oxford University Press Ch. 12, pp. 283–308 (1991).

Tomer et al., "Coaxial Continuous Flow Fast Atom Bombardment for Higher–Molecular–Weight Peptides: Comparison with Static Fast Atom Bombardment and electrospray Ionization", *Bio Mass Spect 20*:783–788 (1991).

Tong et al., Solid–phase method for the purification of DNA sequencing reactions, *Anal. Chem.* 64:2672–2677, (1992).

Trainor, "DNA Sequencing, Automation, and the Human Genome", *Anal. Chem.* 62:418–426 (1990).

Valaskovic et al., "Attomole protein characterization by capillary electrophoresis–mass spectrometry", *Science 273*:1199–1202 (1996).

Valaskovic, et al., Attomole–sensitivity electrospray source for large–molecule mass spectrometry, *Anal. Chem.* 67:3802–3805 (1995).

Valaskovic, et al., Attomole–sensitivity electrospray source for large–molecule mass spectrometry, *Anal. Chem.* 67:3802–3805 (1995).

van den Boom D et al., Forward and reverse DNA sequencing in a single reacton, *Anal Biochem.* 256(1):127–9 (1998).

van den Boom D et al., Combined amplification and sequencing in a single reaction using two DNA polymerases with differential incorporation rates for dideoxynucleotides, *J. Biochem Biophys Methods.* 35(2):69–79 (1997).

van Maarseveen, J.H. et al., "Solid Phase Ring–Closing Metathesis: Cyclization / Cleavage Approach towards a Seven Membered Cycloolefin", *Tetrahedron Lett.*, 37(45):8249–8252 (1996).

Vorm, et al., Improved resolution and very high sensitivity in MALDI TOF of matrix surfaces made by fast evaporation, *Anal. Chem.* 66:3281–3287 (1994).

Wallace, "Ink–jet based fluid microdispensing in biochemical applications", *Laboratory Automation News 1*(5):6–9 (1996).

Wang, Solid phase synthesis of protected peptides via photolytic cleavage of the α–methylphenacyl ester anchoring linkage, *J. Org. Chem.* 41(20):3258–3261 (1976).

Wellhöner et al., Uptake and concentration of bioactive macromolecules by K562 cells via the transferrin cycle utilizing an acid–labile transferrin conjugate, *J. Biol. Chem.* 256:4309–4314, (1991).

Wentrup, *Reactive Molecules*, John Wiley & Sons, (1984).

Williams, Time of flight mass spectrometry of DNA laser–ablated from frozen aqueous solutions: applications to the Human Genome Project, *Intl. J. Mass Spectrom. and Ion Processes 131*:335–344 (1994).

Wolter et al., Negative Ion FAB mass spectrometric analysis of non–charged key intermediates in oligonucleotide synthesis: Rapid indentification of partially protected dinucleoside monophosphates, *Biomedical Environmental Mass Spectrometry 14*:111–116 (1987).

Wong, Conjugation of proteins to solid matrices, *Chemistry of Protein Conjugation and Cross–Linking 12*:295–317 (1993).

Wong, Conjugation of proteins to solid matrices, *Chemistry of Protein Conjugation and Cross–Linking*, Table of Contents (1993).

Wood TD et al., Direct sequence data from heterogeneous creatine kinase (43 kDa) by high–resolution tandem mass spectrometry, *Biochemistry* 34(50):16251–4 (1995).

Wu et al., "Matrix–assisted Laser Desorption Time–of–flight Mass Spectrometry of Oligonucleotides Using 3–Hydroxypicolinic Acid as an Ultraviolet–sensitive Matrix", *Rapid Comm Mass Spec 7*:142–146 (1993).

Wu et al., "Time–of–Flight Mass Spectrometry of Underivatized Single–Stranded DNA Oligomers by Matrix–Assisted Laser Desorption", *Anal. Chem. 66*:1637–1645 (1994).

Yamashita et al. Electrospray ion source. Another variation on the free–jet theme, *J. Phys. Chem.* 88:4451–4459, (1984).

Yates, III, Mass spectrometry and the age of the proteome, *J. Mass Spec. 33*:1–19 (1998).

Yen et al., Synthesis of water–soluble copolymers containing photocleavable bonds, *Makromol. Chem. 190*:69–82 (1989).

Zhang et al., Single–base mutational analysis of cancer and genetic diseases using membrane bound modified oligonucleotides, *Nucl. Acids Res. 19*:3929–3933 (1991).

Zimmermann et al., Automated preparation and purification of M13 templates for DNA sequencing, *Meth. Mol. Cell. Biol. 1*:29–34 (1989).

Zuckermann et al., Efficient methods for attachment of thiol specific probes to the 3'–ends of synthetic oligodeoxyribonucleotides, *Nucleic Acids Research*, 15:13, 5305–5321 (1987).

Schober, et al., Accurate High–Speed Liquid Handling of Very Small Biological Samples, Biotechniques, (1993) 15(2):324–329.

* cited by examiner

| k1 6968 Da 170 RP | k2 6968 Da 100 RP | k3 6988 Da 90 RP | k4 6977 Da 100 RP | k5 6971 Da 170 RP | k6 6968 Da 110 RP | k7 6972 Da 160 RP | k8 6978 Da 110 RP | k9 6952 Da 250 RP | k10 6965 Da 300 RP |
|---|---|---|---|---|---|---|---|---|---|
| l1 6965 Da 130 RP | l2 6989 Da 140 RP | l3 6982 Da 210 RP | l4 6996 Da 50 RP | l5 6982 Da 160 RP | l6 6968 Da 180 RP | l7 6984 Da 130 RP | l8 6968 Da 200 RP | l9 6996 Da 80 RP | l10 6968 Da 100 RP |
| m1 6966 Da 190 RP | m2 6979 Da 120 RP | m3 6975 Da 120 RP | m4 6968 Da 190 RP | m5 6976 Da 110 RP | m6 6986 Da 120 RP | m7 6973 Da 160 RP | m8 6978 Da 160 RP | m9 6975 Da 230 RP | m10 6955 Da 250 RP |
| n1 6961 Da 340 RP | n2 6971 Da 180 RP | n3 6970 Da 150 RP | n4 6960 Da 300 RP | n5 6985 Da 120 RP | n6 6953 Da 210 RP | n7 6971 Da 140 RP | n8 6962 Da 160 RP | n9 6957 Da 150 RP | n10 6960 Da 160 RP |
| o1 6965 Da 140 RP | o2 6960 Da 230 RP | o3 6976 Da 200 RP | o4 6953 Da 250 RP | o5 6983 Da 110 RP | o6 6967 Da 250 RP | o7 6970 Da 150 RP | o8 6973 Da 70 RP | o9 6953 Da 140 RP | o10 6952 Da 140 RP |
| p1 6976 Da 140 RP | p2 6981 Da 90 RP | p3 6972 Da 180 RP | p4 6969 Da 90 RP | p5 6984 Da 130 RP | p6 6968 Da 100 RP | p7 6958 Da 290 RP | p8 6981 Da 100 RP | p9 6978 Da 110 RP | p10 6965 Da 150 RP |
| q1 6976 Da 170 RP | q2 6985 Da 100 RP | q3 6990 Da 120 RP | q4 6989 Da 90 RP | q5 6984 Da 90 RP | q6 6969 Da 170 RP | q7 6979 Da 70 RP | q8 6968 Da 140 RP | q9 6973 Da 120 RP | q10 6950 Da 120 RP |
| r1 6966 Da 130 RP | r2 6960 Da 150 RP | r3 6969 Da 100 RP | r4 6964 Da 180 RP | r5 6966 Da 130 RP | r6 6970 Da 110 RP | r7 6972 Da 90 RP | r8 6939 Da 130 RP | r9 6951 Da 230 RP | r10 6965 Da 200 RP |
| s1 6963 Da 130 RP | s2 6953 Da 210 RP | s3 6970 Da 120 RP | s4 6971 Da 170 RP | s5 6957 Da 130 RP | s6 6956 Da 160 RP | s7 6966 Da 140 RP | s8 6975 Da 120 RP | s9 6951 Da 230 RP | s10 6969 Da 120 RP |
| t1 6974 Da 90 RP | t2 6958 Da 160 RP | t3 6959 Da 120 RP | t4 6952 Da 100 RP | t5 6959 Da 110 RP | t6 6954 Da 100 RP | t7 6950 Da 160 RP | t8 6974 Da 140 RP | t9 6967 Da 150 RP | t10 6950 Da 230 RP |

LASER POWER = 41000 FOR ALL SPECTRA.
EACH SPECTRUM THE SUM OF 10-30 SINGLE SHOTS.

HIGH DENSITY IMMOBILIZATION OF NUCLEIC ACIDS

RELATED APPLICATIONS

For U.S. National Stage purposes, this application is a continuation-in-part of a U.S. application filed as Ser. No. 08/947,801 on Oct. 8, 1997, to Maryanne J. O'Donnell-Maloney, Charles R. Cantor, Daniel P. Little and Hubert K öster, entitled "Methods of High Density Immobilization of Nucleic Acids, and Uses Thereof" which is a continuation-in-part of U.S. application Ser. No. 08/746,055, filed Nov. 6, 1996, now abandoned, to Maryanne J. O'Donnell-Maloney, Charles R. Cantor and Hubert Köster, entitled "High Density Immobilization of Nucleic Acid Molecules". This application is also a continuation-in-part of U.S. application Ser. No. 08/746,055, U.S. application Ser. No. 08/786,988, filed Jan. 23, 1997, to Daniel P. Little, Maryanne J. O'Donnell-Maloney, Charles R. Cantor and Hubert Köster, entitled "Systems and Methods for Preparing and Analyzing Low Volume Analyte Array Elements" and U.S. application Ser. No. 08/787,639, filed Jan. 23, 1997 now U.S. Pat. No. 6,024,925, to Daniel P. Little and Hubert Köster, entitled "Systems and Methods for Preparing Low Volume Analyte Array Elements". For international purposes, benefit of priority is claimed to each of these applications.

This application is related to U.S. Pat. Nos. 5,547,835, 5,622,824, 5,605,798.

Where permitted the subject matter of each of the above-noted patent applications and patents is herein incorporated in its entirety.

BACKGROUND OF THE INVENTION

In the fields of molecular biology and biochemistry, as well as in the diagnosis of diseases, nucleic acid hybridization has become a powerful tool for the detection, isolation and analysis of specific oligonucleotide sequences. Typically, such hybridization assays utilize an oligodeoxynucleotide probe that has been immobilized on a solid support; as for example in the reverse dot blot procedure (Saiki, R. K., Walsh, P. S., Levenson, C. H., and Erlich, H. A. (1989) *Proc. Natl. Acad. Sci. USA* 86, 6230). More recently, arrays of immobilized DNA probes attached to a solid surface have been developed for sequencing by hybridization (SBH) (Drmanac, R., Labat, I., Brukner, I., and Crkvenjakov, R. (1989) *Genomics*, 4, 114–128), (Strezoska, Z., Pauneska, T., Radosavljevic, D., Labat, I., Drmanac, R., and Crkvenjakov, R. (1991) *Proc. Natl. Acad. Sci. USA*, 88, 10089–10093). SBH uses an ordered array of immobilized oligodeoxynucleotides on a solid support. A sample of unknown DNA is applied to the array, and the hybridization pattern is observed and analyzed to produce many short bits of sequence information simultaneously. An enhanced version of SBH, termed positional SBH (PSBH), has been developed which uses duplex probes containing single-stranded 3'-overhangs. (Broude, N. E., Sano, T., Smith, C. L., and Cantor, C. R. (1994) *Proc. Natl. Acad. Sci. USA*, 91, 3072–3076). It is now possible to combine a PSBH capture approach with conventional Sanger sequencing to produce sequencing ladders detectable, for example by gel electrophoresis (Fu, D., Broude, N. E., Köster, H., Smith, C. L. and Cantor, C. R. (1995) *Proc. Natl. Acad. Sci. USA* 92, 10162–10166).

For the arrays utilized in these schemes, there are a number of criteria which must be met for successful performance. For example, the immobilized DNA must be stable and not desorb during hybridization, washing or analysis. The density of the immobilized oligodeoxynucleotide must be sufficient for the ensuing analyses. There must be minimal non-specific binding of the DNA to the surface. In addition, the immobilization process should not interfere with the ability of the immobilized probes to hybridize and to be substrates for enzymatic solid phase synthesis. For the majority of applications, it is best for only one point of the DNA to be immobilized, ideally a terminus.

In recent years, a number of methods for the covalent immobilization of DNA to solid supports have been developed which attempt to meet all the criteria listed above. For example, appropriately modified DNA has been covalently attached to flat surfaces functionalized with amino acids (Running, J. A., and Urdea, M. S. (1990) *Biotechniques*, 8, 276–277), (Newton, C. R., et al., (1993) *Nucl. Acids. Res.*, 21, 1155–1162.), (Nikiforov, T. T., and Rogers, Y. H. (1995) *Anal. Biochem.*, 227, 201–209), carboxyl groups, (Zhang, Y., et al., (1991) *Nucl. Acids. Res.*, 19 3929–3933), epoxy groups (Lamture, J. B. et al., (1994) *Nucl. Acids. Res.*, 22, 2121–2125), (Eggers, M. D., et al., (1994) *BioTechniques*, 17, 516–524) or amino groups (Rasmussen, S. R., et al., (1991) *Anal. Biochem.*, 198, 138–142). Although many of these methods were quite successful for their respective applications, the density of oligonucleotide bound (maximum of approximately 20 fmol of DNA per square millimeter of surface) (Lamture, J. B., et al., (1994) *Nucl. Acids. Res.* 22, 2121–2125), (Eggers, M. D., et al., (1994) *BioTechniques*, 17, 516–524), was far less than the theoretical packing limit of DNA.

Therefore, a method for achieving higher densities of immobilized nucleic acids on a surface is needed. In particular, a method for achieving higher densities of surface immobilized nucleic acids which permits use, manipulation and further reaction of the immobilized nucleic acids, as well as analysis of the reactions, is needed.

In connection with the need for improved nucleic acid immobilization methods for use, for example, in analytical and diagnostic systems, is the need to develop sophisticated laboratory tools that will automate and expedite the testing and analysis of biological samples. At the forefront of recent efforts to develop better analytical tools is the goal of expediting the analysis of complex biochemical structures. This is particularly true for human genomic DNA, which is comprised of at least about one hundred thousand genes located on twenty four chromosomes. Each gene codes for a specific protein, which fulfills a specific biochemical function within a living cell. Changes in a DNA sequence are known as mutations and can result in proteins with altered or in some cases even lost biochemical activities; this in turn can cause a genetic disease. More than 3,000 genetic diseases are currently known. In addition, growing evidence indicates that certain DNA sequences may predispose an individual to any of a number of genetic diseases, such as diabetes, arteriosclerosis, obesity, certain autoimmune diseases and cancer. Accordingly, the analysis of DNA is a difficult but worthy pursuit that promises to yield information fundamental to the treatment of many life threatening diseases.

Unfortunately, the analysis of DNA is made particularly cumbersome due to size and the fact that genomic DNA includes both coding and non-coding sequences (e.g., exons and introns). As such, traditional techniques for analyzing chemical structures, such as the manual pipeting of source material to create samples for analysis, are of minimal value. To address the scale of the necessary analysis, scientists have developed parallel processing protocols for DNA diagnostics.

For example, scientists have developed robotic devices that eliminate the need for manual pipeting and spotting by providing a robotic arm that carries at its proximal end a pin tool device that consists of a matrix of pin elements. The individual pins of the matrix are spaced apart from each other to allow each pin to be dipped within a well of a microtiter plate. The robotic arm dips the pins into the wells of the microtiter plate thereby wetting each of the pin elements with sample material. The robotic arm then moves the pin tool device to a position above a target surface and lowers the pin tool to the surface contacting the pins against the target to form a matrix of spots thereon. Accordingly, the pin tool expedites the production of samples by dispensing sample material in parallel.

Although this pin tool technique works well to expedite the production of sample arrays, it suffers from several drawbacks. First during the spotting operation, the pin tool actually contacts the surface of the substrate. Given that each pin tool requires a fine point in order that a small spot size is printed onto the target, the continuous contact of the pin tool against the target surface will wear and deform the fine and delicate points of the pin tool. This leads to errors which reduce accuracy and productivity.

An alternative technique developed by scientists employs chemical attachment of sample material to the substrate surface. In one particular process, DNA is synthesized in situ on a substrate surface to produce a set of spatially distinct and diverse chemical products. Such techniques are essentially photolithographic in that they combine solid phase chemistry, photolabile protecting groups and photo activated lithography. Although these systems work well to generate arrays of sample material, they are chemically intensive, time consuming, and expensive.

It is further troubling that neither of the above techniques provide sufficient control over the volume of sample material that is dispensed onto the surface of the substrate. Consequently, error can arise from the failure of these techniques to provide sample arrays with well controlled and accurately reproduced sample volumes. In an attempt to circumvent this problem, the preparation process will often dispense generous amounts of reagent materials. Although this can ensure sufficient sample volumes, it is wasteful of sample materials, which are often expensive and of limited availability.

Even after the samples are prepared, scientists still must confront the need for. sophisticated diagnostic methods to analyze the prepared samples. To this end, scientists employ several techniques for identifying materials such as DNA. For example, nucleic acid sequences can be identified by hybridization with a probe which is complementary to the sequence to be identified. Typically, the nucleic acid fragment is labeled with a sensitive reporter function that can be radioactive, fluorescent, or chemiluminescent. Although these techniques can work well, they do suffer from certain drawbacks. Radioactive labels can be hazardous and the signals they produce decay over time. Nonisotopic (e.g. fluorescent) labels suffer from a lack of sensitivity and fading of the signal when high intensity lasers are employed during the identification process. In addition, labeling is a laborious and time consuming error prone procedure. Consequently, the process of preparing and analyzing arrays of a biochemical sample material is complex and error prone.

Therefore, it is an object herein to provide improved systems and methods for preparing arrays of sample material. It is a further object to provide systems that allow for the rapid production of sample arrays. It is a further object herein to provide supports to which high densities of nucleic acids molecules are linked.

SUMMARY OF THE INVENTION

Processes for immobilizing a high density of nucleic acids on a surface, which are based on rapidly reacting a free thiol group of a modified surface or modified nucleic acid, under appropriate conditions, with a thiol-reactive functionality of the other component (surface or nucleic acid) are provided. This reaction may be direct or through a bifunctional cross-linking reagent. In a preferred embodiment, the modified nucleic acid includes a thiol group and the cross-linking reagent contains an iodoacetyl group.

Solid supports to which are linked "beads" which are linked to nucleic acid molecules are also provided. The beads are not necessarily spherical, but refer to particles that are conjugated to the solid support to thereby increase the surface area of the solid support and/or to provide an alternative surface for conjugation of nucleic acids or other molecules. The beads are preferably of a size of about 1 $\mu$m to 100 $\mu$m. Compositions containing at least one bead conjugated to a solid support and further conjugated to at least one molecule, particularly a nucleic acid are provided. The bead is formed from any suitable matrix material known to those of skill in the art, including those that are swellable and nonswellable. The solid support is any support known to those of skill in the art for use as a support matrix in chemical syntheses and analyses. In such instances, the nucleic acid is linked to the "bead" via a sulfur atom as described herein. In certain embodiments, the beads may be conjugated on the solid support in wells or pits on the surface, or the beads may be arranged in the form of an array on the support.

Preferably the bead is made of a material selected from materials that serve as solid supports for synthesis and for assays including but not limited to: silica gel, glass, magnet, polystyrene/1% divinylbenzene resins, such as Wang resins, which are Fmoc-amino acid-4-(hydroxy-methyl) phenoxymethylcopoly(styrene-1% divinylbenzene (DVD)) resin, chlorotrityl (2-chlorotritylchloride copolystyrene-DVB resin) resin, Merrifield (chloromethylated copolystyrene-DVB) resin metal, plastic, cellulose, cross-linked dextrans, such as those sold under the tradename Sephadex (Pharmacia) and agarose gel, such as gels sold under the tradename Sepharose (Pharmacia), which is a hydrogen bonded polysaccharide-type agarose gel, and other such resins and solid phase supports known to those of skill in the art. In a preferred embodiment, the bead is of a size in the range of about 0.1 to 500 $\mu$m, more preferably about 1 to 100 $\mu$m, in diameter.

The solid support is in any desired form, including, but not limited to: a bead, capillary, plate, membrane, wafer, comb, pin, a wafer with pits, an array of pits or nanoliter wells and other geometries and forms known to those of skill in the art.

In another aspect, kits for immobilized nucleic acids on an insoluble support are provided. In one embodiment, the kit can comprise an appropriate amount of: i) a thiol-reactive cross-linking reagent; and ii) a surface-modifying reagent for modifying a surface with functionality which can react with the thiol-reactive cross-linking reagent. The kit can optionally include an insoluble support, e.g., a solid surface, magnetic microbeads or silicon wafers, for use in immobilizing nucleic acids. The kit can also optionally include appropriate buffers as well as instructions for use.

Use of these processes for immobilizing nucleic acid molecules onto a solid support results in at least 12.5-fold higher immobilization than previously reported techniques. The processes are therefore particularly useful for forming nucleic acid launching pads for mass spectrometry.

The nucleic acids immobilized on a surface using the methods provided herein can be used in a variety of solid phase nucleic acid chemistry applications, including but not limited to nucleic acid synthesis (chemical and enzymatic), hybridization and/or extension, and in diagnostic methods based in nucleic acid detection and polymorphism analyses (see, e.g., U.S. Pat. No. 5,605,798). Accordingly, further provided herein are methods of reacting nucleic acid molecules in which the nucleic acid molecules are immobilized on a surface either by reacting a thiol-containing derivative of the nucleic acid molecule with an insoluble support containing a thiol-reactive group or by reacting a thiol-containing insoluble support with a thiol-reactive group-containing derivative of the nucleic acid molecule and thereafter further reacting the immobilized nucleic acid molecules.

In a particular embodiment of the methods of reacting immobilized nucleic acids, the immobilized nucleic acid is further reacted by hybridizingxwith a nucleic acid that is complementary to the immobilized nucleic acid or a portion thereof. Such hybridization reactions can be used to detect the presence of a specific nucleic acid in a sample. This is of particular use in the detection of pathogens in a sample, such as a biological sample, that may be employed in the diagnosis of diseases.

Therefore, also provided herein are methods of detecting a target nucleic acid in a sample wherein a thiol-containing nucleic acid complementary to the target nucleic acid is immobilized to a surface using the processes described herein and the sample is contacted with the surface under conditions whereby target nucleic acid in the sample hybridizes to the immobilized nucleic acid. The hybridized target nucleic acid may be detected using a variety of methods, the preferred method being mass spectrometry. Further provided herein are methods of detecting alterations (e.g., deletions, insertions and conversions) in the nucleotide sequence of the target nucleic acid. In these methods, the molecular weight of the hybridized target nucleic acid, as determined by mass spectrometry, is compared to the molecular weight expected for the target nucleic acid sequence. Deviations of the measured molecular weight from the expected molecular weight are indicative of an alteration in the nucleotide sequence of the target nucleic acid.

In other methods of detecting a target nucleic acid in a sample as provided herein, the target nucleic acid is immobilized to a surface containing thiol-reactive groups. In these methods, prior to immobilization, the target nucleic acid is amplified in a reaction in which an oligonucleotide primer contains a 3'- or 5'-disulfide linkage and the resulting product is reduced to generate a thiol-containing nucleic acid. The thiol-containing nucleic acid is immobilized to a surface containing thiol-reactive groups and is contacted with a single-stranded nucleic acid that is complementary to the immobilized nucleic acid or a portion thereof. Hybridization of the single-stranded nucleic acid may be detected by a variety of methods. For example, the single-stranded nucleic acid may be labeled with a readily detectable moiety, e.g., radioactive or chemiluminescent labels. In a preferred embodiment, the single-stranded nucleic acid is detected by mass spectrometry.

In another embodiment of the methods of reacting immobilized nucleic acids, the immobilized nucleic acid is further reacted by extension of a nucleic acid that is hybridized to the immobilized nucleic acid or a portion thereof. Extension reactions such as these can be used, for example, in methods of sequencing DNA molecules that are immobilized to an insoluble support using the processes described herein. Thus, also provided herein are methods of determining the sequence of a DNA molecule on a substrate in which a thiol-containing derivative of the DNA molecule is immobilized on the surface of an insoluble support containing thiol-reactive groups and hybridized with a single-stranded nucleic acid complementary to a portion of the immobilized DNA molecule prior to carrying out DNA synthesis in the presence of one or more dideoxynucleotides.

Extension of a nucleic acid primer that is hybridized to a nucleic acid immobilized to a surface as provided herein also can be used in the detection of nucleotide sequence alterations (e.g., deletions, insertions, conversions) of a target nucleic acid. Accordingly, provided herein are methods of detecting alterations in a target nucleic acid sequence in which a single-stranded nucleic acid is hybridized to a thiol-containing target nucleic acid immobilized to a solid support according to the processes provided herein and the hybridized single-stranded nucleic acid is extended by addition of nucleotides to the 3' end of the molecule. The extension product is characterized by, for example, mass spectrometry to determine whether its characteristics differ from those expected of a sequence complementary to the immobilized target nucleic acid. Thus, for example, the molecular weight of the extension product determined by mass spectrometry is compared to the expected molecular weight of a nucleic acid complementary to the target nucleic acid. Deviations from the expected molecular weight are indicative of an alteration in the sequence of the target nucleic acid.

In particular embodiments of the methods of detecting alterations in a target nucleic acid sequence provided herein, the target nucleic acid may be amplified prior to immobilization to a thiol-reactive surface in a reaction in which an oligonucleotide primer contains a 3'- or 5'-disulfide linkage. The resulting product is reduced to generate a thiol-containing target nucleic acid. The thiol-containing target nucleic acid is then immobilized to a surface containing thiol-reactive groups and the single-stranded complementary nucleic acid is hybridized thereto and extended.

In a further embodiment of the methods of detecting alterations in a target nucleic acid sequence provided herein, a single-stranded nucleic acid complementary to the target nucleic acid is immobilized to a surface through a linkage that includes a thiol group-thiol reactive functionality bond and a cleavable linker moiety. The sample containing target nucleic acid is contacted with the surface under conditions whereby the target hybridizes with the immobilized single-stranded nucleic acid. The immobilized single-stranded nucleic acid is extended by addition of nucleotides to the 3' end of the molecule. Following extension, the double-stranded molecule is denatured and the single-stranded immobilized extension product is cleaved from the surface at the position of the linker. The extension product is characterized by, for example, mass spectrometry to determine whether its characteristics differ from those expected of a sequence complementary to the immobilized target nucleic acid.

It is understood that all applications of the solid phase nucleic acid chemistry based on nucleic acids immobilized to a solid substrate according to the processes provided herein can be conducted with thiol-containing nucleic acids and a thiol-reactive surface as well as with thiol-reactive nucleic acids and a thiol-containing support.

Methods of forming an array of nucleic acids on a surface of a substrate by contacting thiol-containing nucleic acids with an insoluble support containing thiol-reactive groups positioned in an ordered arrangement on the surface of the support are also provided herein. In an alternative method of forming an array of nucleic acids on a surface of a substrate as provided herein, an insoluble support containing thiol functionalities positioned in an ordered arrangement on the surface of the support is contacted with nucleic acids containing a thiol-reactive group.

Further provided herein are systems and methods for preparing a sample for analysis, and more specifically to systems and methods for dispensing low volumes of fluid material onto a substrate surface for generating an array of samples for diagnostic analysis. Systems and methods provided herein for preparing arrays of sample material are generally less expensive to employ and conserve reagent materials while allowing for the rapid production of highly reproducible sample arrays.

Provided herein with respect to systems and methods for dispensing low volumes of fluid material onto a substrate surface are serial and parallel dispensing tools that can be employed to generate multi-element arrays of sample material on a substrate surface. The substrate surfaces can be flat or geometrically altered to include wells of receiving material.

In one embodiment, the tool is one that allows the parallel development of a sample array. To this end, the tool can be understood as an assembly of vesicle elements, or pins, wherein each of the pins can include a narrow interior chamber suitable for holding nanoliter volumes of fluid. Each of the pins can fit inside a housing that itself has an interior chamber. The interior housing can be connected to a pressure source that will control the pressure within the interior housing chamber to regulate the flow of fluid through the interior chamber of the pins. This allows for the controlled dispensing of defined volumes of fluid from the vesicles.

In an alternative embodiment, the tool includes a jet assembly that can include a capillary pin having an interior chamber, and a transducer element mounted to the pin and capable of driving fluid through the interior chamber of the pin to eject fluid from the pin. In this way, the tool can dispense a spot of fluid to a substrate surface by spraying the fluid from the pin. Alternatively, the transducer can cause a drop of fluid to extend from the capillary so that fluid can be passed to the substrate by contacting the drop to the surface of the substrate.

Further, the tool can form an array of sample material by dispensing sample material in a series of steps, while moving the pin to different locations above the substrate surface to form the sample array. In a further embodiment, the prepared sample arrays are passed to a plate assembly that disposes the sample arrays for analysis by mass spectrometry. To this end, a mass spectrometer is provided that generates a set of spectra signal which can be understood as indicative of the composition of the sample material under analysis.

In one aspect, the dispensing apparatus provided herein for dispensing defined volumes of fluid, including nanovolumes and sub-nanovolumes of fluid, in chemical or biological procedures onto the surface of a substrate can include a housing having a plurality of sides and a bottom portion having formed therein a plurality of apertures, the walls and bottom portion of the housing defining an interior volume; one or more fluid transmitting vesicles, or pins, mounted within the apertures, having a nanovolume sized fluid holding chamber for holding nanovolumes of fluid, the fluid holding chamber being disposed in fluid communication with the interior volume of the housing, and a dispensing element that is in communication with the interior volume of the housing for selectively dispensing nanovolumes of fluid from the nanovolume sized fluid transmitting vesicles when the fluid is loaded into the fluid holding chambers of the vesicles. As described herein, this allows the dispensing element to dispense nanovolumes of the fluid onto the surface of the substrate when the apparatus is disposed over and in registration with the substrate.

In one embodiment the fluid transmitting vesicle has an open proximal end and a distal tip portion that extends beyond the housing bottom portion when mounted within the apertures. In this way the open proximal end can dispose the fluid holding chamber in fluid communication with the interior volume when mounted with the apertures. Optionally, the plurality of fluid transmitting vesicles are removably and replaceably mounted within the apertures of the housing, or alternatively can include a glue seal for fixedly mounting the vesicles within the housing.

In one embodiment the fluid holding chamber includes a narrow bore dimensionally adapted for being filled with the fluid through capillary action, and can be sized to fill substantially completely with the fluid through capillary action.

In one embodiment, the plurality of fluid transmitting vesicles comprise an array of fluid delivering needles, which can be formed of metal, glass, silica, polymeric material, or any other suitable material.

In one embodiment the housing can include a top portion, and mechanical biasing elements for mechanically biasing the plurality of fluid transmitting vesicles into sealing contact with the housing bottom portion. In one particular embodiment, each fluid transmitting vesicle has a proximal end portion that includes a flange, and further includes a seal element disposed between the flange and an inner surface of the housing bottom portion for forming a seal between the interior volume and an external environment. The biasing elements can be mechanical and can include a plurality of spring elements each of which is coupled at one end to the proximal end of each of the plurality of fluid transmitting vesicles, and at another end to an inner surface of the housing top portion. The springs can apply a mechanical biasing force to the vesicle proximal end to form the seal.

In a further embodiment, the housing further includes a top portion, and securing element for securing the housing top portion to the housing bottom portion. The securing element can comprise a plurality of fastener-receiving apertures formed within one of the top and bottom portions of the housing, and a plurality of fasteners for mounting within the apertures for securing together the housing top and bottom portions.

In one embodiment the dispensing element can comprise a pressure source fluidly coupled to the interior volume of the housing for disposing the interior volume at a selected pressure condition. Moreover, in an embodiment wherein the fluid transmitting vesicles are filled through capillary action, the dispensing element can include a pressure controller that can vary the pressure source to dispose the interior volume of the housing at varying pressure conditions. This allows the controller varying element to dispose the interior volume at a selected pressure condition sufficient to offset the capillary action to fill the fluid holding chamber of each vesicle to a predetermined height corresponding to a predetermined fluid amount. Additionally, the controller can further include a fluid selection element for selectively discharging a selected nanovolume fluid amount from the chamber of each vesicle. In one particular embodiment, a pressure controller is included that operates under the controller of a computer program operating on a data processing system to provide variable control over the pressure applied to the interior chamber of the housing.

In one embodiment the fluid transmitting vesicle can have a proximal end that opens onto the interior volume of the housing, and the fluid holding chamber of the vesicles are sized to substantially completely fill with the fluid through capillary action without forming a meniscus at the proximal open end. Optionally, the apparatus can have plural vesicles, wherein a first portion of the plural vesicles include fluid holding chambers of a first size and a second portion including fluid holding chambers of a second size, whereby plural fluid volumes can be dispensed.

In another embodiment, the dispensing apparatus can include a fluid selection element that has a pressure source coupled to the housing and in communication with the interior volume for disposing the interior volume at a selected pressure condition, and an adjustment element that couples to the pressure source for varying the pressure within the interior volume of the housing to apply a positive pressure in the fluid chamber of each of the fluid transmitting vesicles to vary the amount of fluid dispensed therefrom. The selection element and adjustment element can be computer programs operating on a data processing system that directs the operation of a pressure controller connected to the interior chamber.

In a further alternative embodiment, the apparatus provided herein is for dispensing a fluid in chemical or biological procedures into one or more wells of a multi-well substrate. The apparatus can include a housing having a plurality of sides and a bottom portion having formed therein a plurality of apertures, the walls and bottom portion defining an interior volume, a plurality of fluid transmitting vesicles, mounted within the apertures, having a fluid holding chamber disposed in communication with the interior volume of the housing, and a fluid selection and dispensing means in communication with the interior volume of the housing for variably selecting am amount of the fluid loaded within the fluid holding chambers of the vesicles to be dispensed from a single set of the plurality of fluid transmitting vesicles. Accordingly, the dispensing means dispenses a selected amount of the fluid into the wells of the multi-well substrate when the apparatus is disposed over and in registration with the substrate.

In yet another embodiment, provided herein is a fluid dispensing apparatus for dispensing fluid in chemical or biological procedures into one or more wells of a multi-well substrate, that comprises a housing having a plurality of sides and top and bottom portions, the bottom portion having formed therein a plurality of apertures, the walls and top and bottom portions of the housing defining an interior volume, a plurality of fluid transmitting vesicles, mounted within the apertures, having a fluid holding chamber sized to hold nanovolumes of the fluid, the fluid holding chamber being disposed in fluid communication with the volume of the housing, and mechanical biasing element for mechanically biasing the plurality of fluid transmitting vesicles into sealing contact with the housing bottom portion.

General methods for preparing an array of sample material on a surface of a substrate as described herein include the steps of providing a vesicle having an interior chamber containing a fluid, disposing the vesicle adjacent a first location on the surface of the substrate, controlling the vessel for delivering a nanoliter volume of a fluid at the first location of the surface of the substrate, and moving the vesicle to a set of positions adjacent to the surface substrate whereby fluid is dispensed at each location of the set of positions for forming an array of sample material;

Substrates employed during the general processes of preparing an array of sample material described herein can include flat surfaces for receiving the sample material as well as having the surfaces that include wells formed on the surface for defining locations for receiving the fluid that can be ejected from the chambers of the vesicles. Such substrates can be silicon, metal, plastic, a membrane, polymeric material, a metal-grafted polymer, as well as a substrate that is functionalized chemically, functionalized with beads, functionalized with dendrite trees of captured material, or any combinations of the above or any similar suitable material for receiving the dispensed fluid.

It is understood that in the general methods for preparing an array of sample material on a substrate surface described herein the apparatus can dispense both an analyte material as well as a support material, such as a matrix material, that aids in the analysis of the analyte. To this end the methods provided herein can include the steps of depositing a matrix material onto the substance of the substrate. Further the methods can also include a step of waiting a predetermined period of time to allow a solvent of the matrix material to evaporate. Once the solvent of the matrix material has evaporated, the methods herein can include a step of ejecting a volume of analyte fluid into the evaporated matrix material to dissolve with the matrix material and to form a crystalline structure on the substrate surface. It is understood that this step of redissolving the matrix material with the analyte material aids in the analysis of the composition of the material during certain analytical processes, such as mass spectrometry.

In an alternative practice, the methods herein can include a step of dispensing a mixture that consists of the analyte material and the matrix material, as well as other material compositions. In this way the matrix and the analyte are delivered to the surface of the substrate as one volume of material. In a further step, the prepared arrays of sample material can be provided to a diagnostic tool for determining information that is representative of the composition of the sample material.

Once such diagnostic tool can include a mass spectrometer. The mass spectrometers can be time of flight mass spectrometers, Fourier transform mass spectrometers or any other suitable type of mass spectrometer that allows the analysis of composition of the sample array.

In one practice of the methods, the step of providing a vesicle having an interior chamber includes the step of providing a vesicle having a piezo electric element for causing fluid to move through the chamber. This method can also include the step of moving the vesicle by rasterizing the vesicle across the surface of the substrate, to form the array of sample material.

In an alternative practice of the methods, parallel processing protocols can be employed wherein the vesicle that is employed during the processing includes a vesicle assembly that has a plurality of vesicles arranged into a matrix for dispensing fluid to a first plurality of locations on the substrate surface. In this way in a single operation, the method provides for forming a matrix of a sample material on the substrate surface. Offset printing can also be employed to form a large matrix of sample material by employing multiple printing steps with the vesicle matrix. Other printing techniques can be employed by the present invention without departing from the scope thereof.

In another embodiment, fluid can be dispensed to the surface of the substrate by contacting the vesicle against the surface of the substrate to spot the surface of the substrate with sample material. Alternatively, the methods provide for another non-contact printing approach wherein the processes of the invention cause a drop of fluid to be formed on at the distal tip of the vesicle. It is the drop of fluid that is contacted against the surface of the substrate for delivering sampling material thereto. This provides for the controlled delivery for the known volume of fluid without resulting in the contacting of the vesicle against the surface of the substrate.

In further embodiments, vesicles are provided having an interior chamber that is dimensionally adapted to allow filling of the chamber by capillary action.

In another aspect, methods are provided for analyzing a material, that comprise the steps of providing a vesicle suitable for carrying a fluid having the material therein, disposing the vesicle adjacent a first location of the surface of the substrate, controlling the vesicle to deliver a nanoliter volume of the fluid to provide a defined and controlled volume of fluid at the first location of the surface of the substrate, moving the vesicle to a second position adjacent a second location on the surface on the substrate to dispense a defined and controlled volume of the material along an array of locations along the substrate surface, and performing mass spectrometry analysis of the material at each location of the array. These methods can include the step of mixing a matrix material and an analyte material to form the fluid being delivered to the substrate surface. Alternatively, this embodiment can include the steps of filling a chamber contained within the vesicle with a matrix material and dispensing the matrix material to the array of locations. Subsequently, analyte can be dispensed. The step of performing mass spectrometry can include the step of performing a matrix assisted laser desorption ionization mass spectrometry, as well as time of flight mass spectrometry, or a Fourier transform spectrometry.

In another aspect, apparatus for forming an array of a sample material on a surface of a substrate are provided. Such apparatus will compromise a vesicle having a distal end suitable for carrying a fluid thereon, a movable arm having a distal portion mounted to the vesicle, a controller for moving the arm to dispose the vesicle adjacent a first location on the surface on the substrate and for controlling the vesicle to provide a nanoliter volume of the fluid at the first location of the surface of the substrate, and a diagnostic tool for analyzing the material to generate a composition signal that is representative of the chemical composition of the material. In this apparatus the vesicle can compromise a solid shaft of material as well as a vesicle having an interior chamber suitable for carrying fluid as well as a chamber for carrying a fluid in a transducer element for ejecting fluid from that chamber.

Further provided herein are substrates having a surface for carrying an array of a matrix material and formed according to a process comprising the steps of a providing a vesicle suitable for transferring a fluid containing a matrix material, disposing the vesicle adjacent a first location on the surface on the substrate, controlling the vesicle to deliver the fluid to the first location of the surface of the substrate, and moving a vesicle to a set of positions adjacent the surface of the substrate and delivering fluid at each of these locations to form an array of matrix material. This substrate itself can be a flat silicon chip as well as a any other suitable material, and can be pitted, include wells, and have wells that have rough interior surfaces.

In particular embodiments, the methods of forming an array of nucleic acids on a surface of a substrate as provided herein include contacting predetermined positions of the surface of an insoluble support with thiol-containing nucleic acid solutions dispensed to the positions with a vesicle having an interior chamber containing the respective solutions whereby the predetermined positions incorporate thiol-reactive groups. Alternatively, the entire surface of the substrate is derivatized with the thiol-reactive groups and thiol-containing nucleic acid is dispensed to predetermined positions on the surface in an array-forming manner. Also provided herein are substrates having a surface carrying an array of nucleic acids formed by the methods described herein.

The above and further features and advantages of the instant invention will become clearer from the following Figures, Detailed Description and Claims.

BRIEF DESCRIPTION OF THE DRAWINGS

FIG. 13 depicts molecular weights determined for the sample material having spectra identified in FIG. 12.

FIG. 14 is a schematic of a 4×4 (16-location) DNA array on the surface of a silicon wafer with the thiol-containing oligonucleotide molecules denoted "Oligomer 1", [5'-CTGGATGCGTCGGATCATCTTTTTT-(S)-3'; SEQ ID NO: 8], Oligomer 2 [5'-(S)-CCTCTTGGGAACTGTGTAGTATT-3'; SEQ ID NO: 3]and "Oligomer 3" (SEQ ID NO: 1; a free thiol derivative "TCUC" oligonucleotide of EXAMPLE 1) covalently bound to 16 locations on the surface of the silicon wafer essentially as described in EXAMPLE 2.

FIG. 15 is a schematic of the hybridization of specific oligonucleotides to each of the 16 locations of the DNA hybridization array of FIG. 14 with the Oligomer 1 complementary oligonucleotide (5'-GATGATCCGACGCATCAGAATGT-3'; SEQ ID NO: 9) bound to Oligomer 1, the Oligomer 2 complementary oligonucleotide (5'-AATACTACACAG-3'; SEQ ID NO: 7) bound to Oligomer 2 and the Oligomer 3 complementary oligonucleotide (5'-CCGGGTACCGAGCTCGAATTC-3'; SEQ ID NO: 2) bound to Oligomer 3.

DETAILED DESCRIPTION AND PREFERRED EMBODIMENTS

Definitions

Figure 1:
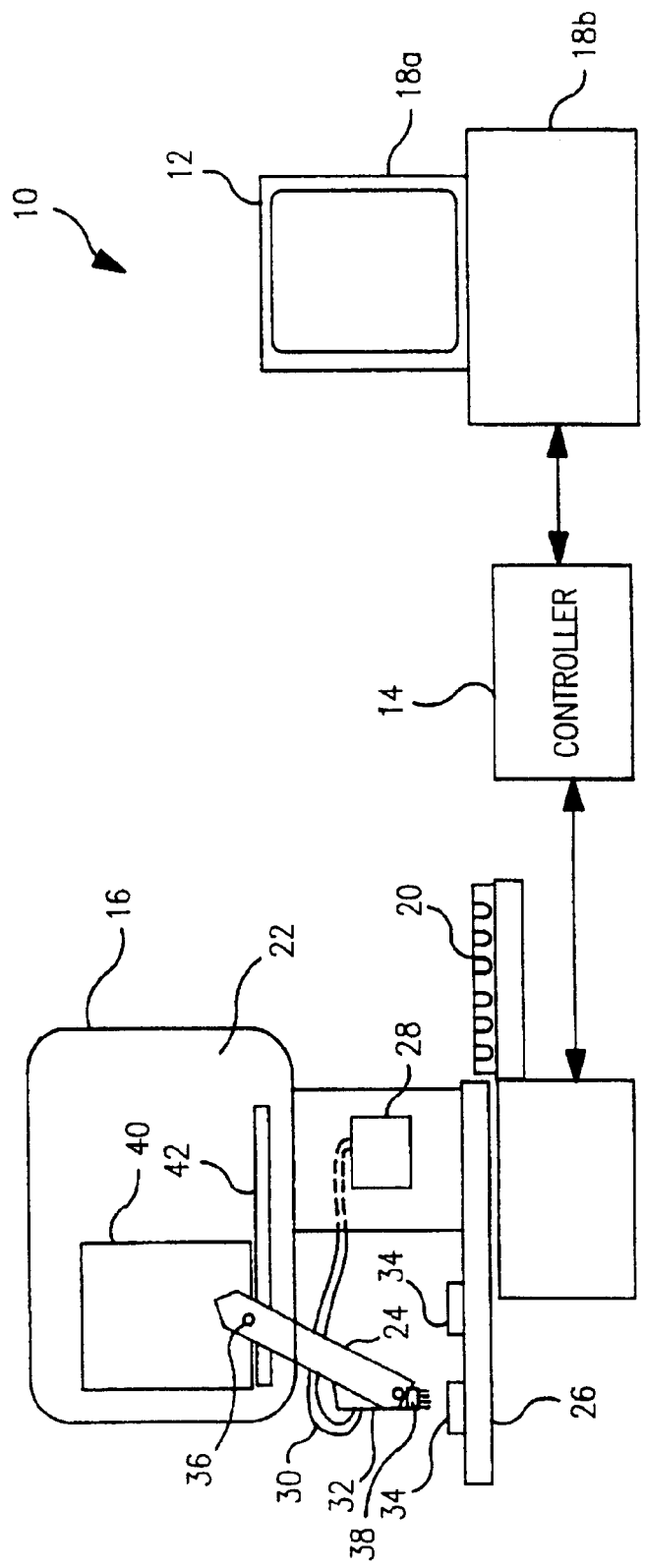
FIG. 1 illustrates a system for preparing arrays of a sample material for analysis.

Unless defined otherwise, all technical and scientific terms used herein have the same meaning as is commonly understood by one of skill in the art to which this invention belongs. All patents and publications referred to herein are incorporated by reference herein.

As used herein, the term, "nucleic acid" refers to oligonucleotides or polynucleotides such as deoxyribonucleic acid (DNA) and ribonucleic acid (RNA) as well as analogs of either RNA or DNA, for example, made from nucleotide analogs, any of which are in single or double-stranded form. Nucleic acid molecules can be synthetic or can be isolated from a particular biological sample using any number of procedures which are well-known in the art, the particular procedure chosen being appropriate for the particluar biological sample.

As used herein nucleotides include nucleoside mono-, di-, and triphosphates. Nucleotides also include modified nucleotides such as phosphorothioate nucleotides and deazapurine nucleotides. A complete set of chain-elongating nucleotides refers to four different nucleotides that can hybridize to each of the four different bases comprising the DNA template.

As used herein, nucleic acid synthesis refers to any process by which oligonucleotides or polynucleotides are generated, including, but not limited to processes involving chemical or enzymatic reactions.

As used herein, the term "array" refers to an ordered arrangement of members or positions. The array may contain any number of members or positions and can be in any variety of shapes. In preferred embodiments, the array is two-dimensional and contains n×m members, wherein m and n are integers that can be the same or different. In particularly preferred embodiments, n and m are each 4 or a multiple thereof.

The term "cross-linking agent" is art-recognized, and, as used herein, refers to reagents which can immobilize a nucleic acid to an insoluble-support, preferably through covalent bonds. Thus, appropriate "cross-linking agents" for use herein includes a variety of agents that are capable of reacting with a functional group present on a surface of the insoluble support and with a functional group present in the nucleic acid molecule. Reagents capable of such reactivity include homo- and hetero-bifunctional reagents, many of which are known in the art.
Heterobifunctional Reagents are Preferred.

As used herein, the term "thio-reactive functionality," refers to a functionality which is capable of rapid reaction with a nucleophilic thiol moiety to produce a covalent bond (e.g., a disulfide or thioether bond). In general, thiol groups are good nucleophiles, and preferred thiol-reactive functionalities are reactive electrophiles. A variety of thiol-reactive functionalities are known in the art, and include, for example, haloacetyls (preferably iodoacetyl), diazoketones, epoxy ketones, $\alpha$, $\beta$-unsaturated carbonyls (e.g., $\alpha$, $\beta$-enones) and other reactive Michael acceptors (including maleimide), acid halides, benzyl halides, and the like. In certain embodiments, a free thiol group of a disulfide can react with a free thiol group (i.e., by disulfide bond formation, including by disulfide exchange). A "thiol-reactive" cross-linking agent, as used herein, refers to a cross-linking reagent (or surface) which includes, or can be modified to include, at least one thiol-reactive functionality. It will be understood that reaction of a thiol group can be temporarily prevented by blocking with an appropriate protecting group, as is conventional in the art (see e.g., T. W. Greene and P. G. M. Wuts "Protective Groups in Organic Synthesis," 2nd ed. John Wiley & Sons, (1991)).

As used herein, a selectively cleavable linker is a linker that is cleaved under selected conditions, such as a photo-cleavable linker, a chemically cleavable linker and an enzymatically cleavable linker (i.e., a restriction endonuclease site or a ribonucleotide/RNase digestion). The linker is interposed between the support and immobilized DNA.

As used herein, the terms "protein", "polypeptide" and "peptide" are used interchangeably when referring to a translated nucleic acid (e.g. a gene product).

As used herein, "sample" shall refer to a composition containing a material to be detected. In a preferred embodiment, the sample is a "biological sample" (i.e., any material obtained from a living source (e.g. human, animal, plant, bacteria, fungi, protist, virus). The biological sample can be in any form, including solid materials (e.g. tissue, cell pellets and biopsies) and biological fluids (e.g. urine, blood, saliva, amniotic fluid and mouth wash (containing buccal cells)). Preferably solid materials are mixed with a fluid.

As used herein, "substrate" shall mean an insoluble support onto which a sample is deposited according to the materials as described herein. Examples of appropriate substrates include beads. (e.g., silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates.

In the particular methods of immobilizing nucleic acids to a substrate provided herein, preferred substrates are those which can support linkage of nucleic acids thereto at high densities, preferrably such that the covalently bound nucleic acids are present on the substrate at a density of at least about 20 fmol/mm$^2$, more preferably at least about 75 fmol/mm$^2$, still more preferably at least about 85 fmol/mm$^2$, yet more preferably at least about 100 fmol/mm$^2$, and most preferably at least about 150 fmol/mm$^2$. Among the most preferred substrates for use in the particular methods of immobilizing nucleic acids to substrates provided herein is silicon, whereas less preferred substrates include polymeric materials such as polyacrylamide. Substrates for use in methods of producing arrays provided herein include any of a wide variety of insoluble support materials including, but not limited to silica gel, controlled pore glass, cellulose, glass fiber filters, glass surfaces, metal surfaces (steel, gold, silver, aluminum, silicon and copper), plastic materials (e.g., of polyethylene, polypropylene, polyamide, polyvinyidenedifluoride) and silicon.

High Density Immobilization of Nucleic Acids to Solid Supports

The methods described herein provide for high density immobilization of nucleic acid molecules on a insoluble (e.g., solid) support. In general, nucleic acid molecules are immobilized on the insoluble support either directly or by means of cross-linking agents.

In embodiments of the methods in which a cross-linking reagent is not employed, a modified nucleic acid is reacted directly with a appropriately functionalized surface to yield immobilized nucleic acid. Thus, for example, an iodoacetyl-modified surface (or other thiol-reactive surface functionality) can react with a thiol-modified nucleic acid to provide immobilized nucleic acids.

In accordance with the methods provided herein, the cross-linking agent is selected to provide a high density of nucleic acids immobilized on the insoluble support. Without wishing to be bound by theory, it is believed that the high density of immobilized nucleic acids described herein is due, at least in part, to a relatively rapid reaction occurring between the cross-linking agent and the nucleic acid (e.g., a thiol-modified nucleic acid), compared to other reactions previously used to immobilize nucleic acids. In addition, high density may at least in part be due to a close spacing of the reactive groups (e.g., amino groups of other reactive functionality) on the functionalized insoluble support. Thus, reagents for modifying the surface will generally be selected to provide closely-spaced functionalities on the functionalized support. The cross-linking agent (and other reagents used to functionalize the support surface or the nucleic acid molecule) can be selected to provide any desired spacing of the immobilized nucleic acid molecules from the support surface, and to provide any desired spacing of the immobilized nucleic acids from each other. Thus, steric encumbrance of the nucleic acid molecules can be reduced or eliminated by choice of an appropriate cross-linking agent. In certain embodiments, the cross-linking reagent can be selected to provide multiple reactive functionalities as used in dendrimer synthesis for attachment of multiple nucleic acids to a single cross-linking moiety. Preferably, the cross-linking agent is selected to be highly reactive with the nucleic acid molecule, to provide rapid, complete, and/or selective reaction. In preferred embodiments, the reaction volume of the reagents (e.g., the thiol group and the thiol-reactive functionality) is small.

Nucleic Acids and Linkers

Preferred nucleic acids for use herein are "thiol-modified nucleic acids," i.e., nucleic acids derivatized to contain at least one reactive thiol moiety. As described in further detail in Example 1, below, nucleic acids containing at least one reactive thiol are preferably made by treating a nucleic acid containing a 3' or 5' disulfide with akreducing agent, which preferably will not compete in subsequent reactions (i.e. will not react with an iodoacetimido functionality. Disulfide-derivatized nucleic acids can be synthesized according to a variety of methods. For example, a nucleic acid can be modified at the 3'- or 5'-terminus by reaction with a disulfide-containing modifying a reagent. Alternatively, a thiolated primer can by enzymatically or non-enzymatically attached to the nucleic acid. A 5'-phosphoramidate functionality can also provide an attachment point for a thiol or disulfide-containing y osine or deoxycytosine. Examples of reducing agents appropriate for reduction of a disulfide-modified nucleic acid include: tris-(2-carboxyethyl) phosphine (TCEP) (preferably a concentration in the range of 1–100 mM (most preferably about 10 mM)) is reacted at a pH in the range of 3–6 (most preferably about 4.5), a temperature in the range of 20–45° C. (most preferably about 37° C.) for a time period in the range of about 1 to about 10 hrs (most preferably for about 5 hrs); dithiothreitol (preferably a concentration in the range of 25 to 100 mM (depending on whether the reactant is isolated) is reacted at a pH in the range of 6–10 (most preferably about 8) and at a temperature in the range of 25–45° C. (most preferably about 37° C.)) for a time in the range of about 1 to about 10 hrs (most preferably about 5 hrs). TCE provides an advantage in the low pH at which it is reactive. This low pH effectively protonates thiols, thus suppressing nucleophilic reactions of thiols and resulting in fewer side reactions than with other disulfide reducing agents which are employed at higher pH.

As further described in Example 1, below, a preferred bifunctional cross-linking agent is N-succinimidyl(4-iodoacetyl) aminobenzoate (SIAB). Other crosslinking agents include, but are not limited to, dimaleimide, dithio-bis-nitrobenzoic acid (DTNB), N-succinimidyl-S-acetyl-thioacetate (SATA), N-succinimidyl-3-(2-pyridyldithio propionate (SPDP), succinimidyl 4-(N-maleimidomethyl) cyclohexane-1-carboxylate (SMCC) ad 6-hydrazinonicotimide (HYNIC) may also be used in the novel process. For further examples of cross-linking reagents, see, e.g., Wong "Chemistry of Protein Conjugation and Cross-Linking," CRC Press (1991), and Hermanson, "Bioconjugate Techniques" Academic Press (1995).

In preferred embodiments, the nucleic acid is immobilized using the photocleavable linker moiety that is cleaved during mass spectrometry. Exemplary photolabile cross-linker include, but are not limited to, 3-amino-(2-nitrophenyl)propionic acid (Brown et al. (1995) *Molecular Diversity*, pp.4–12 and Rothschild et. al. (1996) *Nucleic Acids Res.* 24:361–66).

In a further embodiment of the methods of detecting alterations in a target nucleic acid sequence provided herein and methods of immobilization, a single-stranded nucleic acid complementary to the target nucleic acid is immobilized to a surface through a linkage that includes a thiol group-thiol reactive functionality bond and a cleavable, preferably a selectively cleavable, linker moiety.

Linkers

A target detection site can be directly linked to a solid support via a reversible or irreversible bond between an appropriate functionality (L') on the target nucleic acid molecule (T) and an appropriate functionality (L) on the capture molecule. A reversible linkage can be such that it is cleaved under the conditions of mass spectrometry (i.e., a photocleavable bond such as a charge transfer complex or a labile bond being formed between relatively stable organic radicals).

Photocleavable linkers are linkers that are cleaved upon exposure to light (see, e.g., Goldmacher et al. (1992) *Biocone. Chem.* 3:104–107), thereby releasing the targeted agent upon exposure to light. Photocleavable linkers that are cleaved upon exposure to light are known (see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methyl-rhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages), thereby releasing the targeted agent upon exposure to light. In preferred embodiments, the nucleic acid is immobilized using the photocleavable linker moiety that is cleaved during mass spectrometry.

Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

Thus, the L–L' chemistry can be of a type of disulfide bond (chemically cleavable, for example, by mercaptoethanol or dithioerythrol), a biotin/streptavidin system, a heterobifunctional derivative of a trityl ether group (see, e.g., K öster et al. (1990) "A Versatile Acid-Labile Linker for Modification of Synthetic Biomolecules," *Tetrahedron Letters* 31:7095) that can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase, or a ribonucleotide bond in between the oligodeoxynucleotide sequence, which can be cleaved, for example, by a ribonuclease or alkali.

The functionalities, L and L,' can also form a charge transfer complex and thereby form the temporary L–L' linkage. Since in many cases the "charge-transfer band" can be determined by UV/vis spectrometry (see, e.g., *Organic*

*Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L–L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g., *Reactive Molecules* by C. Wentrup, John Wiley & Sons, 1984).

When performing exonuclease sequencing using MALDI-TOF MS, a single stranded DNA molecule immobilized via its 5'-end to a solid support is unilaterally degraded with a 3'-processive exonuclease and the molecular weight of the degraded nucleotide is determined sequentially. Reverse Sanger sequencing reveals the nucleotide sequence of the immobilized DNA. By adding a selectively cleavable linker, not only can the mass of the free nucleotides be determined but also, upon removal of the nucleotides by washing, the mass of the remaining fragment can be detected by MALDI-TOF upon cleaving the DNA from the solid support. Using selectively cleavable linkers, such as the photocleavable and chemical cleavable linkers provided herein, this cleavage can be selected to occur during the ionization and volatizing steps of MALDI-TOF. The same rationale applies for a 5' immobilized strand of a double stranded DNA that is degraded while in a duplex. Likewise, this also applies when using a 5'-processive exonuclease and the DNA is immobilized through the 3'-end to the solid support.

As noted, at least three version of immobilization are contemplated herein: 1) the target nucleic acid is amplified or obtained (the target sequence or surrounding DNA sequence must be known to make primers to amplify or isolated); 2) the primer nucleic acid is immobilized to the solid support and the target nucleic acid is hybridized thereto (this is for detecting the presence of or sequencing a target sequence in a sample); or 3) a double stranded DNA (amplified or isolated) is immobilized through linkage to one predetermined strand; the DNA is denatured to eliminate the duplex and then a high concentration of a complementary primer or DNA with identity upstream from the target site is added and a strand displacement occurs and the primer is hybridized to the immobilized strand.

In the embodiments where the primer nucleic acid is immobilized on the solid support and the target nucleic acid is hybridized thereto, the inclusion of the cleavable linker allows the primer DNA to be immobilized at the 5'-end so that free 3'-OH is available for nucleic acid synthesis (extension) and the sequence of the "hybridized" target DNA can be determined because the hybridized template can be removed by denaturation and the extended DNA products cleaved from the solid support for MALDI-TOF MS. Similarly for 3), the immobilized DNA strand can be elongated when hybridized to the template and cleaved from the support. Thus, Sanger sequencing and primer oligo base extension (PROBE), discussed below, extension reactions can be performed using an immobilized primer of a known, upstream DNA sequence complementary to an invariable region of a target sequence. The nucleic acid from the person is obtained and the DNA sequence of a variable region (deletion, insertion, missense mutation that cause genetic predisposition or diseases, or the presence of viral/bacterial or fungal DNA) not only is detected, but the actual sequence and position of the mutation is also determined.

In other cases, the target DNA must be immobilized and the primer annealed. This requires amplifying a larger DNA based on known sequence and then sequencing the immobilized fragments (i.e., the extended fragments are hybridized but not immobilized to the support as described above). In these cases, it is not desirable to include a linker because the MALDI-TOF spectrum is of the hybridized DNA; it is not necessary to cleave the immobilized template.

Any linker known to those of skill in the art for immobilizing nucleic acids to solid supports may be used herein to link the nucleic acid to a solid support. The preferred linkers herein are the selectively cleavable linkers, particularly those exemplified herein. Other linkers include, acid cleavable linkers, such as bismaleimideothoxy propane, acid-labile trityl linkers.

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) *Infection & Immun.* 60:584–589) and acid labile transfering conjugates that contain a sufficient portion of transferrin to permit entry into the intracellular transferrin cycling pathway (see, e., Welhöner et al. (1991) *J. Biol. Chem.* 266:4309–4314).

Photocleavable Linkers

Photocleavable linkers are provided. In particular, photocleavable linkers as their phosphoramidite derivatives are provided for use in solid phase synthesis of oligonucleotides. The linkers contain o-nitrobenzyl moieties and phosphate linkages which allow for complete photolytic cleavage of the conjugates within minutes upon UV irradiation. The UV wavelengths used are selected that the irradiation will not damage the oligonucleotides and are preferably about 350–380 nm, more preferably 365 nm. The photocleavable linkers provided herein possess comparable coupling efficiency as compared to commonly used phosphoramidite monomers (see, Sinha et al. (1983) *Tetrahedron Lett.* 24:5843–5846; Sinha et al. (1984) *Nucleic Acids Res.* 12:4539–4557; Beaucage et al. (1993) *Tetrahedron* 49:6123–6194; and Matteucci et al. (1981) *J. Am. Chem. Soc.* 103:3185–3191).

In one embodiment, the photocleavable linkers have formula I:

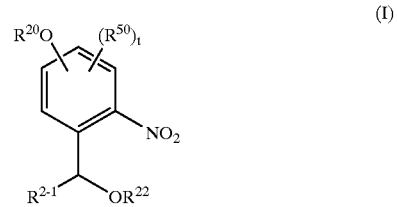

where $R^{20}$ is w-(4,4'-dimethoxytrityloxy)alkyl or w-hydroxyalkyl; $R^{21}$ is selected from hydrogen, alkyl, aryl, alkoxycarbonyl, aryloxycarbonyl and carboxy; $R^{22}$ is hydrogen or (dialkylamino)(w-cyanoalkoxy)P-; t is 0–3; and $R^{50}$ is alkyl, alkoxy, aryl or aryloxy.

In a preferred embodiment, the photocleavable linkers have formula II:

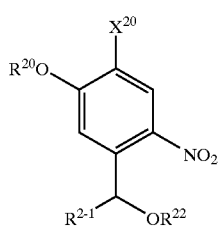

where $R^{20}$ is w-(4,4'-dimethoxytrityloxy)alkyl, w-hydroxyalkyl or alkyl; $R^{21}$ is selected from hydrogen, alkyl, aryl, alkoxycarbonyl, aryloxycarbonyl and carboxy; $R^{22}$ is hydrogen or (dialkylamino)(w-cyanoalkoxy)P-; and $X^{20}$ is hydrogen, alkyl or $OR^{20}$.

In particularly preferred embodiments, $R^{20}$ is 3-(4,4'-dimethoxytrityloxy)propyl, 3-hydroxypropyl or methyl; $R^{21}$ is selected from hydrogen, methyl and carboxy; $R^{22}$ is hydrogen or (diisopropylamino)(2-cyanoethoxy)P-; and $X^{20}$ is hydrogen, methyl or $OR^{20}$. In a more preferred embodiment, $R^{20}$ is 3-(4,4'-dimethoxytrityloxy)propyl; $R^{21}$ is methyl; $R^{22}$ is (diisopropylamino)(2-cyanoethoxy)P-; and $X^{20}$ is hydrogen. In another more preferred embodiment, $R^{20}$ is methyl; $R^{21}$ is methyl; $R^{22}$ is (diisopropylamino)(2-cyanoethoxy)P-; and $X^{20}$ is 3-(4,4'-dimethoxytrityloxy)propoxy.

In another embodiment, the photocleavable linkers have formula III

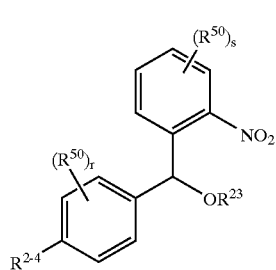

where $R^{23}$ is hydrogen or (dialkylamino)(w-cyanoalkoxy) P-; and $R^{24}$ is selected from w-hydroxyalkoxy, w-(4,4'-dimethoxytrityloxy)alkoxy, w-hydroxyalkyl and w-(4,4'-dimethoxytrityloxy)alkyl, and is unsubstituted or substituted on the alkyl or alkoxy chain with one or more alkyl groups; r and s are each independently 0–4; and $R^{50}$ is alkyl, alkoxy, aryl or aryloxy. In certain embodiments, $R^{24}$ is w-hydroxyalkyl or w-(4,4'-dimethoxytrityloxy)alkyl, and is substituted on the alkyl chain with a methyl group.

In preferred embodiments, $R^{23}$ is hydrogen or (diisopropylamino)(2-cyanoethoxy)P-; and $R^{24}$ is selected from 3-hydroxypropoxy, 3-(4,4'-dimethoxytrityloxy) propoxy, 4-hydroxybutyl, 3-hydroxy-1-propyl, 1-hydroxy-2-propyl, 3-hydroxy-2-methyl-1-propyl, 2-hydroxyethyl, hydroxymethyl, 4-(4,4'-dimethoxytrityloxy)buty), 3-(4,4'-dimethoxytrityloxy)-1-propyl, 2-(4,4'-dimethoxytrityloxy) ethyl, 1-(4,4'-dimethoxytrityloxy)-2-propyl, 3-(4,4'-dimethoxytriyioxy)-2-methyl-1-propyl and 4,4'-dimethyoxytrityloxymethyl.

In more preferred embodiments, $R^{23}$ is (diisopropylamino)(2-cyanoethoxy)P-; r and s are 0; and $R^{24}$ is selected from 3-(4,4'-dimethoxytrityloxy)propoxy, 4-(4, 4'-dimethoxytrityloxy)butyl, 3-(4,4'-dimethoxytrityloxy) propyl, 2-(4,4'-dimethoxytrityloxy)ethyl, 1-(4,4'-dimethoxytrityloxy)-2-propyl, 3-(4,4'-dimethoxytriyloxy)-2-methyl-1-propyl and 4,4'-dimethyoxytrityloxymethyl. $R^{24}$ is most preferably 3-(4,4'-dimethoxytrityloxy)propoxy.

Preparation of the Photocleavable Linkers

A. Preparation of Photocleavable Linkers of Formulae I or II

Photocleavable linkers of formulae I or II may be prepared by the methods described below, by minor modification of the methods by choosing the appropriate starting materials or by any other methods known to those of skill in the art.

In the photocleavable linkers of formula it where $X^{20}$ is hydrogen, the linkers may be prepared in the following manner. Alkylation of 5-hydroxy-2-nitrobenzaldehyde with an w-hydroxyalkyl halide, e.g., 3-hydroxypropyl bromide, followed by protection of the resulting alcohol as, e.g., a silyl ether, provides a 5-(w-silyloxyalkoxy)-2-nitrobenzaldehyde. Addition of an organometallic to the aldehyde affords a benzylic alcohol. Organometallics which may be used include trialkylaluminums (for linkers where $R^{21}$ is alkyl), such as trimethylaluminum, borohydrides (for linkers where $R^{21}$ is hydrogen), such as sodium borohydride, or metal cyanides (for linkers where $R^{21}$ is carboxy or alkoxycarbonyl), such as potassium cyanide. In the case of the metal cyanides, the product of the reaction, a cyanohydrin, would then be hydrolyzed under either acidic or basic conditions in the presence of either water or an alcohol to afford the compounds of interest.

The silyl group of the side chain of the resulting benzylic alcohols may then be exchanged for a 4,4'-dimethoxytriyl group by desilylation with, e.g., tetrabutylammonium fluoride, to give the corresponding alcohol, followed by reaction with 4,4'-dimethoxytrityl chloride. Reaction with, e.g., 2-cyanoethyl diisopropylchlorophosphoramidite affords the linkers where $R^{22}$ is (dialkylamino)(w-cyanoalkoxy)P-.

A specific example of a synthesis of a photocleavable linker of formula II is shown in the following scheme, which also demonstrates use of the linker in oligonucleotide synthesis. This scheme is intended to be illustrative only and in no way limits the scope of the invention. Experimental details of these synthetic transformations are provided in the Examples.

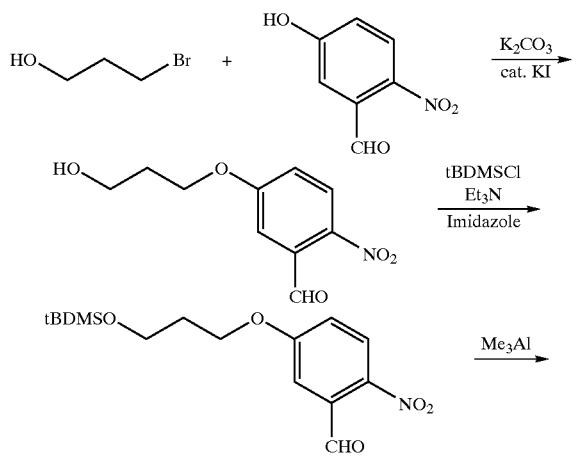

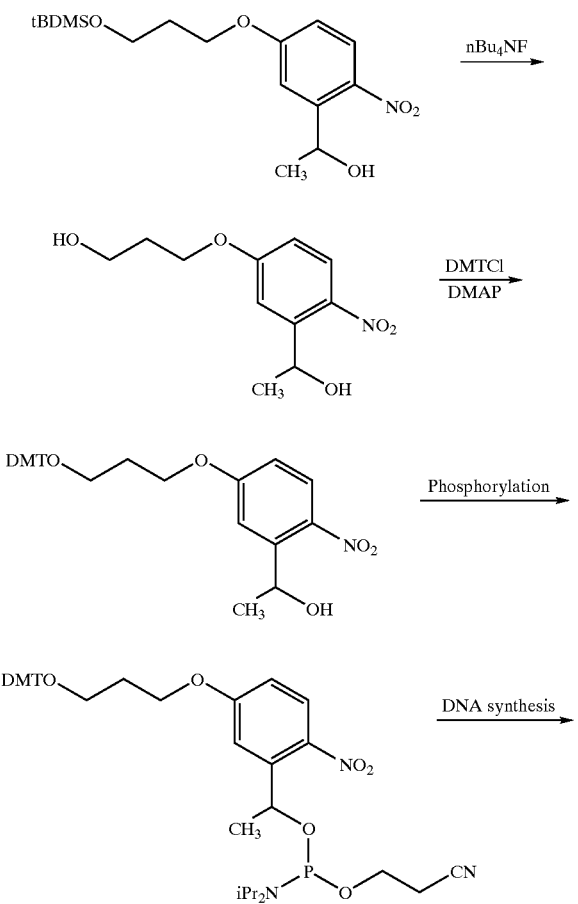

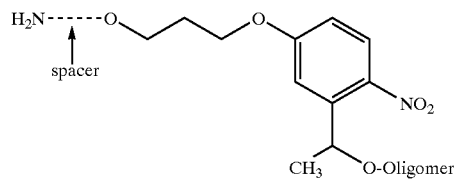

Synthesis of the linkers of formula II where $X^{20}$ is $OR^{20}$, 3,4-dihydroxyacetophenone is protected selectively at the 4-hydroxyl by reaction with, e.g., potassium carbonate and a silyl chloride. Benzoate esters, propiophenones, butyrophenones, etc. may be used in place of the acetophenone. The resulting 4-silyloxy-3-hydroxyacetophenone is then alkylated at the with an alkyl halide (for linkers where $R^{20}$ is alkyl) at the 3-hydroxyl and desilated with, e., tetrabutylammonium fluoride to afford a 3-alkoxy-4-hydroxyacetophenone. This compound is then alkylated at the 4-hydroxyl by reaction with an w-hydroxyalkyl halide, e.g., 3-hydroxypropyl bromide, to give a 4-(w-hydroxyalkoxy)-3-alkoxyacetophenone. The side chain alcohol is then protected as an ester, e.g., an acetate. This compound is then nitrated at the 5-position with, e.g., concentrated nitric acid to provide the corresponding 2-nitroacetophenones. Saponification of the side chain ester with, e.g., potassium carbonate, and reduction of the ketone with, e.g., sodium borohydride, in either order gives a 2-nitro-4-(w-hydroxyalkoxy)-5-alkoxybenzylic alcohol.

Selective protection of the side chain alcohol as the corresponding 4,4'-dimethoxytrityl ether is then accomplished by reaction with 4,4'-dimethoxytrityl chloride. Further reaction with, e.g., 2-cyanoethyl diisopropylchlorophosphoramidite affords the linkers where $R^{22}$ is (dialkylamino)(w-cyanoalkoxy)P-.

A specific example of the synthesis of a photocleavable linker of formula II is shown the following scheme. This scheme is intended to be illustrative only and in no way limit the scope of the invention. Detailed experimental procedures for the transformations shown are found in the Examples.

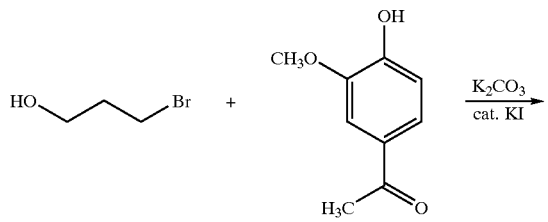

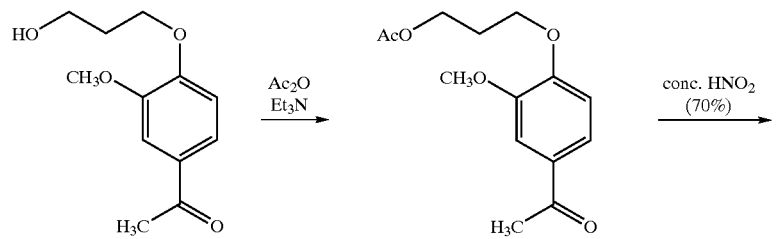

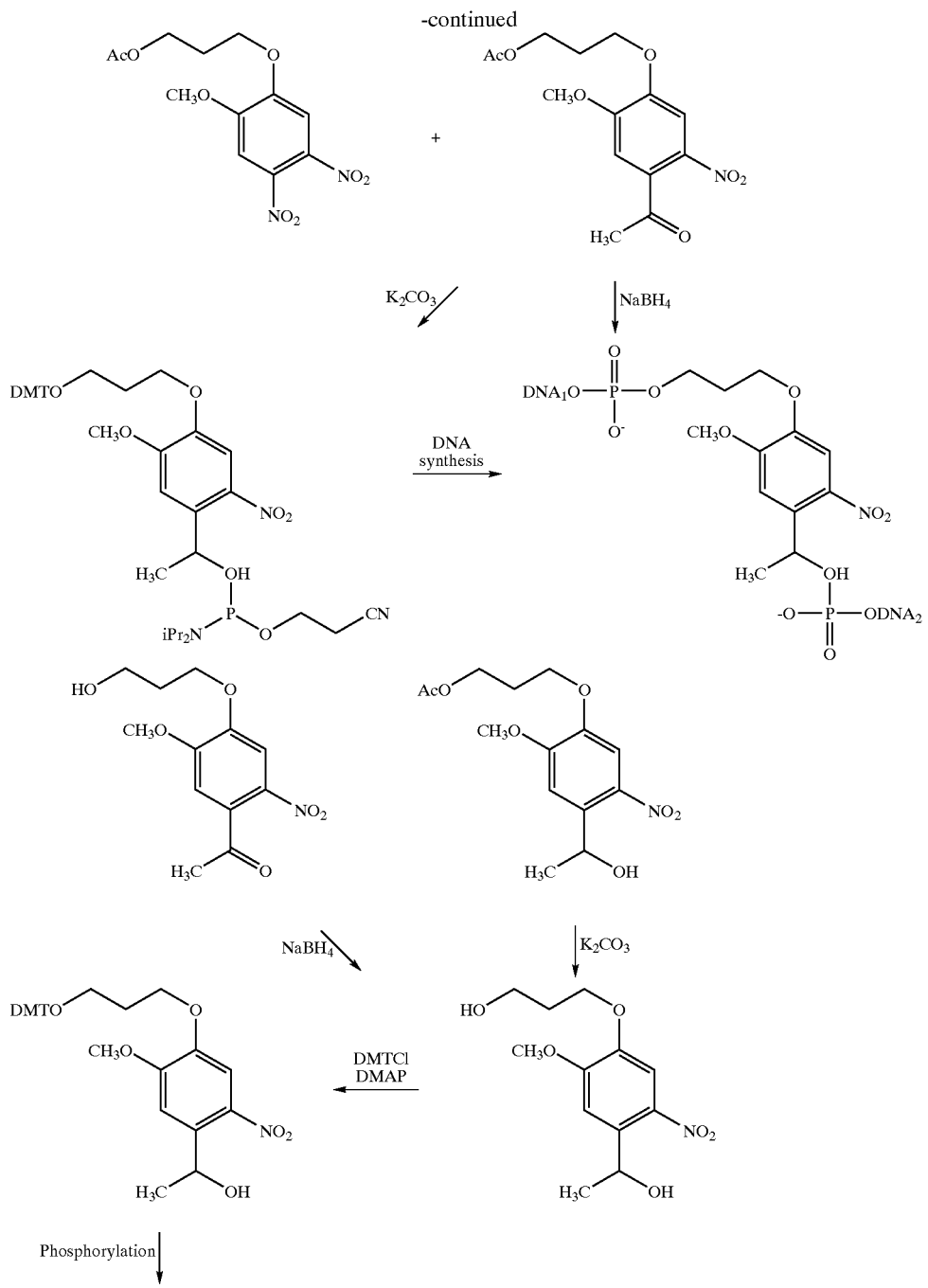

B. Preparation of Photocleavable Linkers of Formula III

Photocleavable linkers of formula III may be prepared by the methods described below, by minor modification of the methods by choosing appropriate starting materials, or by other methods known to those of skill in the art.

In general, photocleavable linkers of formula III are prepared from w-hydroxyalkyl- or alkoxyaryl compounds, in particular w-hydroxy-alkyl or alkoxy-benzenes. These compounds are commercially available, or may be prepared from an w-hydroxyalkyl halide (e.g., 3-hydroxypropyl bromide) and either phenyllithium (for the w-hydroxyalkylbenzenes) or phenol (for the w-hydroxyalkoxybenzenes). Acylation of the w-hydroxyl group (e.g., as an acetate ester) followed by Friedel-Crafts acylation of the aromatic ring with 2-nitrobenzoyl chloride provides a 4-(w-acetoxy-alkyl or alkoxy)-2-nitrobenzophenone. Reduction of the ketone with, e.g., sodium borohydride, and saponification of the side chain ester are performed in either order to afford a 2-nitrophenyl-4-(hydroxy-alkyl or alkoxy)phenylmethanol. Protection of the terminal hydroxyl group as the corresponding 4,4'-dimethoxytrityl ether is achieved by reaction with 4,4'-dimethoxytrityl chloride. The benzylic hydroxyl group is then reacted with, e.g., 2-cyanoethyl diisopropylchlorophosphoramidite to afford linkers of formula II where $R^{23}$ is (dialkylamino)(w-cyanoalkoxy)P-. Other photocleavable linkers of formula III may be prepared by substituting 2-phenyl-1-propanol or 2-phenylmethyl-1-propanol for the ω-hydroxy-alkyl or alkoxy-benzenes in the above synthesis. These compounds are commercially available, but may also be prepared by reaction of, e.g., phenylmagnesium bromide or benzylmagnesium bromide, with the requisite oxirane (i.e., propylene oxide) in the presence of catalytic cuprous ion.

Chemically Cleavable Linkers

A variety of chemically cleavable linkers may be used to introduce a cleavable bond between the immobilized nucleic acid and the solid support. Acid-labile linkers are presently preferred chemically cleavable linkers for mass spectrometry, especially MALDI-TOF MS, because the acid labile bond is cleaved during conditioning of the nucleic acid upon addition of the 3-HPA matrix solution. The acid labile bond can be introduced as a separate linker group, e.g., the acid labile trityl groups or may be incorporated in a synthetic nucleic acid linker by introducing one or more silyl internucleoside bridges using diisopropylsilyl, thereby forming diisopropylsilyl-linked oligonucleotide analogs. The diisopropylsilyl bridge replaces the phoshodiester bond in the DNA backbone and under mildly acidic conditions, such as 1.5% trifluoroacetic acid (TFA) or 3-HPA/1% TFA MALDI-TOF matrix solution, results in the introduction of one or more intra-strand breaks in the DNA molecule. Methods for the preparation of diisopropylsilyl-linked oligonucleotide precursors and analogs are known to those of skill in the art (see e.g., Saha et al. (1993) *J. Org. Chem.* 58:7827–7831). These oligonucleotide analogs may be readily prepared using solid state oligonucleotide synthesis methods using diisopropylsilyl derivatized deoxyribonucleosides.

Mass Modification of Nucleic Acids

In certain embodiments, nucleic acids modified at positions other than the 3'- or 5'-terminus can be used. Modification of the sugar moiety of a nucleotide at positions other than the 3' and 5' position is possible through conventional methods. Also, nucleic acid bases can be modified, e.g., by modification of C-5 of dT with a linker arm, e.g., as described in F. Eckstein, ed., *"Oligonucleotides and Analogues: A Practical Approach,"* IRL Press (1991). Such a linker arm can be modified to include a thiol moiety. Alternatively, backbone-modified nucleic acids (e.g., phosoroamidate DNA) can be used so that the thiol group can be attached to the nitrogen center provided by the modified phosphate backbone.

In preferred embodiments, modification of a nucleic acid, e.g., as described above, does not substantially impair the ability of the nucleic acid or nucleic sequence to hybridize to its complement. Thus, any modification should preferably avoid substantially modifying the functionalities of the nucleic acid which are responsible for Watson-Crick base pairing. The nucleic acid can be modified such that a non-terminal thiol group is present, and the nucleic acid, when immobilized to the support, is capable of self-complementary base pairing to form a "hairpin" structure having a duplex region.

Solid Supports and Substrates

Examples of insoluble supports and substrates for use herein include, but are not limited to, beads (silica gel, controlled pore glass, magnetic beads, Sephadex/Sepharose beads, cellulose beads, etc.), capillaries, flat supports such as glass fiber filters, glass surfaces, metal surfaces (steel, gold, silver, aluminum, silicon and copper), plastic materials including multiwell plates or membranes (e.g., of polyethylene, polypropylene, polyamide, polyvinyldenedifluoride), wafers, combs, pins (e.g., arrays of pins suitable for combinatorial synthesis or analysis) or beads in pits of flat surfaces such as wafers (e.g., silicon wafers), with or without filter plates.

Mass Spectrometry

Once immobilized, the nucleic acids can be analyzed by any of a variety of means including, for example, spectrometric techniques such as UV/VIS, IR, fluorescence, chemiluminescence, or NMR spectroscopy, mass spectrometry, or other methods know in the art, or combinations thereof. Preferred mass spectrometer formats include the ionization (I) techniques, such as matrix assisted laser desorption (MALDI), continuous or pulsed electrospray (ESI) and related methods (e.g. Ionspray or Thermospray), or massive cluster impact (MCI); these ion sources can be matched with detection formats including linear or reflectron time-of-flight (TOF), single or multiple quadruple, single or multiple magnetic sector, Fourier Transform ion cyclotron resonance (FTICR), ion trap, and combinations thereof to yield a hybrid detector (e.g., ion-trap/time-of-flight). For ionization, numerous matrix/wavelength combinations (MALDI) or solvent combinations (ESI) can be employed.

Preparation of DNA Arrays

Methods and systems for preparing arrays of sample material for analysis by a diagnostic tool are provided herein. For example, FIG. 1 illustrates one system for preparing arrays of sample material for analysis by a diagnostic tool. FIG. 1 depicts a system 10 that includes a data processor 12, a motion controller 14, a robotic arm assembly 16, a monitor element 18A, a central processing unit 18B, a microliter plate of source material 20, a stage housing 22, a robotic arm 24, a stage 26, a pressure controller 28, a conduit 30, a mounting assembly 32, a pin assembly 38, and substrate elements 34. In the view shown by FIG. 1, it is also illustrated that the robotic assembly 16 can include a moveable mount element 40 and a horizontal slide groove 42. The robotic arm 24 can optionally pivot about a pin 36 to increase the travel range of the arm 24 so that arm 24 can disposes the pin assembly 38 above the source plate 20.

The data processor 12 depicted in FIG. 1 can be a conventional digital data processing system such as an IBM PC compatible computer system that is suitable for processing data and for executing program instructions that will provide information for controlling the movement and operation of the robotic assembly 16. It will be apparent to one skilled in the art that the data processor unit 12 can be any type of system suitable for processing a program of instructions signals that will operate the robotic assembly that is integrated into the robotic housing 16. Optionally the data processor 12 can be a micro-controlled assembly that is integrated into robotic housing 16. In further alternative embodiments, the system 10 need not be programmable and can be a singleboard computer having a firmware memory for storing instructions for operating the robotic assembly 16.

In the embodiment depicted in FIG. 1, there is a controller 14 that electronically couples between the data processor 12 and the robotic assembly 16. The depicted controller 14 is a motion controller that drives the motor elements of the robotic assembly 16 for positioning the robotic arm 24 at a selected location. Additionally, the controller 14 can provide instructions to the robotic assembly 16 to direct the pressure controller 28 to control the volume of fluid ejected from the individual pin elements of the depicted pin assembly 38. The design and construction of the depicted motion controller 14 follows from principles well known in the art of electrical engineering, and any controller element suitable for driving the robotic assembly 16 can be practiced without departing from the scope thereof.

The robotic assembly 16 depicted in FIG. 1 electronically couples to the controller 14. The depicted robotic assembly 16 is a gantry system that includes an XY table for moving the robotic arm about a XY plane, and further includes a Z axis actuator for moving the robotic arm orthogonally to that XY plane. The robotic assembly 16 depicted in FIG. 1 includes an arm 24 that mounts to the XY stage which moves the arm within a plane defined by the XY access. In the depicted embodiment, the XY table is mounted to the Z actuator to move the entire table along the Z axis orthogonal to the XY plane. In this way, the robotic assembly provides three degrees of freedom that allows the pin assembly 38 to be disposed to any location above the substrates 34 and the source plate 20 which are shown in FIG. 1 as sitting on the stage 26 mounted to the robotic assembly 16.

The depicted robotic assembly 16 follows from principles well known in the art of electrical engineering and is just one example of a robotic assembly suitable for moving a pin assembly to locations adjacent a substrate and source plate such as the depicted substrate 34. Accordingly, it will be apparent to one of ordinary skill in the art that alternative robotic systems can be practiced following the descriptions herein without departing from the scope thereof.

FIG. 1 depicts an embodiment of a robotic assembly 16 that includes a pressure controller 28 that connects via a conduit 30 to the mount 32 that connects to the pin assembly 38. In this embodiment the mount 32 has an interior channel for fluidicly coupling the conduit 30 to the pin assembly 38. Accordingly, the pressure controller 28 is fluidicly coupled by the conduit 30 and the mount 32 to the pin assembly 38. In this way the controller 14 can send signals to the pressure controller 28 to control selectively a fluid pressure delivered to the pin assembly 38.

Figure 2:
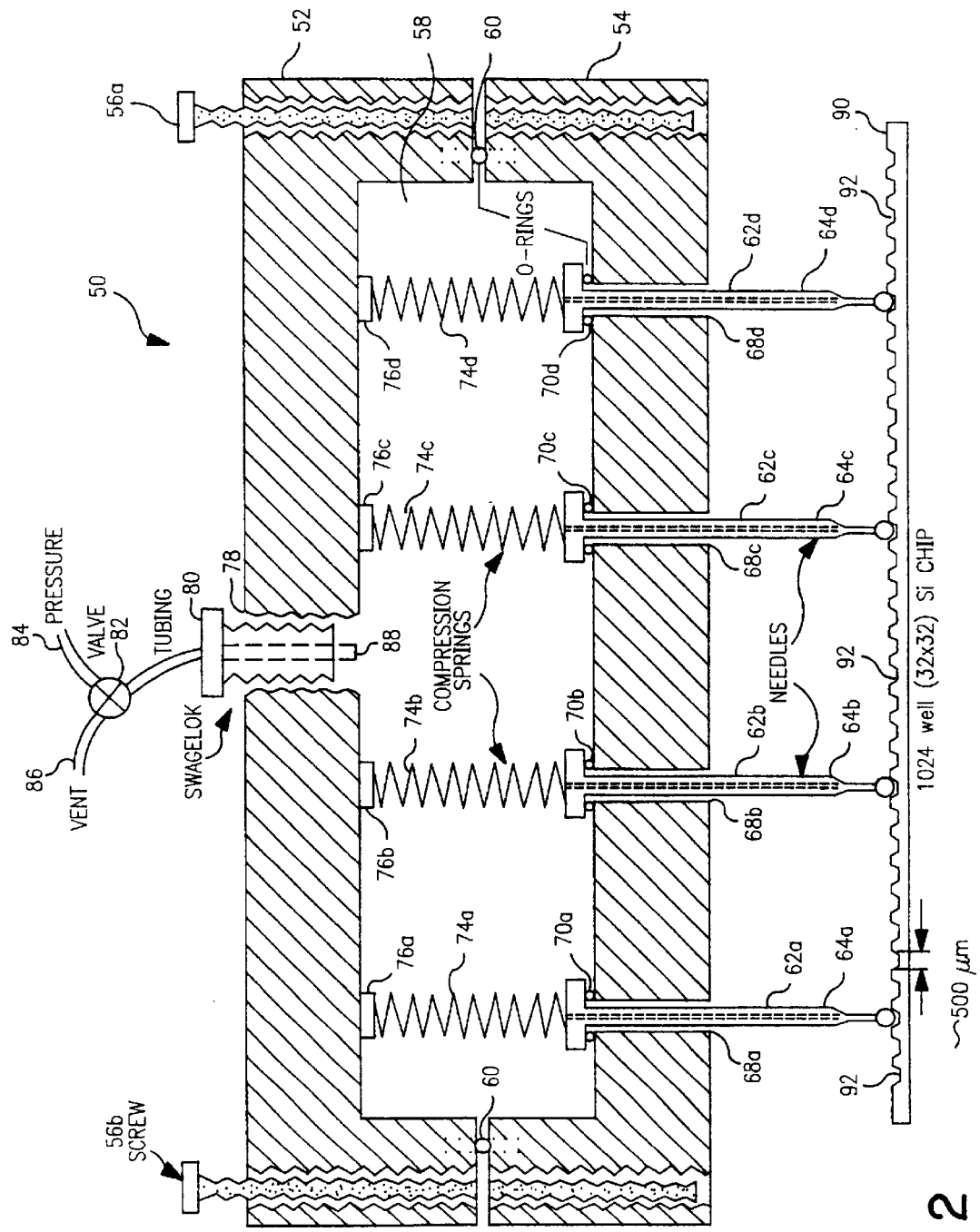
FIG. 2 illustrates a pin assembly suitable for use with the system depicted in FIG. 1 for implementing a parallel process of dispensing material to a surface of a substrate.

FIG. 2 depicts one embodiment of a pin assembly 50 suitable for practice with the system depicted in FIG. 1 which includes the pressure controller 28. In the depicted embodiment, the pin assembly 50 includes a housing formed from an portion 52 and a lower portion 54 that are joined together by the screws 56A and 56B to define an interior chamber volume 58. FIG. 2 further depicts that to fluidicly seal the interior chamber volume 58 the housing can include a seal element depicted in FIG. 2 as an O-ring gasket 60 that sits between the upper block and the lower block 54 and surrounds completely the perimeter of the interior chamber volume 58. FIG. 2 further depicts that the pin assembly 50 includes a plurality of vesicles 62A–62D, each of which include an axial bore extending therethrough to form the depicted holding chambers 64A–64D. Each of the depicted vesicles extends through a respective aperture 68A–68D disposed within the lower block 54 of the housing.

As further shown in the depicted embodiment, each of the vesicles 62A–62D has an upper flange portion that sits against a seal element 70A–70D to form a fluid-tight seal between the vesicle and the lower block 54 to prevent fluid from passing through the apertures 68A–68D. To keep the seal tight, the depicted pin assembly 50 further includes a set of biasing elements 74A–74D depicted in FIG. 2 as springs which, in the depicted embodiments, are in a compressed state to force the flange element of the vesicles 62A–62D against their respective seal elements 70A–70D. As shown in FIG. 2, the biasing elements 74A–74D extend between the vesicles and the upper block 52. Each of the springs 74A–74D can be fixedly mounted to a mounting pad 76A–76D where the spring elements can attach to the upper block 52. The upper block 52 further includes an aperture 78 depicted in FIG. 2 as a centrally disposed aperture that includes a threaded bore for receiving a swagelok 80 that can be rotatably mounted within the aperture 78.

As further depicted in FIG. 2, the swagelok 80 attaches by a conduit to a valve 82 than can connect the swagelok 80 to a conduit 84 that can be coupled to a pressure source, or alternatively can couple the swagelok 80 to a conduit 86 that provides for venting of the interior chamber 58. A central bore 88 extends through the swagelok 80 and couples to the tubing element which further connects to the valve 82 to thereby fluidicly and selectively couple the interior chamber volume 58 to either a pressure source, or a venting outlet.

The pin assembly 50 described above and depicted in FIG. 2 disposed above a substrate element 90 that includes a plurality of wells 92 that are etched into the upper surface of the substrate 90. As illustrated by FIG. 2, the pitch of the vesicles 62A–62D is such that each vesicle is spaced from the adjacent vesicles by a distance that is an integral multiple of the pitch distance between wells 92 etched into the upper surface of the substrate 90. As will be seen from the following description, this spacing facilitates the parallel dispensing of fluid, such that fluid can be dispensed into a plurality of wells in a single operation. Each of the vesicles can be made from stainless steel, silica, polymeric material or any other material suitable for holding fluid sample. In one example, 16 vesicles are employed in the assembly, which are made of hardened beryllium copper, gold plated over nickel plate. They are 43.2 mm long and the shaft of the vesicle is graduated to 0.46 mm outer diameter with a concave tip. Such a pin was chosen since the pointing accuracy can be approximately 501 micrometers. However, it will be apparent that any suitable pin style can be employed for the device, including but not limited to flat, star-shaped, concave, pointed solid, pointed semi-hollow, angled on one or both sides, or other such geometries.

Figure 3:
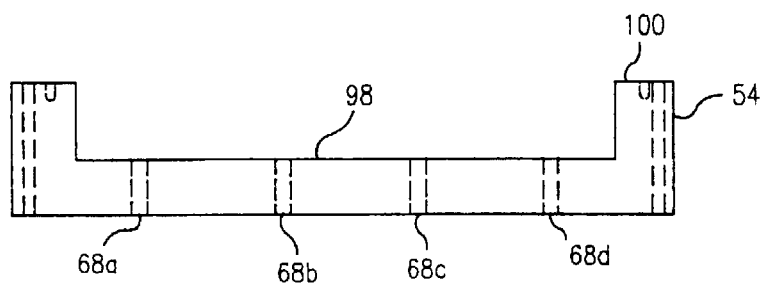
FIG. 3 depicts a bottom portion of the assembly shown in FIG. 2.

FIG. 3 shows from a side perspective the lower block 54 of the pin assembly 50 depicted in FIG. 2. FIG. 3 shows approximate dimensions for one pin assembly. As shown, the lower block 54 has a bottom plate 98 and a surrounding shoulder 100. The bottom plate 98 is approximately 3 mm in thickness and the shoulder 100 is approximately 5 mm in thickness.

Figure 4:
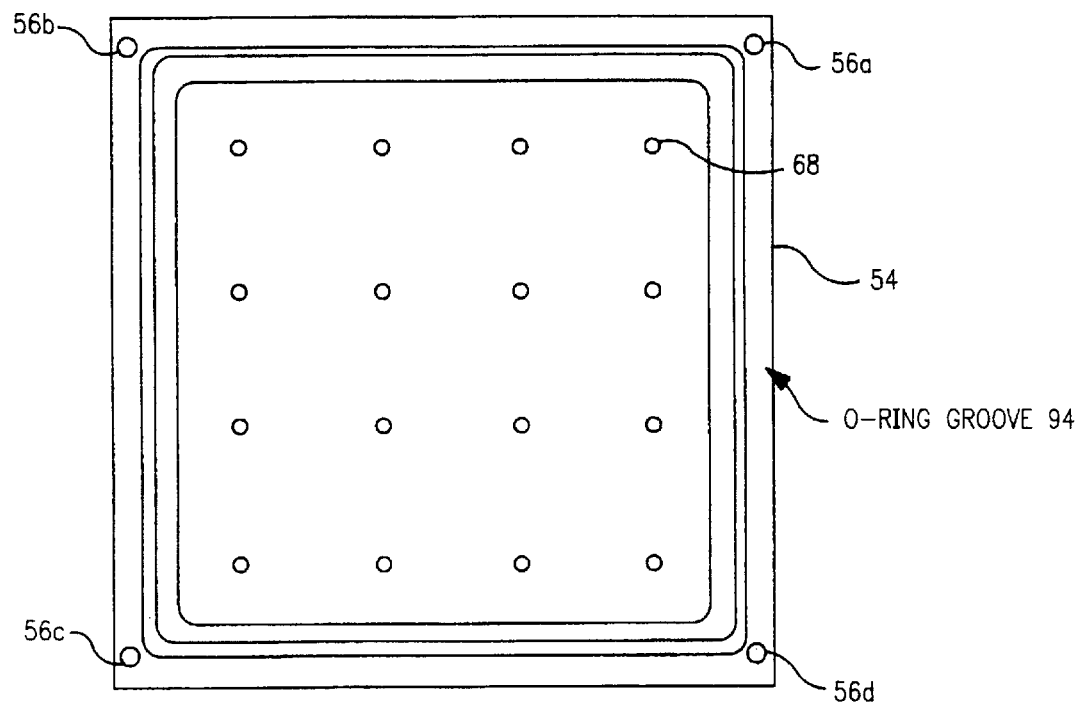
FIG. 4 depicts an alternative view of the bottom portion of the pin assembly depicted in FIG. 2.

FIG. 4 shows from an overhead perspective the general structure and dimensions for one lower block 54 suitable for use with the pin assembly for use with the pin assembly 50 shown in FIG. 2. As shown in FIG. 4, the lower block 54 includes a four-by-four matrix of apertures 68 to provide 16 apertures each suitable for receiving a vesicle. As described above with reference to FIG. 2, the spacing between the aperture 68 is typically an integral multiple of the distance between wells on a substrate surface as well as the wells of a source plate. Accordingly, a pin assembly having the lower block 54 as depicted in FIG. 4 can dispense fluid in up to 16 wells simultaneously. FIG. 4 also shows general dimensions of one lower block 54 such that each side of block 54 is generally 22 mm in length and the pitch between aperture 68 is approximately 4.5 mm. Such a pitch is suitable for use with a substrate where fluid is to be dispensed at locations approximately 500 $\mu$m apart, as exemplified by the substrate 90 of FIG. 2. FIG. 4 also shows that the lower block 54 can include an optional O-ring groove 94 adapted for receiving an O-ring seal element, such as the seal element 60 depicted in FIG. 2. It is understood that such a groove element 94 can enhance and improve the fluid seal formed by the seal element 60.

The pinblock can be manufactured of stainless steel as this material can be drilled accurately to about +25 µm, but a variety of probe materials can also be used, such as G10 laminate, PMMA or other suitable material. The pin block can contain any number of apertures and is shown with 16 receptacles which hold the 16 pins in place. To increase the pointing accuracy of each pin, an optional alignment place can be placed below the block so that about 6 mm of the pin tip is left exposed to enable dipping into the wells of a microtiter plate. The layout of the probes in the depicted tool is designed to coordinate with a 384-well microtiter plate, thus the center-to-center spacing of the probes in 4.5 mm. An array of 4×4 probes was chosen since it would produce an array that would fit in less than one square inch, which is the travel range of an xy stage of a MALDI TOF MS employed by the assignee. The pintool assembly is completed with a stainless steel cover on the top side of the device which is then attached onto the Z-arm of the robot.

With references to FIG. 1, the robotic assembly 16 employs a pin tool assembly 38 that is configured similarly as the pin tool assembly 50 depicted in FIG. 2. The pressure controller 28 selectively controls the pressure within chamber 58. With this embodiment, a control program operates on the data processor 12 to control the robotic assembly 16 in a way that the assembly 16 prints an array of elements on the substrates 34.

Figure 5A:
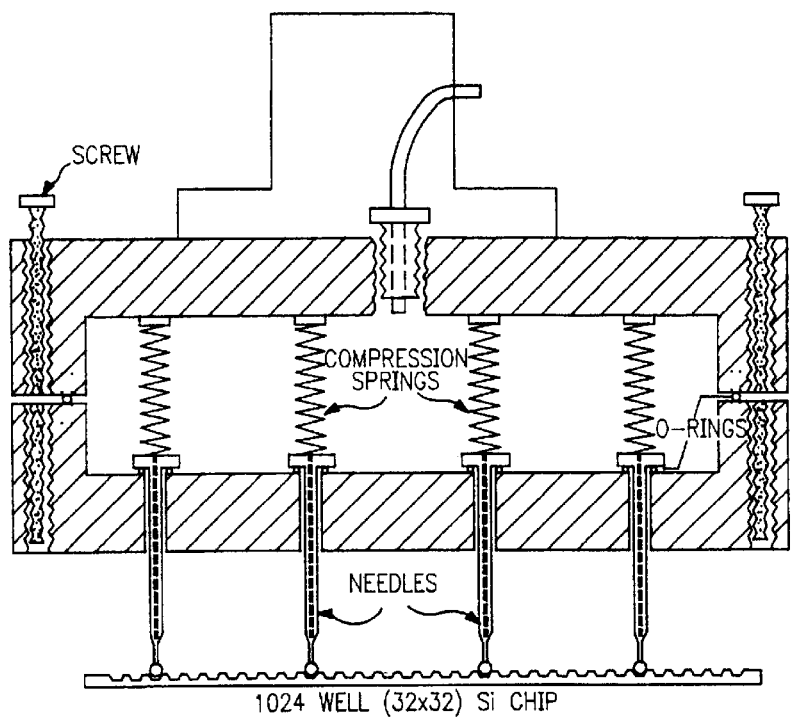
FIGS. 5A–5D depict a method for preparing an array of sample material.

In a first step, FIG. 5A, the program can direct the robotic assembly 16 to move the pin assembly 38 to be disposed above the source plate 20. The robotic assembly 16 will then dip the pin assembly into the source plate 20 which can be a 384 well DNA source plate. As shown in FIG. 4 the pin assembly can include 16 different pins such that the pin assembly 50 will dip 16 pins into different 16 wells of the 384 well DNA source plate 20. Next the data processor 12 will direct the motion controller 14 to operate the robotic assembly 16 to move the pin assembly to a position above the surface of the substrate 34. The substrate 34 can be any substrate suitable for receiving a sample of material and can be formed of silicon, plastic, metal, or any other such suitable material. Optionally the substrate will have a flat surface, but can alternatively include a pitted surface, a surface etched with wells or any other suitable surface typography. The program operating on data processor 12 can then direct the robotic assembly, through the motion controller 14, to direct the pressure controller 28 to generate a positive pressure within the interior chamber volume 58. In this practice, the positive interior pressure will force fluid from the holding chambers of vesicles 62 to eject fluid from the vesicles and into a respective well 92 of the substrate 90.

The program operating on data processor 12 can also direct the controller 14 to control the pressure controller 28 to control filling the holding chambers with source material from the source plate 20. The pressure controller 28 can generate a negative pressure within the interior chamber volume 58 of the pin assembly. This will cause fluid to be drawn up into the holding chambers of the vesicles 62A–62D. The pressure controller 28 can regulate the pressure either by open-loop or closed-loop control to avoid having fluid overdrawn through the holding chambers and spilled into the interior chamber volume 58. Loop control systems for controlling pressure are well known in the art and any suitable controller can be employed. Such spillage could cause cross-contamination, particularly if the source material drawn from the source plate 20 varies from well to well.

In an alternative practice of the invention, each of the holding chambers 64A–64D is sufficiently small to allow the chambers to be filled by capillary action. In such a practice, the pin assembly can consist of an array of narrow bore needles, such as stainless steel needles, that extend through the apertures of the lower block 54. The needles that are dipped into source solutions will be filled by capillary action. In one practice, the length of capillary which is to be filled at atmospheric pressure is determined approximately by:

$$H = \frac{2\gamma}{PGR}$$

where H equals Height, gamma equals surface tension, P equals solution density, G equals gravitational force and R equals needle radius. Thus the volume of fluid held by each vesicle can be controlled by selecting the dimensions of the interior bore. It is understood that at room temperature water will fill a 15 cm length of 100 µm radius capillary. Thus, a short bore nanoliter volume needle will fill to full capacity, but should not overflow because the capillary force is understood to be too small to form a meniscus at the top of the needle orifice. This prevents cross-contamination due to spillage. In one embodiment, the vesicles of the pin assembly can be provided with different sized interior chambers for holding and dispensing different volumes of fluid.

In an alternative practice, to decrease the volume of liquid that is drawn into the holding chambers of the vesicles, a small positive pressure can be provided within the interior chamber volume 58 by the pressure controller 28. The downward force created by the positive pressure can be used to counter the upward capillary force. In this way, the volume of fluid that is drawn by capillary force into the holding chambers of the vesicles can be controlled.

Figure 5B:
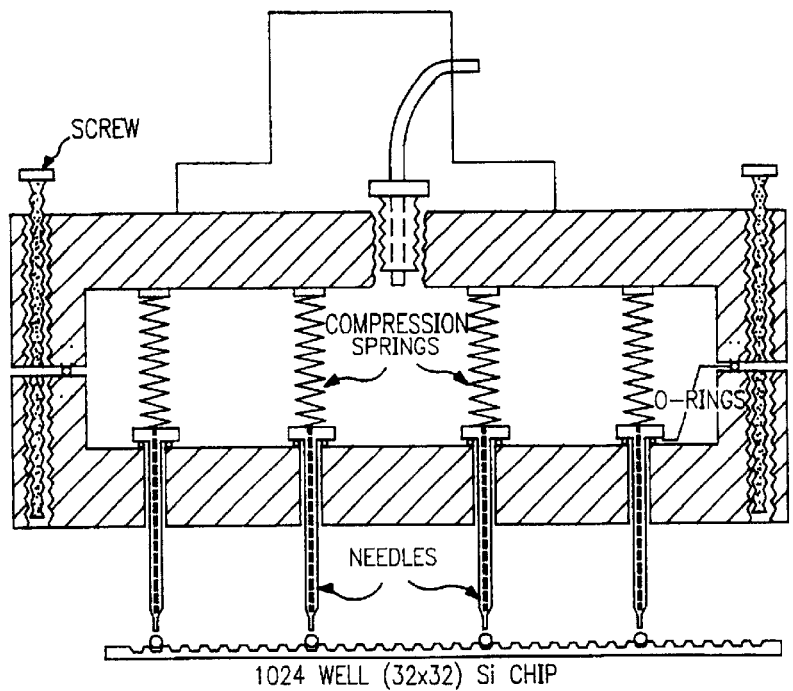

FIG. 5B shows that fluid within the holding chambers of the needle can be dispensed by a small positive pressure introduced through the central bore 88 extending through a swagelok 80. By regulating the pressure pulse that is introduced into the interior chamber volume 58, fluid can be ejected either as a spray or by droplet formation at the needle tip. It is understood that the rate of dispensing, droplet versus spray, depends in part upon the pressure applied by the pressure controller 28. In one practice, pressure is applied in the range of between 10 and 1,000 Torr of atmospheric pressure.

To this end the data processor 12 can run a computer program that controls and regulates the volume of fluid dispensed. The program can direct the controller 28 to eject a defined volume of fluid, either by generating a spray or by forming a drop that sits at the end of the vesicle, and can be contacted with the substrate surface for dispensing the fluid thereto.

Figure 5C:
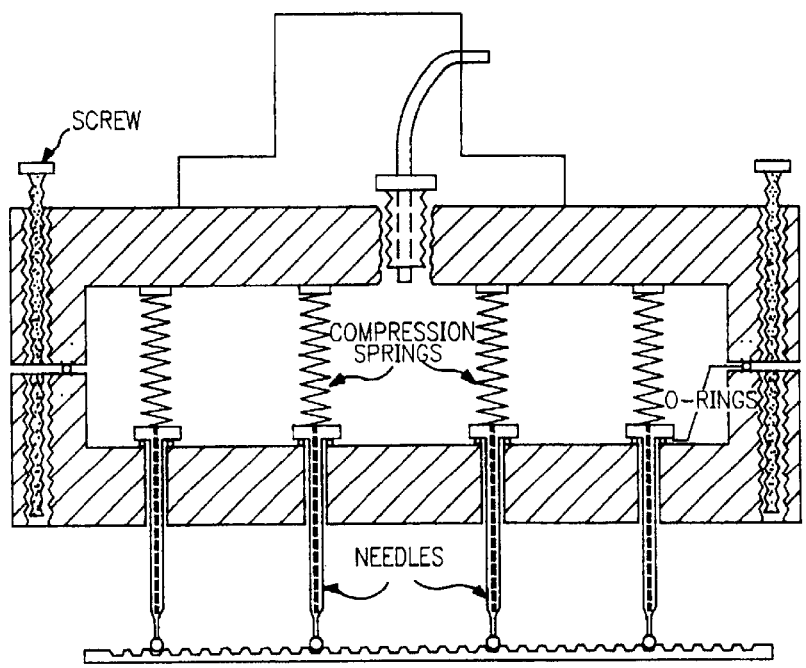
Figure 5D:
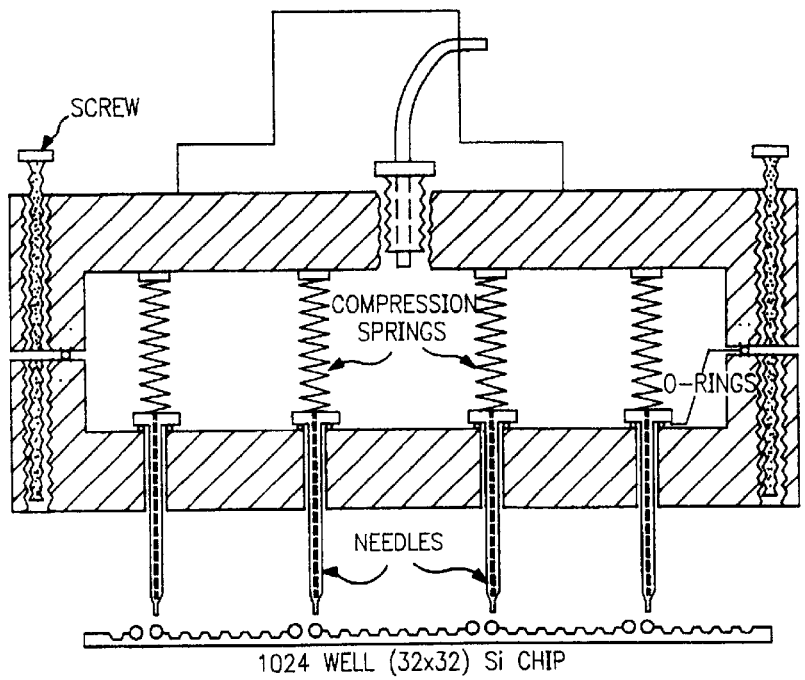

FIGS. 5C and 5D show the earlier steps shown in FIGS. 5A–5B can again be performed, this time at a position on the substrate surface that is offset from the earlier position. In the depicted process, the pin tool is offset by a distance equal to the distance between two wells 92. It will be apparent that other offset printing techniques can be employed without departing from the scope of the invention.

It will be understood that several advantages of the pin assembly depicted in FIG. 2 are achieved. For example, rinsing between dispensing events is straightforward, requiring only single or multiple pin fillings and emptying events with a rinse solution. Moreover, since all holding chambers fill to full capacity, the accuracy of the volumes dispensed varies only according to needle inner dimensions which can be carefully controlled during pin production. Further the device is cost effective, with the greatest expense attributed to the needles, however because no contact with a surface is required, the needles are exposed to little physical strain or stress, making replacement rare and providing long life.

Alternatively, deposition of sample material onto substrate surface can include techniques that employ pin tool assemblies that have solid pin elements extending from a block wherein a robotic assembly dips the solid pin elements of the pin assembly into a source of sample material to wet the distal ends of the pins with the sample materials. Subsequently the robotic assembly can move the pin assembly to a location above the substrate and then lower the pin assembly against the surface of the substrate to contact the individual wetted pins against the surface for spotting material of the substrate surface.

Figure 6A:
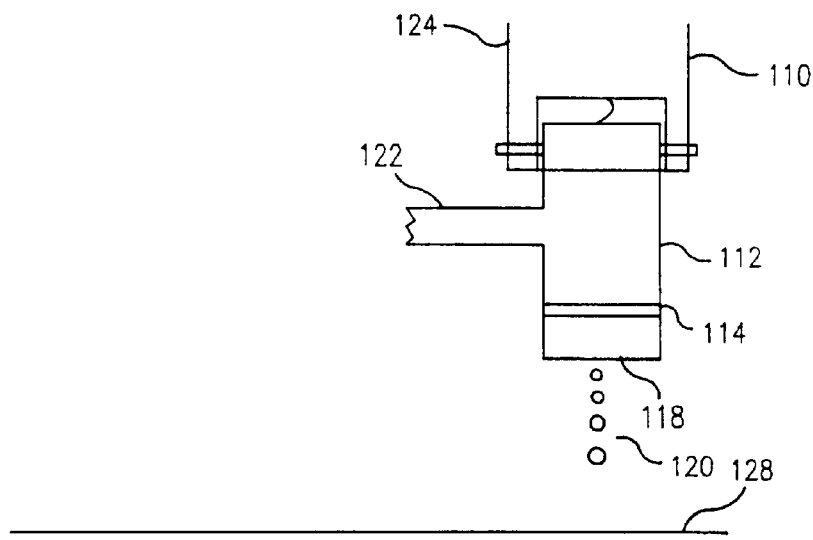
FIGS. 6A–6B depict an alternative assembly for dispensing material to the surface of a substrate.
Figure 6B:
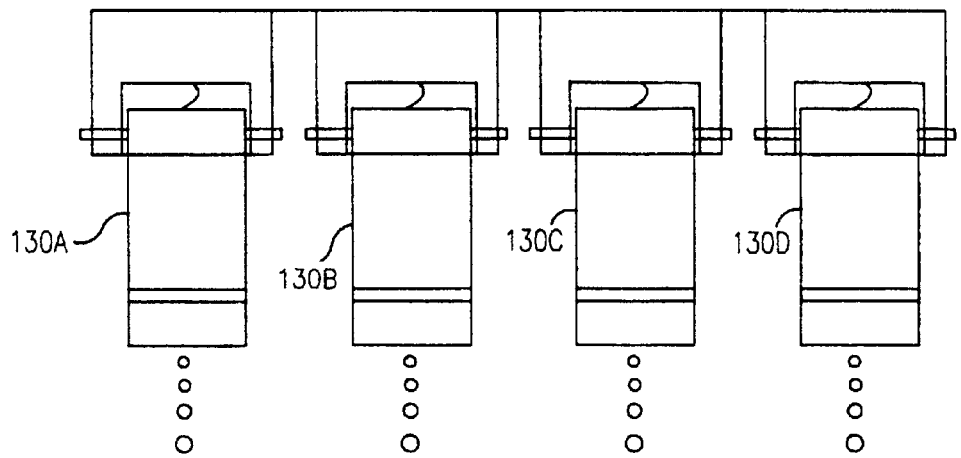

FIGS. 6A and 6B depict another alternative system for dispensing material on or to the surface of the substrate. In particular, FIG. 6A depicts a jet printing device 110 which includes a capillary element 112, a transducer element 114 and orifice (not shown) 118, a fluid conduit 122, and a mount 124 connecting to a robotic arm assembly, such as the robotic arm 24 depicted in FIG. 1. As further shown in FIG. 6A the jet assembly 110 is suitable for ejecting from the orifice 118 a series of drops 120 of a sample material for dispensing sample material onto the surface 128.

The capillary 112 of the jet assembly 110 can be a glass capillary, a plastic capillary, or any other suitable housing that can carry a fluid sample and that will allow the fluid sample to be ejected by the action of a transducer element, such as the transducer element 114. The transducer element 114 depicted in FIG. 6A is a piezo electric transducer element which forms around the parameter of the capillary 112 and can transform an electrical pulse received from the pulse generator within a robotic assembly 16 to cause fluid to eject from the orifice 118 of the capillary 112. One such jet assembly having a piezoelectric transducer element is manufactured by MicroFab Technology, Inc., of Germany. Any jet assembly, however, that is suitable for dispensing defined and controlled the volumes of fluid can be used herein including those that use piezoelectric transducers, electric transducers, electrorestrictive transducers, magnetorestrictive transducers, electromechanical transducers, or any other suitable transducer element. In the depicted embodiment, the capillary 112 has a fluid conduit 122 for receiving fluid material. In an optional embodiment, fluid can be drawn into the capillary by action of a vacuum pressure that will draw fluid through the orifice 118 when the orifice 118 is submerged in a source of fluid material. Other embodiments of the jet assembly 110 can be practiced with the invention without departing from the scope thereof.

FIG. 6B illustrates a further alternative assembly suitable for p being carried on the robotic arm of a robotic assembly, such as the assembly 16 depicted in FIG. 1. FIG. 6B illustrates four jet assemblies connected together, 130A–130D. Similar to the pin assembly in FIG. 2, the jet assembly depicted in FIG. 6B can be employed for the parallel dispensing of fluid material. It will be obvious to one of ordinary skill in the art of electrical engineering, that each of the jet assemblies 130A–130D can be operated independently of the others, for allowing the selective dispensing of fluid from select ones of the jet assemblies. Moreover, each of the jet assemblies 130A–130D can be independently controlled to select the volume of fluid that is dispensed from each respected one of the assembly 130A–130D. Other modifications and alterations can be made to the assembly depicted in FIG. 6B without departing from the scope of the invention.

Methods for rapidly analyzing sample materials are also provided. To this end sample arrays can be formed on a substrate surface according to any of the techniques discussed above. The sample arrays are then analyzed by mass spectrometry to collect spectra data that is representative of the composition of the samples in the array. It is understood that the above methods provide processes that allow for rapidly dispensing definite and controlled volumes of analyte material. In particular these processes allow for dispensing sub to low nanoliter volumes of fluid. These low volume deposition techniques generate sample arrays well suited for analysis by mass spectrometry. For example, the low volumes yield reproducibility of spot characteristics, such as evaporation rates and reduced dependence on atmospheric conditions such as ambient temperature and light Continuing with the example shown in FIG. 1, the arrays can be prepared by loading oligonucleotides (0.1–50 ng/Ill) of different sequences or concentrations into the wells of a 96 well microtiter source plate 20; the first well can be reserved for holding a matrix solution. A substrate 34, such as a pitted silicon chip substrate, can be placed on the stage 26 of the robotics assembly 16 and can be aligned manually to orient the matrix of wells about a set of reference axes. The control program executing on the data processor 12 can receive the coordinates of the first well of the source plate 20. The robotic arm 24 can dip the pin assembly 38 into source plate 20 such that each of the 16 pins is dipped into one of the wells. Each vesicle can fill by capillary action so that the full volume of the holding chamber contains fluid. Optionally, the program executing on the data processor 12 can direct the pressure controller to fill the interior chamber 58 of the pin assembly 38 with a positive bias pressure that will counteract, in part, the force of the capillary action to limit or reduce the volume of fluid that is drawn into the holding chamber.

Optionally, the pin assembly 38 can be dipped into the same 16 wells of the source plate 20 and spotted on a second target substrate. This cycle can be repeated on as many target substrates as desired. Next the robotic arm 24 can dip the pin assembly 38 in a washing solution, and then dip the pin assembly into 16 different wells of the source plate 20, and spot onto the substrate target offset a distance from the initial set of 16 spots. Again this can be repeated for as many target substrates as desired. The entire cycle can be repeated to make a 2×2 array from each vesicle to produce an 8×8 array of spots (2×2 elements/vesicle×16 vesicles=64 total elements spotted). However, it will be apparent to anyone of ordinary skill in the art that process suitable for forming arrays can be practiced with the present invention without departing from the scope thereof.

Oligonucleotides of different sequences or concentrations can be loaded into the wells of up to three different 384-well microtiter source plates; one set of 16 wells can be reserved for matrix solution. The wells of two plates are filled with washing solution. Five microtiter plates can be loaded onto the stage of the robotic assembly 16. A plurality of target substrates can be placed abutting an optional set of banking or registration pins disposed on the stage 26 and provided for aligning the target substrates along a set of reference axes. If the matrix and oligonucleotide are not pre-mixed, the pin assembly can be employed to first spot matrix solution on all desired target substrates. In a subsequent step the oligonucleotide solution can be spotted in the same pattern as the matrix material to re-dissolve the matrix. Alternatively, a sample array can be made by placing the oligonucleotide solution on the wafer first, followed by the matrix solution, or by pre-mixing the matrix and oligonucleotide solutions.

After depositing the sample arrays onto the surface of the substrate, the arrays can be analyzed using any of a variety of means (e.g., spectrometric techniques, such as UV/VIS, IR, fluorescence, chemiluminescence, NMR spectrometry or mass spectrometry). For example, subsequent to either dispensing process, sample loaded substrates can be placed onto a MALDI-TOF source plate and held there with a set of beveled screw mounted polycarbonate supports. In one practice, the plate can be transferred on the end of a probe to be held onto a 1 $\mu$m resolution, 1" travel xy stage (Newport) in the source region of a time-of-flight mass spectrometer. It will be apparent to one of ordinary skill in the art that any suitable mass spectrometry tool can be employed with the present invention without departing from the scope thereof.

Preferred mass spectrometer formats for use with the arrays described herein include ionization (I) techniques including but not limited to matrix assisted laser desorption (MALDI), continuous or pulsed electrospray (ESI) and related methods (e.g. Ionspray or Thermospray), or massive cluster impact (MCI); those ion sources can be matched with detection formats including linear or non-linear reflectron time-of-flight (TOF), single or multiple quadruple, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected for example, using ESI (Valaskovic, G. A. et al., (1996) *Science* 273: 1199–1202) or MALDI (Li, L. et al., (1996) *J. Am. Chem. Soc* 118: 1662–1663) mass spectrometry.

Thus, it will be understood that in processes described herein a completely non-contact, high-pressure spray or partial-contact, low pressure droplet formation mode can be employed. In the latter, the only contact that will occur is between the droplet and the walls of the well or a hydrophilic flat surface of the substrate 34. In neither practice need there be any contact between the needle tip and the surface.

Preferred Embodiments

Figure 7:
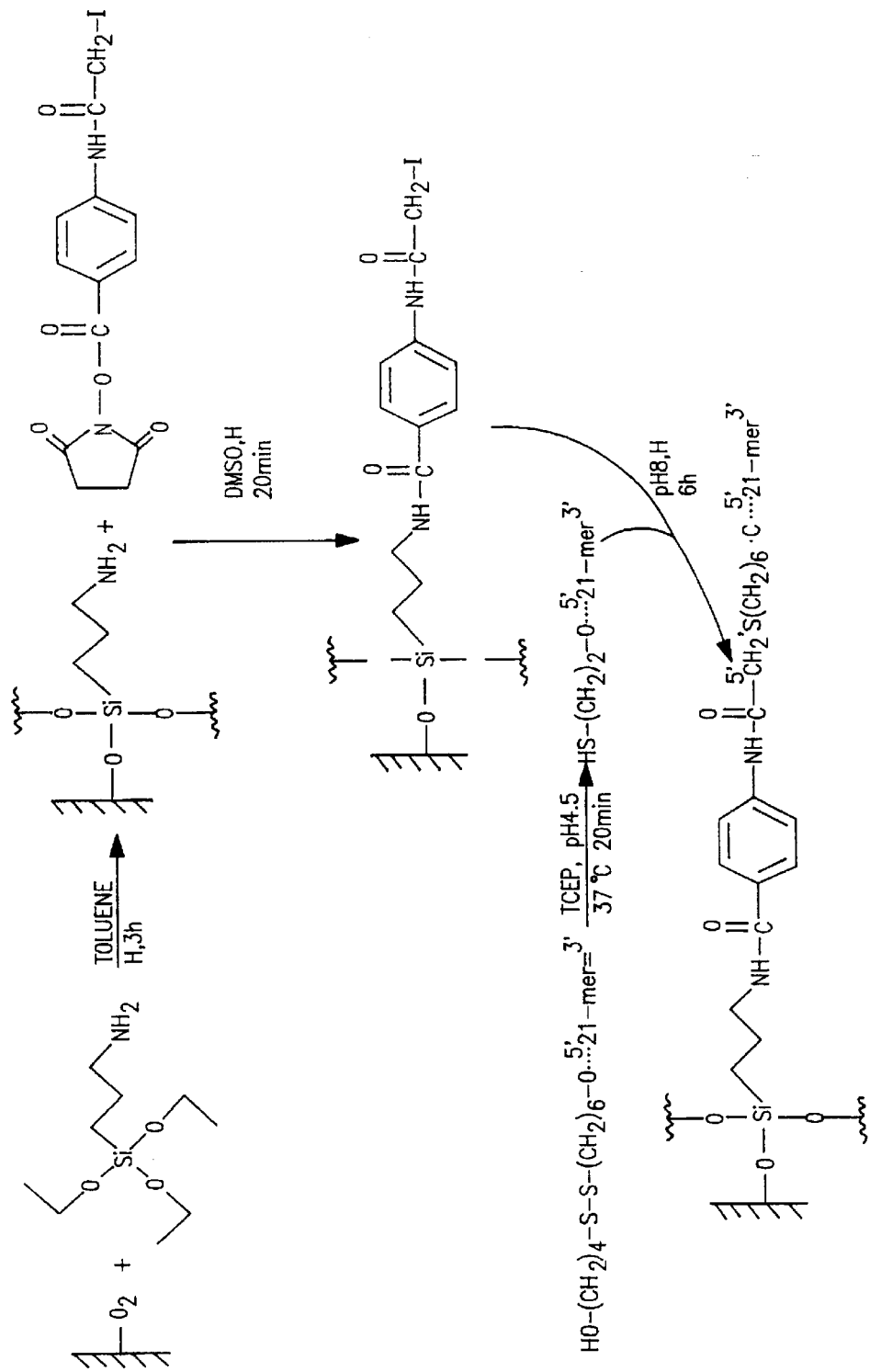
FIG. 7 is a schematic showing covalent attachment of oligodeoxynucleotides to a silicon dioxide surface as described in the methods herein. In particular, silicon dioxide was reacted with 3-aminopropyltriethoxysilane to produce a uniform layer of primary amino groups on the surface. A heterobifunctional crosslinking agent was then reacted with the primary amine to incorporate an iodoacetamide-group. An oligodeoxynucleotide containing a 3'- or 5'-disulfide (shown as the 5') was treated with tris-(2-carboxyethyl) phosphine (TCEP) to reduce the disulfide to a free thiol, which was then coupled to the iodoacetamido-surface.

In one preferred embodiment, a nucleic acid molecule can be covalently immobilized on a silica support by functionalization of the support with an amino functionality (e.g., by derivatization of the support with a reagent such as 3-aminopropyl-triethoxysilane (Aldrich Chemical Co., Milwaukee, Wis.); see FIG. 7). Other functionalized oxysilanes or orthosilicates can be used, and are commercially available (e.g., from Gelest, Inc., Tullytown, Pa.). For example, 3-mercaptopropyltriethoxy-silane can be used to functionalize a silicon surface with thiol groups. The amino-functionalized silica can then be reacted with a heterobifunctional reagent such as N-succinimidyl (4-iodoacetyl) aminobenzoate (SIAB) (Pierce, Rockford, Ill.). Other homo- and hetero-bifunctional reagents which can be employed are available commercially, e.g., from Pierce. Finally, a nucleic acid functionalized with a thiol,group (e.g., at the 5'-terminus) is covalently bound to the derivatized silica support by reaction of the thiol functionality of the nucleic acid molecule with the iodoacetyl functionality of the support.

In certain embodiments, the nucleic acid can be reacted with the cross-linking reagent to form a cross-linker/nucleic acid conjugate, which is then reacted with a functionalized support to provide an immobilized nucleic acid. Alternatively, the cross-linker can be combined with the nucleic acid and a functionalized solid support in one pot to provide substantially simultaneous reaction of the cross-linking reagent with the nucleic acid and the solid support. In this embodiment, it will generally be necessary to use a heterobifunctional cross-linker, i.e., a cross-linker with two different reactive functionalities capable of selective reaction with each of the nucleic acid and the functionalized solid support.

The methods provided herein are useful for producing spatially-addressable arrays of nucleic acids immobilized on insoluble supports. For example, the methods can be used to provide arrays of different nucleic acids immobilized on pins arranged in an array. In another embodiment, a photocleavable protecting group on the insoluble support can be selectively cleaved (e.g., by photolithography) to provide portions of a surface activated for immobilization of a nucleic acid. For example, a silicon surface, modified by treatment with 3-mercaptopropyl-triethoxysilane to provide thiol groups, can be blocked with a photocleavable protecting group (for examples of photocleavable protecting groups, see, e.g., PCT Publication WO 92/10092, or McCray et al., (1989) *Ann. Rev. Biophys. Biorhys. Chem.* 18:239–270), and be selectively deblocked by irradiation of selected areas of the surface, e.g., by use of a photolithography mask. A nucleic acid modified to contain a thiol-reactive group can then be attached directly to the support, or, alternatively, a thiol-reactive cross-linking reagent can be reacted with the thiol-modified support, followed by (or substantially simultaneously with) reaction with a nucleic acid to provide immobilized nucleic acids. A nucleic acid base or sequence, once immobilized on a support according to the methods described herein, can be further modified according to known methods. for example, the nucleic acid sequence can be lengthened by performing solid-phase nucleic acid synthesis according to conventional techniques, including combinatorial techniques.

Insoluble supports comprising nucleic acids are provided herein. Preferably the nucleic acids are covalently bound to a surface of the insoluble support through at least one sulfur atom, i.e., the nucleic acids are covalently bound to the surface through a linker moiety which includes at least one sulfur atom. Such covalently bound nucleic acids are readily produced by the methods described herein. The insoluble supports can be used in a variety of applications including those that involve hybridization and sequencing. Exemplary applications are illustrated in the Examples.

In preferred embodiments, the covalently bound nucleic acids are present on the surface of the insoluble support at a density of at least about 20 fmol/mm$^2$, more preferably at least about 75 fmol/mm$^2$, still more preferably at least about fmol/mm$^2$, yet more preferably at least about 100 fmol/mm$^2$, and most preferably at least about 150 fmol/mm$^2$.

In another aspect, combinatorial libraries of immobilized nucleic acids, covalently bound to a solid support as described above are provided.

In still another aspect, a kit for immobilized nucleic acids on a solid support is provided. In one embodiment, the kit comprises an appropriate amount of: i) a thiol-reactive cross-linking reagent; and ii) a surface-modifying reagent for modifying a surface with a functionality (preferably other than a thiol) which can react with the thiol-reactive cross-linking reagent. The kit can optionally include an insoluble support, e.g., a solid surface, e.g., magnetic microbeads, for use in immobilized nucleic acids. The kit can also include a reagent for modifying a nucleic acid with a thiol functionality.

In another embodiment, the kit comprises a reagent for modifying the surface of a support with a thiol moiety, and a thiol-reactive cross-linking reagent which can react with a thiol moiety of a support. In certain embodiments, the kit also includes an insoluble support, e.g., a solid surface, e.g., magnetic microbeads, for use in immobilizing nucleic acids.

The kits described herein can also optionally include appropriate buffers; containers for holding the reagents; and/or instructions for use.

In yet another embodiment, the insoluble supports covalently bound with nucleic acids, e.g., the entire surface or spatially addressable or pre-addressable array formats, can be used in a variety of solid phase nucleic acid chemistry applications, including but not limited to nucleic acid synthesis (chemically and enzymatically), hybridization and/or extension, and in diagnostic methods based in nucleic acid detection and polymorphism analyses (see, e.g., U.S. Pat. No. 5,605,798). Accordingly, further provided herein are methods of reacting nucleic acid molecules in which the nucleic acid molecules are immobilized on a surface either by reacting a thiol-containing derivative of the nucleic acid molecule with an insoluble support containing a thiol-reactive group or by reacting a thiol-containing insoluble support with a thiol-reactive group-containing derivative of the nucleic acid molecule and thereafter further reacting the immobilized nucleic acid molecules.

In a particular embodiment, the immobilized nucleic acid is further reacted by hybridizing with a nucleic acid that is complementary to the immobilized nucleic acid or a portion thereof. In another embodiment, the immobilized nucleic acid is further reacted by extension of a nucleic acid that is hybridized to the immobilized nucleic acid or a portion thereof. Extension reactions such as these can be used, for example, in methods of sequencing DNA molecules that are immobilized to an insoluble support using the processes described herein. Thus, also provided herein are methods of determining the sequence of a DNA molecule on a substrate in which a thiol-containing derivative of the DNA molecule is immobilized on the surface of an insoluble support containing thiol-reactive groups and hybridized with a single-stranded nucleic acid complementary to a portion of the immobilized DNA prior to carrying out DNA synthesis in the presence of one or more dideoxynucleotides.

The present invention is further illustrated by the following Examples, which are intended merely to further illustrate and should not be construed as limiting. The entire contents of all the of the references (including literature references, issued patents, published patent applications, and co-pending patent applications) cited throughout this application are hereby expressly incorporated by reference.

EXAMPLE 1

High Density Attachment of DNA to Silicon Wafers

Materials and Methods

All reagents, unless otherwise noted, were obtained from Aldrich Chemical, Milwaukee, Wis.

Silicon Surface Preparation

Silicon wafers were washed with ethanol, flamed over bunsen burner, and immersed in an anhydrous solution of 25% (by volume) 3-aminopropyltriethoxysilane in toluene for 3 hours. The silane solution was then removed, and the wafers were washed three times with toluene and three times with dimethyl sulfoxide (DMSO). The wafers were then incubated in a 10 mM anhydrous solution of N-succinimidyl (4-iodoacetyl) aminobenzoate (SIAB) (Pierce Chemical, Rockford, Ill.) in anhydrous DMSO. Following the reaction, the SIAB solution was removed, and the wafers were washed three times with DMSO.

Since it was impossible to monitor the condensation of SIAB and the amino group while on the solid support of the wafer, the reaction was performed in solution to determine the optimal reaction time. Thin layer chromatography (TLC) (glass backed silica plates with a 254 nm fluorescent indicator) (Baker, Phillipsburg, NF) was employed using 95:5 chloroform:methanol (Baker, Phillipsburg, NJ) which enabled separation of the two starting materials. It was possible to visualize the SIAB starting material under long wave ultraviolet light (302 nm); 3-aminopropyltriethoxysilane was not active under ultraviolet light, therefore, the plate was sprayed with a solution of ninhydrin which reacts with primary amines to reveal a purple spot upon heating. A microscale reaction was run in chloroform/DMSO using a slight molar excess of SIAB in comparison to 3-aminopropyltriethoxysilane and monitored with the above mentioned TLC conditions.

Oligonucleotide Modifications

Reduction of the disulfide from 3'- or 5'-disulfide-containing oligodeoxynucleotides (Operon Technologies, Alameda, Calif. or Oligo Etc., Wilsonville, Oreg.) was monitored using reverse-phase FPLC (Pharmacia, Piscataway, N.J.); a shift can be seen in the retention time of the oligodeoxynucleotide upon cleavage of the disulfide. Various reduction methods were investigated to determine the optimal conditions. In one case, the disulfide-containing oligodeoxynucleotide (31.5 nmol, 0.5 mM) was incubated with dithiothreitol (DTT) (Pierce Chemical, Rockford, Ill.) (6.2 mmol, 100 mM) as pH 8.0 and 37° C. With the cleavage reaction essentially complete, the free thiol-containing oligodeoxynucleotide was isolated using a Chromaspin-10 column (Clontech, Palo Alto, Calif.) since DTT may compete in the subsequent reaction. Alternatively, tris-(2-carboxyethyl) phosphine (TCEP) (Pierce Chemical, Rockford, Ill.) has been used to cleave the disulfide. The disulfide-containing oligodeoxynucleotide (7.2 nmol, 0.36 mM) was incubated with TCEP in pH 4.5 buffer at 37° C. It is not necessary to isolate the product following the reaction since TCEP does not competitively react with the iodoacetamido functionality. Varying concentrations of TCEP were used for the cleavage reaction to determine the optimal conditions for the conjugation reaction.

Probe Coupling

To each wafer which had been derivatized to contain the iodoacetamido functionality as described above was added a 10 mM aqueous solution of the free-thiol containing oligodeoxynucleotide in 100 mM phosphate buffer, pH 8; the reaction was allowed to proceed for a minimum of five hours at room temperature in 100% relative humidity. Following the reaction, the oligodeoxynucleotide solution was removed, and the wafers were washed two times in 5×SSC buffer (75 mM sodium citrate, 750 mM sodium chloride, pH 7) with 50% formamide (USB, Cleveland, Ohio) at 65° C. for 1 hour each.

Radiochemical Determination of Probe Density

In order to determine the amount of DNA covalently attached to a surface or the amount of a complementary sequence hybridized, radiolabeled probes were employed. In cases where a 5'-disulfide-containing oligodeoxynucleotide was to be immobilized, the 3'-terminus was radiolabeled using terminal transferase enzyme and a radiolabeled dideoxynucleoside triphosphate; in a standard reaction, 15 pmol (0.6 µM) of the 5'-disulfide-containing oligodeoxynucleotide was incubated with 50 µCi (16.5 pmol, 0.66 µM) of [α-$^{32}$P] dideoxyadenosine-5'triphosphate (ddATP) (Amersham, Arlington Height, Ill.) in the presence of 0.2 mM 2-mercaptoethanol. Upon the addition of 40 units of the terminal deoxynucleotidyl transferase enzyme (USB, Clevetand, Ohio), the reaction was allowed to proceed for one hour at 37° C. After this time, the reaction was stopped by immersion of the vial in 75° C. water bath for ten minutes, and the product was isolated using a Chromaspin-10 column (Clontech, Palo Alto, Calif.). Similarly, a 5'-disulfide-containing oligodeoxynucleotide was radiolabeled with $^{35}$S.

In cases where a 3'-disulfide-containing oligodeoxynucleotide was to be immobilized, the 5'-terminus was radiolabeled using T4 polynucleotide kinase and a radiolabeled nucleoside triphosphate. For example, 15 pmol (0.6 µM) of the 3'-disulfide-containing oligodeoxynucleotide was incubated with 50 µCi (16.5 pmol, 0.66 µM) of [λ$^{32}$P] adenosine-5'triphosphate (ATP) (Amersham, Arlington Height, Ill.) in the presence of 50 mM Tris-HCl, pH 7.6, 10 mM MgCl$_2$ 10 mM 2-mercaptoethanol. Following the addition of 40 units of T4 polynucleotide kinase, the reaction was allowed to proceed for 1 hour at 37° C. The reaction was stopped by immersion of the vial in a 75° C. water bath for ten minutes; the product was then isolated using a Chromaspin-10 column (Clontech, Palo Alto, Calif.).

To determine the density of covalently immobilized probe, the disulfide-containing oligodeoxynucleotide of choice was added to a trace amount of the same species than had been radiolabeled as described above. The disulfide was cleaved, the probe was immobilized on iodoacetamido-functionalized wafers, the wafers were washed, and then exposed to a phosphorimager screen (Molecular Dynamics, Sunnyvale, Calif.). For each different oligodeoxynucleotide utilized, reference spots were made on polystyrene in which the molar amount of oligodeoxynucleotide was known; these reference spots were exposed to the phosphorimager screen as well. Upon scanning the screen, the quantity (in moles) of oligodeoxynucleotide bound to each chip was determined by comparing the counts to the specific activities of the references.

Hybridization and Efficiency

To a wafer that had been functionalized with an immobilized probe was added a solution of a complementary sequence (10 µM) in 1M NaCl and TE buffer. The wafer and solution were heated to 75° C. and allowed to cool to room temperature over 3 hours. After this time, the solution was removed, and the wafer was washed two times with TE buffer.

To determine the amount of oligonucleotide hybridized, immobilization of the probe was first carried out as described above except that the probe was labeled with $^{35}$S rather than $^{32}$P. The density of immobilized probe was determined with the phosphorimager. Next, the same wafer was incubated in TE buffer, 1M NaCl, and its complementary strand (10 µM) which had been radiolabeled with $^{32}$P. Hybridization was carried out as previously described. Following a wash to remove non-specific binding, the wafer and reference were exposed to a phosphorimager screen with a piece of copper foil between the screen and the wafer. The copper foil serves to block the signal from $^{35}$S, while allowing the $^{32}$P signal to pass freely. The molar amount of hybridized oligonucleotide is then determined, thus revealing the percent of covalently immobilized probe that is available for hybridization.

MALDI-TOF Mass Spectrometric Analysis

As described above, wafers containing non-radiolabeled immobilized oligodeoxynucleotide (name: TCUC; sequence: GAATTCGAGCTCGGTACCCGG; molecular weight; 6455Da; SEQ ID NO. 1) were synthesized, and a complementary sequence (name: MJM6; sequence: CCGGGTACCGAGCTCGAATTC; molecular weight: 6415Da; SEQ ID NO. 2) was hybridized. The wafers were washed in 50 mM ammonium citrate buffer for cation exchange to remove sodium and potassium ions on the DNA backbone (Pieles, U. et al., (1993) *Nucl. Acids Res.*, 21:3191–3196). A matrix solution of 3-hydroxypicolinic acid (3-HPA, 0.7 M in 50% acetonitrile, 10% ammonium citrate; Wu, K. J., et al. (1993) *Rapid Commun. Mass Spectrom.*, 7:142–146) was spotted onto the wafer and allowed to dry at ambient temperature. The wafers were attached directly to the sample probe of a Finnigan MAT (Bremen, Germany) Vision 2000 reflectron TOF mass spectrometer using a conducting tape. The reflectron possesses a 5 keV ion source and 20 keV post-acceleration; a nitrogen laser was employed; and all spectra were taken in the positive ion mode.

Results

Surface Chemistry

Employing standard silicon dioxide modification chemistry, a silicon wafer was reacted with 3-aminopropyltriethoxysilane to produce a uniform layer of primary amino groups on the surface. As shown in FIG. 7, the surface was then exposed to a heterobifunctional crosslinker resulting in iodoacetamido groups on the surface. It was possible to determine the optimal reaction time of this reaction in solution using TLC. The SIAB crosslinker was visualized under long wave ultraviolet light (302 nm) to reveal a spot with an $R_f$ value of 0.58. 3-aminopropyltriethoxysilane was not active under ultraviolet light, therefore, ninhydrin was used to reveal a purple spot indicating the presence of a primary amine at the baseline. A microscale reaction was run using a slight molar excess of SIAB in comparison to 3-aminopropyltriethoxysilane; TLC analysis after approximately one minute revealed a new spot visible under long wave ultraviolet light with an $R_f$ value of 0.28. There was no evidence of a purple spot upon spraying with ninhydrin, thus all the 3-aminopropyltriethoxysilane starting material had been consumed in the reaction. UV light also revealed the excess SIAB which remained following the reaction. From these results, it was determined the reaction is complete after approximately one minute. In all cases, the iodoacetamido-functionalized wafers were used immediately to minimize hydrolysis of the labile iodoacetamido-functionality. Additionally, all further wafer manipulations were performed in the dark since the iodoacetamido-functionality is light sensitive.

Disulfide reduction of the modified oligonucleotide was monitored by observing a shift in retention time on reverse-phase FPLC. It was determined that after five hours in the presence of DTT (100 mM) or TCEP (10 mM), the disulfide was fully reduced to a free thiol. If the DTT reaction was allowed to proceed for a longer time, an oligonucleotide dimer formed in which pairs of free thiols had reacted. Such dimerization was also observed when the DTT was removed following the completion of the cleavage reaction. This dimerization was not observed when TCEP was employed as the cleavage reagent since this reaction is performed at pH 4.5, thus the free thiols were fully protonated inhibiting dimerization.

Figure 8:
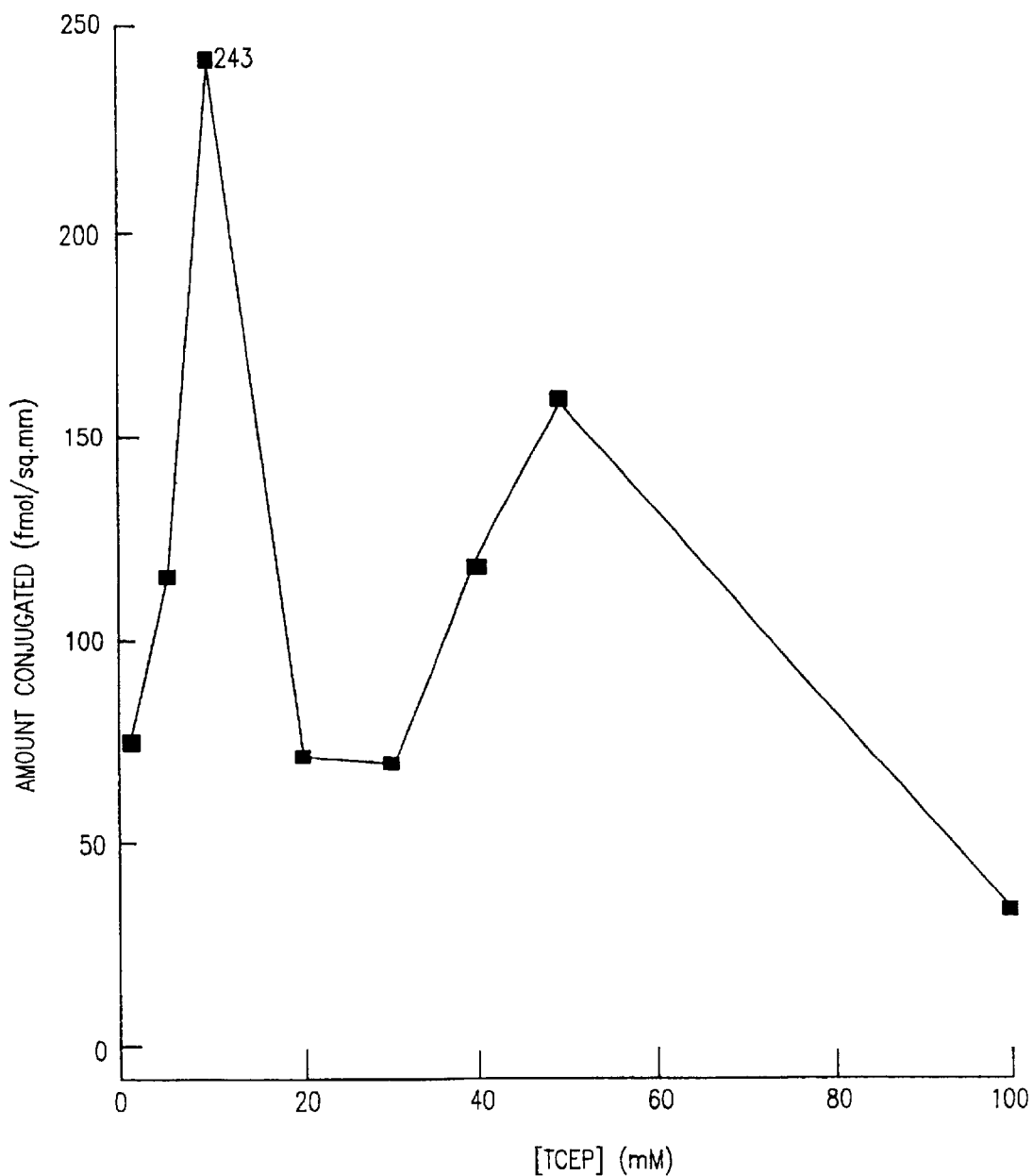
FIG. 8 is a graph which plots conjugation of oligodeoxynucleotide probes to a silicon surface as a function of TCEP concentration used in the disulfide reduction.

Immediately following disulfide cleavage, the modified oligonucleotide was incubated with the iodacetamidofunctionalized wafers. To ensure complete thiol deprotonation, the coupling reaction was performed at pH 8.0. The probe surface density achieved by this chemistry of silicon wafers was analyzed using radiolabeled probes and a phosphorimager. The probe surface density was also monitored as a function of the TCEP concentration used in the disulfide cleavage reaction (FIG. 8). Using 10 mM TCEP to cleave the disulfide and the other reaction conditions described above, it was possible to reproducibly yield a surface density of 250 fmol per square mm of surface. Identical experiments as described above were performed except that the oligonucleotide probe lacked a thiol modification; surface densities of less than 5 fmol per square mm of surface proved that non-specific binding is minimal and that probe coupling most likely occurred as proposed in FIG. 7.

Hybridization

After attaching $^{35}$S-labeled probes to the surface of wafers and determining conjugation density as described above, hybridization of $^{32}$P-labeled oligonucleotides was carried out; hybridization efficiency and density were determined using the phosphorimager and copper foil. It was determined experimentally that copper foil blocks 98.4% of an $^3$S signal, while fully allowing a $^{32}$P signal to be detected. The complementary sequence reproducibly hybridized to yield 105 fmol per square mm of surface; this corresponds to approximately 40% of the conjugated probes available for hybridization. Similarly, a non-complementary sequence was employed in this scheme yielding less than 5 fmol per square mm of surface in non-specific binding.

It is hypothesized that stearic interference between the tightly packed oligonucleotide on the flat surface inhibits hybridization efficiencies higher that 40%. With this in mind, a spacer molecule was incorporated between the terminus of the hybridizing region of the oligonucleotide and the support. The chosen spacers were a series of poly dT sequences ranging in length from 3 to 25. Upon examination of these samples with radiolabels and the phosphorimager, it was determined that 40% was still the maximum hybridization that could be achieved.

MALDI-TOF MS Analysis

Figure 9:
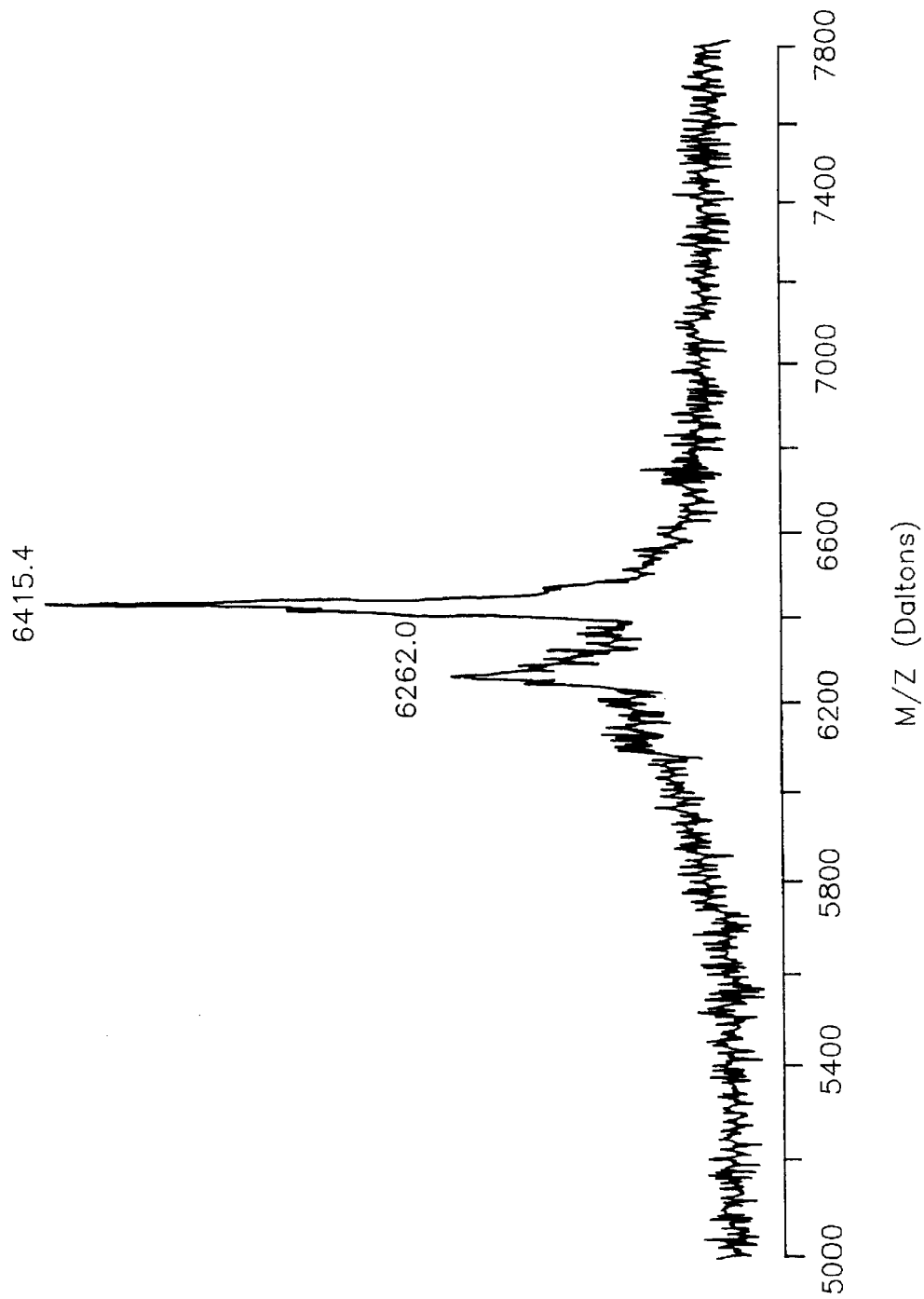
FIG. 9 is a matrix assisted laser desorbtionlionization-time-of-flight (MALDI-TOF) mass spectrum of a silicon wafer with the oligodeoxynucleotide sequence denoted "TCUC" (5'-GAATTCGAGCTCGGTACCCGG-3'; SEQ ID NO 1) covalently bound essentially as described in FIG. 7 and the oligodeoxynucleotide sequence denoted "MJM6" (5'-CCGGGTACCGAGCTCGAATTC-3'; SEQ ID NO 2) hybridized thereto.

Wafers were functionalized with probes, complementary sequences were hybridized, and the samples were analyzed under standard MALDI conditions as described above. Analysis revealed that only the annealed strand (MJM6) was observed in the mass spectrum with an experimental mass-to-charge ratio of 6415.4; the theoretical mass-to-charge ratio is 6415 (FIG. 9). Since there was no signal at a mass-to-charge ratio of 6455, it was determined that the wafer-conjugated strand (TCUC) was not desorbed thus the iodoacetamido linkage was stable enough to withstand the laser and remain intact. There was an additional signal observed at a mass-to-charge ration of 6262.0. This signal results from a depurination of guanosines since it is known that DNA is susceptible to the loss of purine bases during the MALDI process, (Nordoff, E., et al., (1992) *Rapid Commun. Mass Spectrom.* 6:771–776). The sample crystals on the wafer were not homogeneously distributed, thus it was necessary to hunt for a good spot . Because of this non-homogeneity, the mass resolution varied, but it generally ranged from 200–300 for the desorbed oligonucleotide in the mass spectra. In one set of experiments, non-complementary sequences were hybridized to the wafer; following a wash as previously described, analysis by MALDI-TOF MS revealed that minimal non-specific annealing had taken place since no signal was detected.

EXAMPLE 2

Immobilization of Amplified DNA Targets to Silicon Wafers

The SIAB-conjugated silicon wafers were also used to analyze specific free thiol-containing DNA fragments of a particular amplified DNA target sequence.

Figure 10:
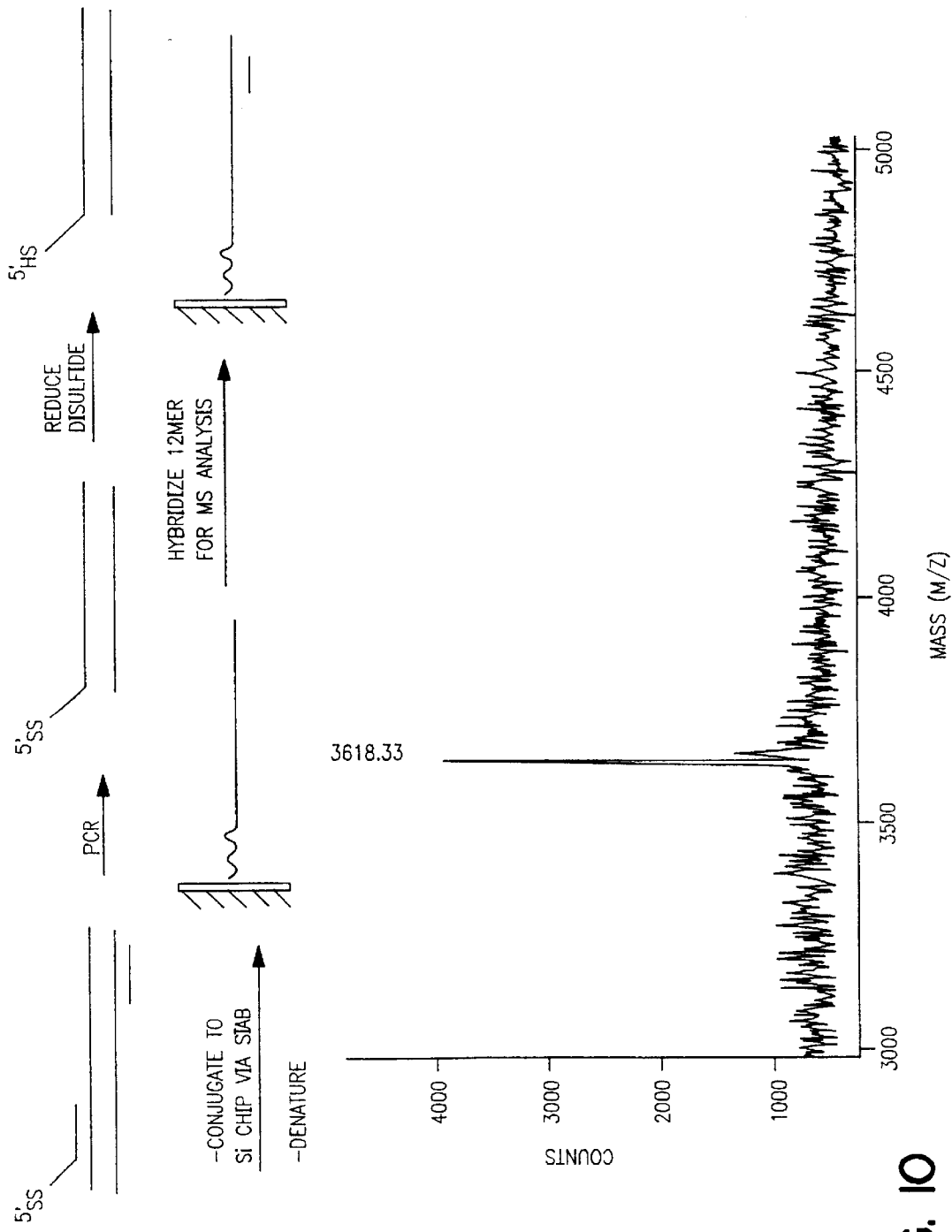
FIG. 10 is a schematic of the immobilization of specific thiol-containing DNA targets generated by polymerase chain reaction (PCR) to the surface of a silicon wafer. An oligonucleotide [SEQ ID NO: 7] complementary to a portion of the DNA target sequence was hybridized to the immobilized DNA target and MALDI-TOF MS analysis was performed revealing a predominant signal at an observed mass-to-charge ratio of 3618.33 corresponding to the hybridized oligonucleotide, which has a the theoretical mass-to-charge ratio of 3622.4.

As shown in FIG. 10, a 23-mer oligodeoxynucleotide containing a 5'-disulfide linkage [purchased from Operon Technologies; SEQ ID NO: 3] that is complementary to the 3'-region of a 112 bp human genomic DNA template [Genebank Acc. No.: Z52259; SEQ ID NO: 4] was used as a primer in conjunction with a commercially available 49-mer primer, which is complementary to a portion of the 5'-end of the genomic DNA [purchased from Operon Technologies; SEQ ID NO: 5], in PCR reactions to amplify a 135 bp DNA product containing a 5'-disulfide linkage attached to only one strand of the DNA duplex [SEQ ID NO: 6].

The PCR amplification reactions were performed using the Amplitaq GoldKit [Perkin Elmer Cataolog No. N808-0249]. Briefly, 200 ng 112 bp human genomic DNA template was incubated with 10 µM of 23-mer primer and 8 µM of commercially available 49-mer primer, 10 mM dNTPs, 1 unit of Amplitaq Gold DNA polymerase in the buffer provided by the manufacturer and PCR was performed in a thermocycler.

The 5'-disulfide bond of the resulting PCR product was fully reduced using 10 mM TCEP as described in EXAMPLE 1 to generate a free 5'-thiol group. The DNA strand containing free-thiol group was conjugated to the surface of the silicon wafer through the SIAB linker essentially as outlined in FIG. 7.

The silicon wafer conjugated with the 135 bp thiol-containing DNA was incubated with a complementary 12-mer oligonucleotide [SEQ ID NO: 7] and specifically hybridized DNA fragments were detected using MALDI-TOF MS analysis. The mass spectrum revealed a signal with an observed experimental mass-to-charge ratio of 3618.33; the theoretical mass-to-charge ratio of the 12-mer oligomer sequence is 3622.4 Da.

Thus, a specific DNA target molecule that contain a 5'-disulfide linkage can be amplified. The molecules are immobilized on a SIAB-derivatized silicon wafer using the methods described herein and specific complementary oligonucleotides may be hybridized to these target molecules and detected using MALDI-TOF MS analysis.

EXAMPLE 3

Spectrochip Mutant Detection in ApoE Gene

This example describes the hybridization of an immobilized template, primer extension and mass spectrometry for detection of the wildtype and mutant Apolipoprotein E gene for diagnostic purposes. This example demonstrates that immobilized DNA molecules containing a specific sequence can be detected and distinguished using primer extension of unlabeled allele specific primers and analysis of the extension products using mass spectrometry.

A 50 base synthetic DNA template complementary to the coding sequence of allele 3 of the wildtype apolipoprotein E gene:

5'-GCCTGGTACACTGCCAGGCGCTTCTGCAGGT CATCGGCATCGCGGAGGAG-3' [SEQ ID NO: 17]

or complement to the mutant apolipoprotein E gene carrying a G→A transition at codon 158:

5'-GCCTGGTACACTGCCAGGCACTTCTGCAGGT CATCGGCATCGCGGAGGAG-3' [SEQ ID NO: 18]

containing a 3'-free thiol group was coupled to separate SIAB-derivatized silicon wafers essentially as outlined in FIG. 7 and as described in Examples 1 and 2.

A 21-mer oligonucleotide primer:

5'-GATGCCGATGACCTGCAGAAG-3' [SEQ ID NO: 19] was hybridized to each of the immobilized templates and the primer was extended using a commercially available kit [e.g., Sequenase or Thermosequenase, U.S. Biochemical Corp]. The addition of Sequenase DNA polymerase or Thermosequenase DNA polymerase in the presence of three deoxyribonucleoside triphosphates (dNTPs; dATP, dGTP, dTTP) and dideoxyribonucleoside cytosine triphosphate (ddCTP) in buffer according to the instructions provided by the manufacturer resulted in a single base extension of the 21-mer primer bound to the immobilized template encoding the wildtype apolipoprotein E gene and a three base extension of the 21-mer primer bound to the immobilized template encoding the mutant form of apolipoprotein E gene.

The wafers were analyzed by mass spectrometry as described herein. The wildtype apolipoprotein E sequence results in a mass spectrum that distinguishes the primer with a single base extension (22-mer) with a mass-to-charge ratio of 6771.17 Da (the theoretical mass to charge ratio is 6753.5 Da) from the original 21-mer primer with a mass-to-charge ratio of 6499.64 Da. The mutant apolipoprotein E sequence results in a mass spectrum that distinguishes the primer with a three base extension (24-mer) with a mass-to-charge ratio of 7386.9 (the theoretical mass charge is 7386.9) from the original 21-mer primer with a mass to charge ration of 6499.64 Da.

EXAMPLE 4

Preparation of DNA Arrays Using Serial and Parallel Dispensing Tools

Robot-driven serial and parallel pL-nL dispensing tools were used to generate $10-10^3$ element DNA arrays on <1" square chips with flat or geometrically altered (e.g. with wells) surfaces for matrix assisted laser desorption ionization mass spectrometry analysis. In the former, a 'piezoelectric pipette' (70 $\mu$m id capillary) dispenses single or multiple ~0.2 nL droplets of matrix, and then analyte, onto the chip; spectra from as low as 0.2 fmol of a 36-mer DNA have been acquired using this procedure. Despite the fast (<5 sec) evaporation, micro-crystals of 3-hydroxypicolinic acid matrix containing the analyte are routinely produced resulting in higher reproducibility than routinely obtained with larger volume preparations; all of 100 five fmol spots of a 23-mer in 800 $\mu$m wells yielded easily interpreted mass spectra, with 99/100 parent ion signals having signal to noise ratio of >5. In a second approach, probes from 384 well microtiter plate are dispensed 16 at a time into chip wells or onto flat surfaces using an array of spring loaded pins which transfer ~20 nL to the chip by surface contact; MS analysis of array elements deposited with the parallel method are comparable in terms of sensitivity and resolution to those made with the serial method.

Description of the Piezoelectric Serial Dispenser

The experimental system developed from a system purchased from Microdrop GmbH, Norderstedt Germany and can include a piezoelectric element driver which sends a pulsed signal to a piezoelectric element bonded to and surrounding a glass capillary which holds the solution to be dispensed; a pressure transducer to load (by negative pressure) or empty (by positive pressure) the capillary; a robotic xyz stage and robot driver to maneuver the capillary for loading, unloading, dispensing, and cleaning, a stroboscope and driver pulsed at the frequency of the piezo element to enable viewing of 'suspended' droplet characteristics; separate stages for source and designation plates or sample targets (i.e. Si chip); a camera mounted to the robotic arm to view loading to designation plate; and a data station which controls the pressure unit, xyz robot, and piezoelectric driver.

Description of the Parallel Dispenser

The robotic pintool consists of 16 probes housed in a probe block and mounted on an X Y, Z robotic stage. The robotic stage was a gantry system which enables the placement of sample trays below the arms of the robot. The gantry unit itself is composed of X and Y arms which move 250 and 400 mm, respectively, guided by brushless linear servo motors with positional feedback provided by linear optical encoders. A lead screw driven Z axis (50 mm vertical travel) is mounted to the xy axis slide of the gantry unit and is controlled by an in-line rotary servo motor with positional feedback by a motor-mounted rotary optical encoder. The work area of the system is equipped with a slide-out tooling plate that holds five microtiter plates (most often, 2 plates of wash solution and 3 plates of sample for a maximum of 1152 different oligonucleotide solutions) and up to ten 20x20 mm wafers. The wafers are placed precisely in the plate against two banking pins and held secure by vacuum. The entire system is enclosed in plexi-glass housing for safety and mounted onto a steel support frame for thermal and vibrational damping. Motion control is accomplished by employing a commercial motion controller which was a 3-axis servo controller and is integrated to a computer; programming code for specific applications is written as needed.

Samples were dispensed with the serial system onto several surfaces which served as targets in the MALDI TOF analysis including [1] A flat stainless steel sample target as supplied for routine use in a Thermo Bioanalysis Vision 2000; [2] the same design stainless steel target with micromachined nanopits; [3] flat silicon (Si) wafers; [4] polished flat Si wafers; [5] Si wafers with rough (3–6 pLm features) pits; [6](a) 12×12 or ((b) 18×18) mm Si chips with (a) 10×10 (or (b) 16×16) arrays of chemically etched wells, each 800×8001 lm on a side with depths ranging from 99–400 (or(b) 120) micrometer, pitch (a) 1.0 (or(b) 1.125) mm; [7] 15×15 mm Si chips with 28×28 arrays of chemically etched wells, each 450×450 micrometer on a side with depths ranging from 48–300 micrometer, pitch 0.5 mm; [8]flat polycarbonate or other plastics; 19] gold and other metals; [10] membranes; [11] plastic surfaces sputtered with gold or other conducting materials. The dispensed volume is controlled from $10^{-10}$ to $10^{31\ 6}$ L by adjusting the number of droplets dispensed.

Sample Preparation and Dispensing

1. Serial

Oligonucleotides (0.1–50 ng/microliter of different sequence or concentrations were loaded into wells of a 96 well microtiter plate; the first well was reserved for matrix solution. A pitted chip (target 6a in MALDI targets' section) was placed on the stage and aligned manually. Into the (Windows-based) robot control software were entered the coordinates of the first well, the array size (ie number of spots in x and y) and spacing between elements, and the number of 0.2 nL drops per array element. The capillary was filled with ~10 microL rinse $H_2O$, automatically moved in view of a strobe light-illuminated camera for checking tip integrity and cleanliness while in continuous pulse mode, and emptied. The capillary was then filled with matrix solution, again checked at the stroboscope, and then used to spot an array onto flat or pitted surfaces. For Reproductability studies in different MS modes, typically a 10×10 array of 0.2–20 nL droplets were dispensed. The capillary was emptied by application of positive pressure, optionally rinsed with $H_2O$, and led to the source oligo plate where ~5

μL of 0.05–2.0 μM synthetic oligo were drawn. The capillary was then rastered in series over each of the matrix spots with 0.2–20 nL aqueous solution added to each.

2. Parallel

Parallel Programs were written to control array making by offset printing; to make an array of 64 elements on 10 wafers, for example, the tool was dipped into 16 wells of a 384 well DNA source plate, moved to the target (e.g. Si, plastic, metal), and the sample spotted by surface contact. The tool was then dipped into the same 16 wells and spotted on the second target; this cycle was repeated on all ten wafers. Next the tool was dipped in washing solution, then dipped into 16 different wells of the source plate, and spotted onto the target 2.25 mm offset from the initial set of 16 spots; again this was repeated on all 10 wafers; the entire cycle was repeated to make a 2×2 array from each pin to produce an 8×8 array of spots (2×2 elements/pin×16 pins=64 total elements spotted).

To make arrays for MS analysis, olegonucleotides of different sequences or concentrations were loaded into the wells of up to three different 384-well microtiter plates, one set of 16 wells was reserved for matrix solution. The wells of two plates were filled with washing solution. The five microtiter plates were loaded onto the slide-out tooling plate. Ten wafers were placed abutting the banking pins on the tooling plate, and the vacuum turned on. In cases where matrix and oligonucleotide were not pre-mixed, the pintool was used to spot matrix solution first on all desired array elements of the ten wafers. For this example, a 16×16 array was created, thus the tool must spot each of the ten wafers 16 times, with an offset of 1.125 mm. Next, the oligonucleotide solution was spotted in the same pattern to re-dissolve the matrix. Similarly, an array could be made by placing the oligonucleotide solution on the wafer first, followed by the matrix solution, or by pre-mixing the matrix and oligonucleotide solutions.

Mass Spectrometry

Subsequent to either dispensing scheme, loaded chips were held onto a MALDI-TOF source plate with a set of beveled screw mounted polycarbonated supports. The plate was transferred on the end of a probe to be held onto a 1 μm resolution, 1" travel xy stage (Newport) in the source region of a time-of-flight mass spectrometer. The instrument, normally operated with 18–26 kV extraction, could be operated in linear or curved field reflectron mode, and in continuous or delayed extraction mode.

RESULTS

Serial Dispensing with the Piezoelectric Pipette

While delivery of a saturated 3HPA solution can result in tip clogging as the solvent at the capillary-air interface evaporates, pre-mixing DNA and matrix sufficiently dilutes the matrix such that it remains in solution while stable sprays which could be maintained until the capillary was emptied were obtained; with 1:1 diluted (in $H_2O$) matrix solution, continuous spraying for >>10 minutes was possible. Turning off the piezo element so that the capillary sat inactive for >5 minutes, and reactivating the piezo element also did not result in a clogged capillary.

Initial experiments using stainless steel sample targets as provided by Finnigan Vision 2000 MALDI-TOF system run in reflectron mode utilized a pre-mixed solution of the matrix and DNA prior to dispensing onto the sample target. In a single microtiter well, 50 μL saturated matrix solution, 25 μL of a 51 μL solution of the 12-mer (ATCG)3, and 25 μL of a 51 μL solution of the 28-mer (ATCG)7 were mixed. A set of 10×10 arrays of 0.6 μL drops was dispensed directly onto a Finnigan Vision 2000 sample target disk; MALDI-TOF mass spectrum was obtained from a single array element which contained 750 attomoles of each of the two oligonucleotides. Interpretable mass spectra has been obtained for DNAs as large as a 53-mer (350 amol loaded, not shown) using this method.

Figure 11:
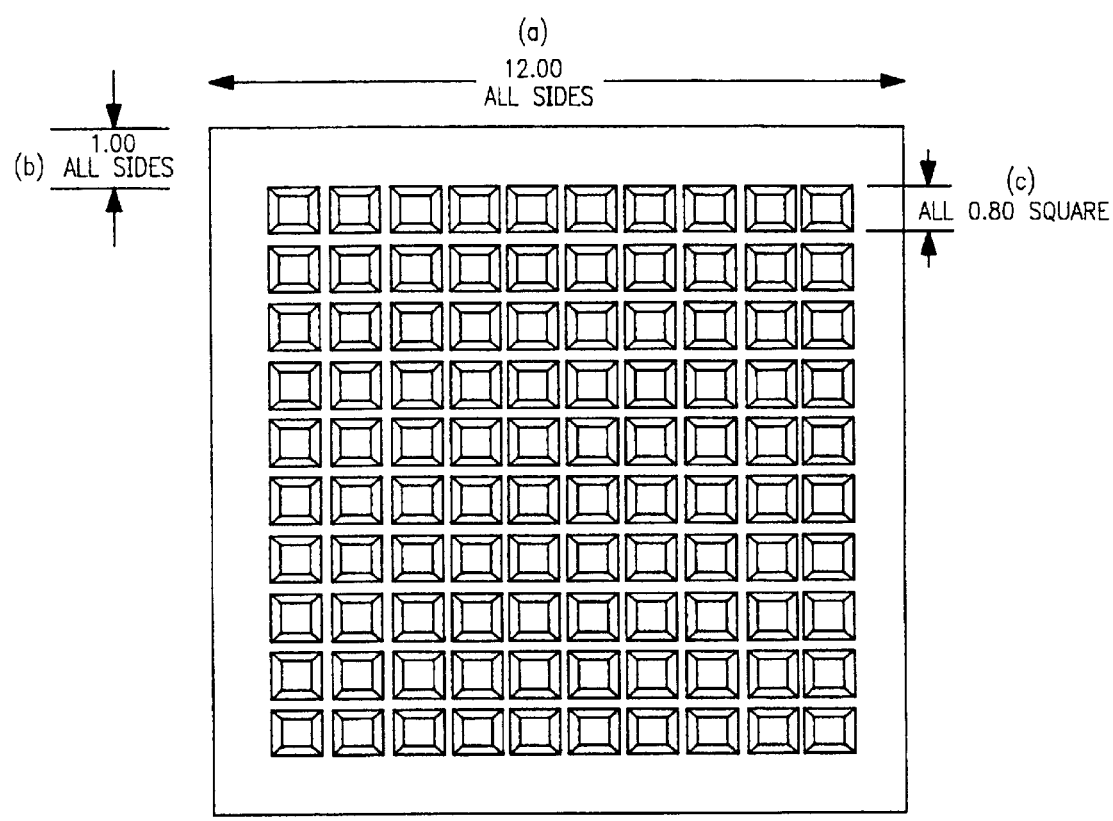
FIG. 11 depicts one embodiment of a substrate having wells etched therein that are suitable for receiving material for analysis.

Mass spectra were also obtained from DNAs microdispensed into the wells of a silicon chip. FIG. 11 shows a 12×12 mm silicon chip with 100 chemically etched wells; mask dimensions and etch time were set such that fustum (i.e., inverted flat top pyramidal) geometry wells with 800× 800 μm (top surface) and 100 μm depth were obtained. Optionally, the wells can be roughed or pitted. As described above, the hip edge was aligned against a raised surface on the stage to define the x and y coordinate systems with respect to the capillary. (Alternatives include optical alignment, artificial intelligence pattern recognition routines, and dowel-pin based manual alignment). Into each well was dispensed 20 droplets (~5 nL) of 3-HPA matrix solution without analyte; for the 50% $CH_3CN$ solution employed, evaporation times for each droplet were on the order of 5–10 seconds. Upon solvent evaporation, each microdispensed matrix droplet as viewed under a 120× stereomicroscope generally appeared as an amorphous and 'milky' flat disk; such appearances are consistent with those of droplets from which the FIG. 3b spectrum was obtained. Upon tip emptying, rinsing, and refilling with a 1.4 μm aqueous solution of a 23-mer DNA ($M_r$(calc)=6967 Da), the capillary was directed above each of the 100 spots of matrix where 5 nL of the aqueous DNA solution was dispensed directly on top of the matrix droplets. Employing visualization via a CCD camera, it appeared that the aqueous analyte solution mixed with and re-dissolved the matrix (complete evaporation took ~10 sec at ambient temperature and humidity). The amorphous matrix surfaces were converted to true micro-crystalline surfaces, with crystalline features on the order of <1 μm.

Figure 12:
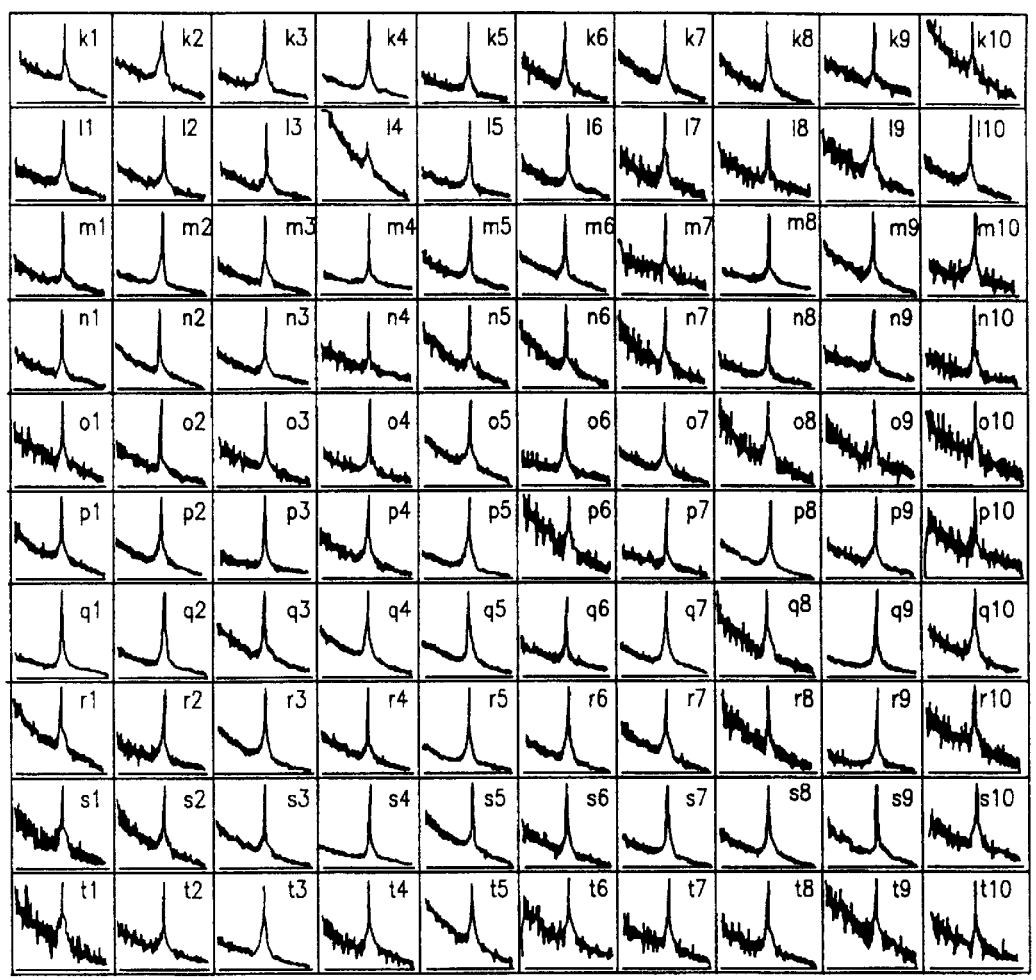
FIG. 12 depicts one example of spectra obtained from a linear time of flight mass spectrometer instrument and representative of the material composition of the sample material on the surface of the substrate depicted in FIG. 11.

Consistent with the improved crystallization afforded by the matrix re-dissolving method, mass spectrum acquisition appeared more reproducible than with pre-mixed matrix plus analyte solutions; each of the 100 five fmol spots of the 23-mer yielded interpreted mass spectra (FIG. 12), with 99/100 parent ion signals having signal to noise ratios of >5; such reproducibility was also obtained with the flat silicon and metallic surfaces tried (not shown). The FIG. 12 spectra were obtained on a linear TOF instrument operated at 26 kV. Upon internal calibration of the top left spectrum (well 'k1') using the singly and doubly charged molecular ions, and application of this calibration file to all other 99 spectra as an external calibration (FIG. 13), a standard deviation of <9 Da from the average molecular weight was obtained, corresponding to a relative standard deviation of ~0.1%.

Parallel Dispensing with the Robotic Pintool

Arrays were made with offset printing as described above. The velocity of the X and Y stages are 35 inches/sec, and the velocity of the Z stage is 5.5 inches/sec. It is possible to move the X and Y stages at maximum velocity to decrease the cycle times, however the speed of the Z stage is to be decreased prior to surface contact with the wafer to avoid damaging it. At such axes speeds, the approximate cycle time to spot 16 elements (one tool impression of the same solutions) on all ten wafers is 20 seconds, so to make an array of 256 elements would take ~5.3 minutes. When placing different oligonucleotide solutions on the array, an additional washing step much be incorporated to clean the pin tip prior to dipping in another solution, thus the cycle time would increase to 25 seconds or 6.7 minutes to make 10 wafers.

Sample delivery by the tool was examined using radiolabeled solutions and the phosphorimager as described previously; it was determined that each pin delivers approximately 1 nL of liquid. The spot-to-spot reproducibility is high. An array of 256 oligonucleotide elements of varying sequence and concentration was made on flat silicon wafers using the pintool, and the wafer was analyzed by MALDI-TOF MS.

EXAMPLE 5

Use of High Density Nucleic Acid Immobilization to Generate Nucleic Acid Arrays

Employing the high density attachment procedure described in EXAMPLE 1, an array of DNA oligomers amenable to MALDI-TOF mass spectrometry analysis was created on a silicon wafer having a plurality of locations, e.g., depressions or patches, on its surface. To generate the array, a free thiol-containing oligonucleotide primer was immobilized only at the selected locations of the wafer [e.g., see FIG. 14]. Each location of the array contained one of three different oligomers. To demonstrate that the different immobilized oligomers could be separately detected and distinguished, three distinct oligonucleotides of differing lengths that are complementary to one of the three oligomers were hybridized to the array on the wafer and analyzed by MALDI-TOF mass spectrometry.

Oligodeoxynucleotides

Three sets of complementary oligodeoxynucleotide pairs were synthesized in which one member of the complementary oligonucleotide pair contains a 3'- or 5'-disulfide linkage [purchased from Operon Technologies or Oligos, Etc.]. For example, Oligomer 1 [d(CTGATGCGTCGGATCATCTTTTTT-SS); SEQ ID NO: 8] contains a 3'-disulfide linkage whereas Oligomer 2 [d(SS-CCTCTTGGGAACTGTGTAGTATT); a 5'-disulfide derivative of SEQ ID NO: 3] and Oligomer 3 [d(SS-GAATTCGAGCTCGGTACCCGG); a 5'-disulfide derivative of SEQ ID NO: 1] each contain a 5'-disulfide linkage.

The oligonucleotides complementary to Oligomers 1–3 were designed to be of different lengths that are easily resolvable from one another during MALDI-TOF MS analysis. For example, a 23-mer oligonucleotide [SEQ ID NO: 9] was synthesized complementary to a portion of Oligomer 1, a 12-mer oligonucleotide [SEQ ID NO: 7] was synthesized complementary to a portion of Oligomer 2 and a 21-mer [SEQ ID NO: 2; sequence denoted "MJM6" in EXAMPLE 1] was synthesized complementary to a portion of Oligomer 3. In addition, a fourth 29-mer oligonucleotide [SEQ ID NO: 10] was synthesized that lacks complementarity to any of the three oligomers. This fourth oligonucleotide was used as a negative control.

Silicon Surface Chemistry and DNA Immobilization (a) 4×4 (16-location) Array

A 2×2 cm² silicon wafer having 256 individual depressions or wells in the form of a 16×16 well array was purchased from a commercial supplier [Accelerator Technology Corp., College Station, Tex.]. The wells were 800× 800 μm², 120 μm deep, on a 1.125 pitch. The silicon wafer was reacted with 3-aminopropyltriethoxysilane to produce a uniform layer of primary amines on the surface and then exposed to the heterobifunctional crosslinker SIAB resulting in iodoacetamido functionalities on the surface [e.g., see FIG. 7].

To prepare the oligomers for coupling to the various locations of the silicon array, the disulfide bond of each oligomer was fully reduced using 10 mM TCEP as depicted in EXAMPLE 1, and the DNA resuspended at a final concentration of 10 μM in a solution of 100 mM phosphate buffer, pH 8.0. Immediately following disulfide bond reduction, the free-thiol group of the oligomer was coupled to the iodoacetamido functionality at 16 locations on the wafer using the probe coupling conditions essentially as described in FIG. 7. To accomplish the separate coupling at 16 distinct locations of the wafer, the entire surface of the wafer was not flushed with an oligonucleotide solution but, instead, an ~30-nl aliquot of a predetermined modified oligomer was added in parallel to each of 16 locations (i.e., depressions) of the 256 wells on the wafer to create a 4×4 array of immobilized DNA using a pin tool as described herein (see e.g., the Detailed Description and Example 4 provided herein).

Figure 14:
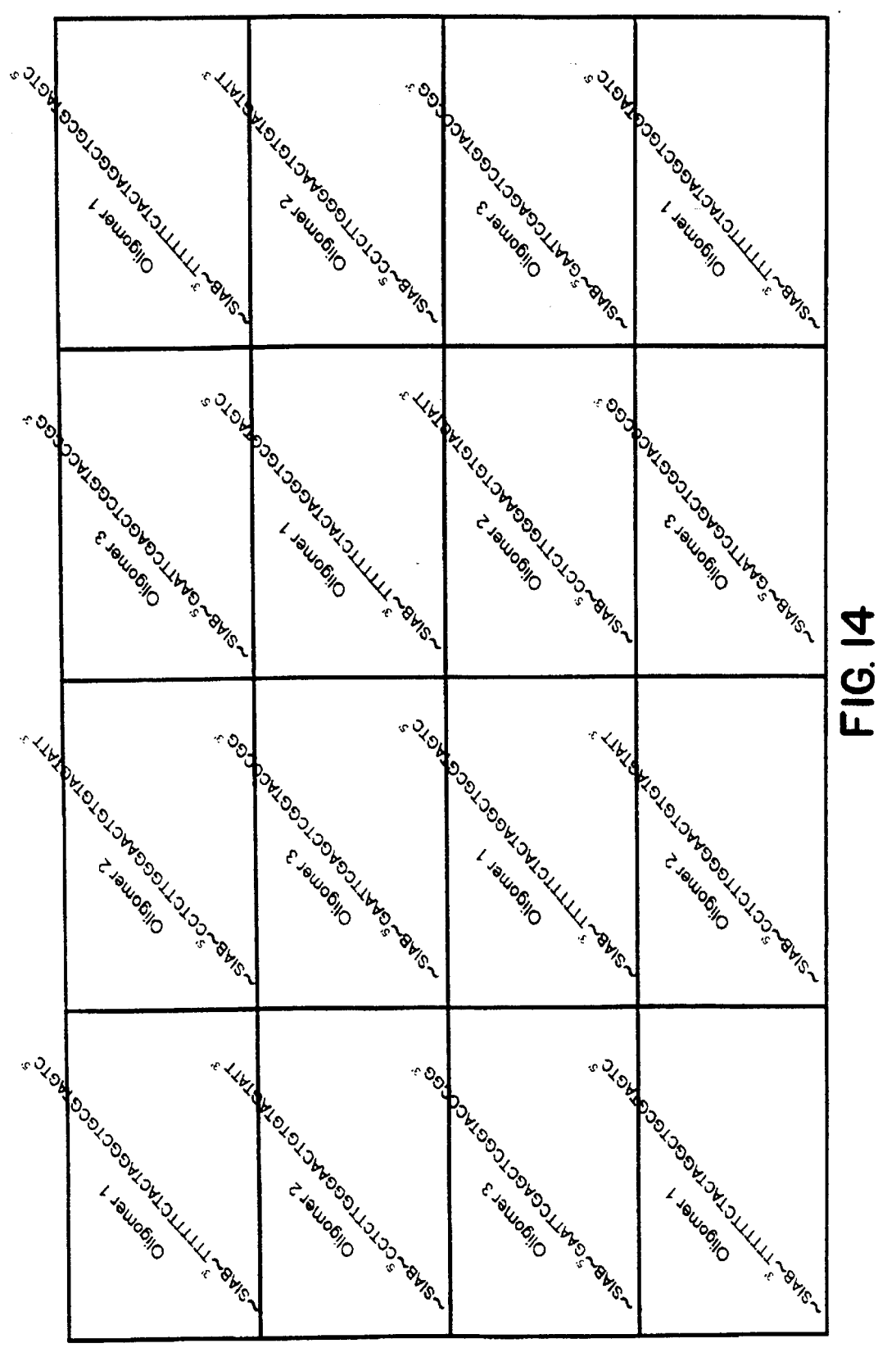

Thus, as shown in FIG. 14, one of modified Oligomers 1–3 was covalently immobilized to each of 16 separate wells of the 256 wells on the silicon wafer thereby creating a 4×4 array of immobilized DNA. For example, Oligomer 1 was conjugated at a well position in the upper left hand corner of the 4×4 array and Oligomer 2 was conjugated to the adjacent location, and so forth. An illustration of the completed array is shown in FIG. 14.

Figure 15:
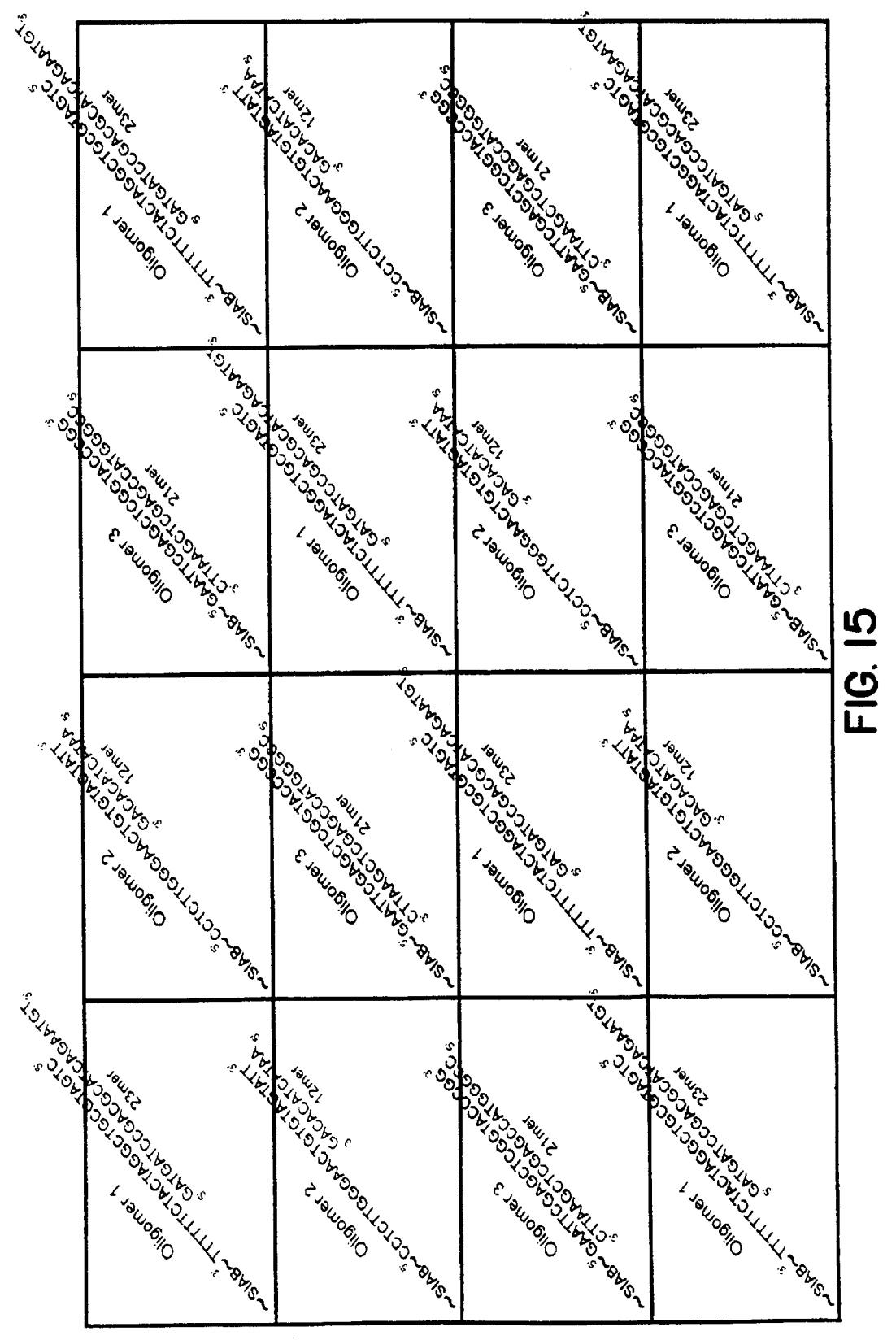

In carrying out the hybridization reaction, the three complementary oligonucleotides and the negative control oligonucleotide were mixed at a final concentration of 10 μM for each oligonucleotide in 1 ml of TE buffer [10 mM Tris-HCl, pH 8.0, 1 mM EDTA] supplemented with 1 M NaCl, and the solution was heated at 65° C. for 10 min. Immediately thereafter, the entire surface of the silicon wafer was flushed with 800 μl of the heated oligonucleotide solution. The complementary oligonucleotides were annealed to the immobilized oligomers by incubating the silicon array at ambient temperature for 1 hr, followed by incubation at 4° C. for at least 10 min. Alternatively, the oligonucleotide solution can be added to the wafer which is then heated and allowed to cool for hybridization. An illustration of the complementary oligonucleotides annealed to the specific oligomers covalently immobilized at each location is shown in FIG. 15.

The hybridized array was then washed with a solution of 50 mM ammonium citrate buffer for cation exchange to remove sodium and potassium ions on the DNA backbone (Pieles, U. et al., (1993) *Nucl. Acids Res.*, 21:3191–3196). A 6-nl aliquot of a matrix solution of 3-hydroxypicolinic acid [0.7 M 3-hydroxypicolinic acid-10% ammonium citrate in 50% acetonitrile; see Wu et al., *Rapid Commun. Mass Spectrom.* 7:142–146 (1993)] was added to each location of the array using a piezoelectric pipette as described herein.

The solution was allowed to dry at ambient temperature and thereafter a 6-nl aliquot of water was added to each location using a piezoelectric pipette to resuspend the dried matrix-DNA complex, such that upon drying at ambient temperature the matrix-DNA complex forms a uniform crystalline surface on the bottom surface of each location.

MALDI-TOF MS Analysis

Figure 16:
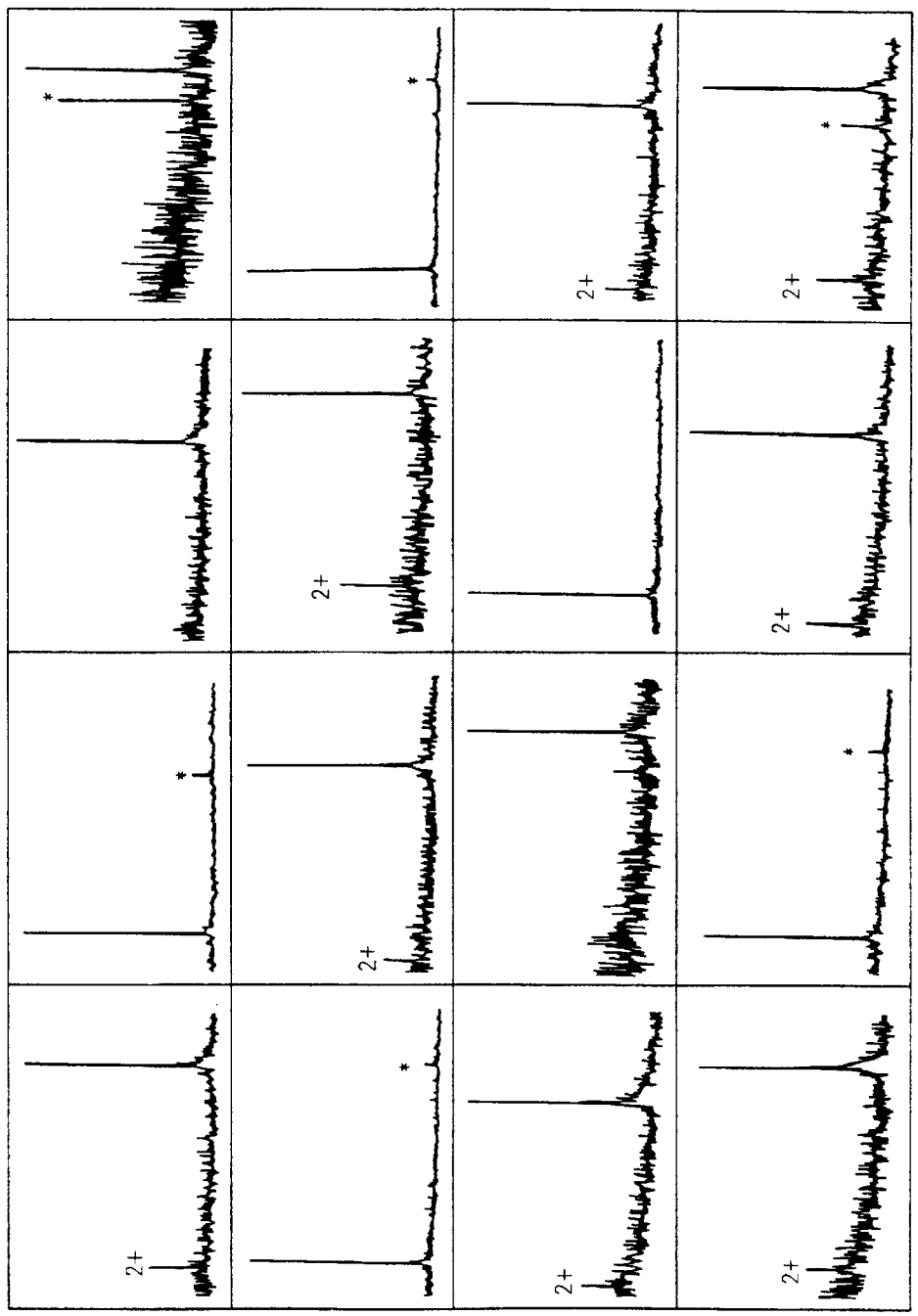
FIG. 16 is a representative MALDI-TOF mass spectrum of a 4×4 (16-location) DNA array on a silicon wafer shown schematically in FIG. 15. The spectrum reveals a single, predominant signal of an experimental mass-to-charge ratio in each location corresponding to the specific hybridized oligonucleotides. The 2+ indicates the position of a doubly charged molecule used as a reference standard during MALDI-TOF MS analysis. The * denotes residual amounts of contaminating oligonucleotide that remain on the surface of the chip following washing procedures. The relative position of the * signal reveals the approximate size of the contaminating oligonucleotide.

The MALDI-TOF MS analysis was performed in series on each of the 16 locations of the hybridization array illustrated in FIG. 15 essentially as described in EXAMPLE 1. The resulting mass spectrum of oligonucleotides that specifically hybridized to each of the 16 locations of the DNA hybridization array is shown in FIG. 16. The mass spectrum revealed a specific signal at each location representative of observed experimental mass-to-charge ratio corresponding to the specific complementary nucleotide sequence.

For example, in the locations that have only Oligomer 1 conjugated thereto, the mass spectrum revealed a predominate signal with an observed experimental mass-to-charge ratio of 7072.4 approximately equal to that of the 23-mer; the theoretical mass-to-charge ratio of the 23-mer is 7072.6 Da. Similarly, specific hybridization of the 12-mer oligonucleotide to the array, observed experimental mass-to-charge ratio of 3618.33 Da (theoretical 3622.4 Da), was detected only at those locations conjugated with Oligomer 2 whereas specific hybridization of MJM6 (observed experimental mass-to-charge ratio of 6415.4) was detected only at those locations of the array conjugated with Oligomer 3 [theoretical 6407.2 Da].

None of the locations of the array revealed a signal that corresponds to the negative control 29-mer oligonucleotide (theoretical mass-to-charge ratio of 8974.8) indicating that specific target DNA molecules can be hybridized to oligomers covalently immobilized to specific locations on the surface of the silicon array and a plurality of hybridization assays may be individually monitored using MALDI-TOF MS analysis.

(b) 8×8 (64-location) Array

A 2×2 $cm^2$ silicon wafer having 256 individual depressions or wells that form a 16×16 array of wells was purchased from a commercial supplier [Accelerator Technology Corp., College Station, Tex.]. The wells were 800×800 $\mu m^2$, 120 $\mu m$ deep, on a 1.125 pitch. The silicon wafer was reacted with 3-aminopropyltriethoxysilane to produce a uniform layer of primary amines on the surface and then exposed to the heterobifunctional crosslinker SIAB resulting in iodoacetamido functionalities on the surface [e.g., see FIG. 7].

Figure 17:
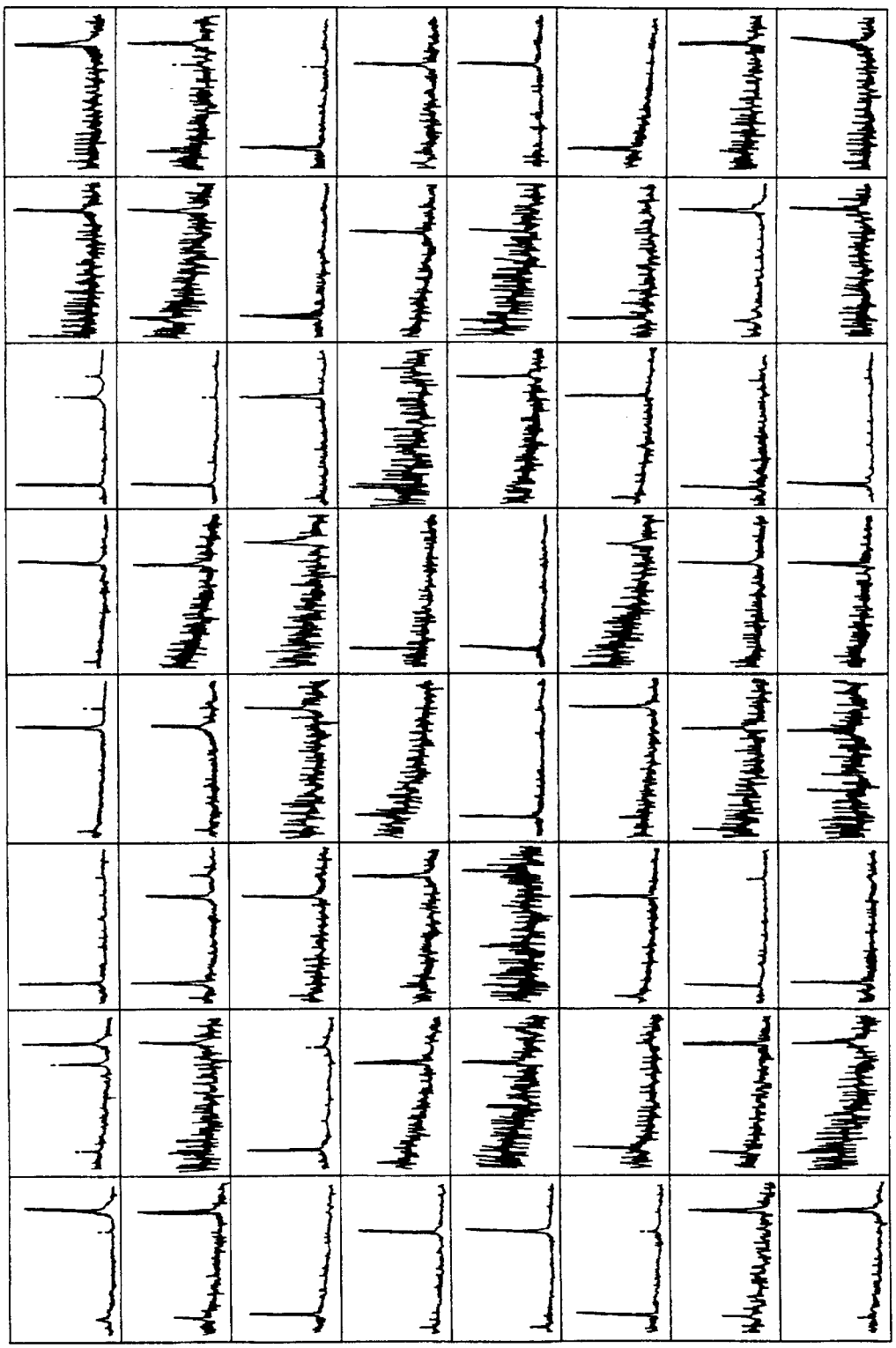
FIG. 17 is a representative MALDI-TOF mass spectrum of an 8×8 (64-location) DNA array. The spectrum reveals a single, predominant signal of an experimental mass-to-charge ratio corresponding to the predicted specific hybridized oligonucleotides. The * denotes residual amounts of contaminating oligonucleotide that remain on the surface of the wafer following washing procedures. The relative position of the * signal reveals the approximate size of the contaminating oligonucleotide.

Following the procedures described above for the preparation of the 16-location DNA array, Oligomers 1–3 were immobilized to 64 locations forming an 8×8 array on the 256 well silicon wafer, hybridized to complementary oligonucleotides and analyzed by MALDI-TOF MS analysis. FIG. 17 shows the mass spectrum of the 64-location DNA array analyzed in series by MALDI-TOF analysis. As shown for the 16-location array, specific hybridization of the complementary oligonucleotide to each of the immobilized thiol-containing oligomers was observed in each of the locations of the DNA array.

EXAMPLE 6

Extension of Hybridized DNA Primers Bound to DNA Templates Immobilized on a Silicon Wafer The SIAB-derivatized silicon wafers can also be employed for primer extension reactions of the immobilized DNA template using the procedures essentially described in U.S. Pat. No. 5,605,798.

Figure 18:
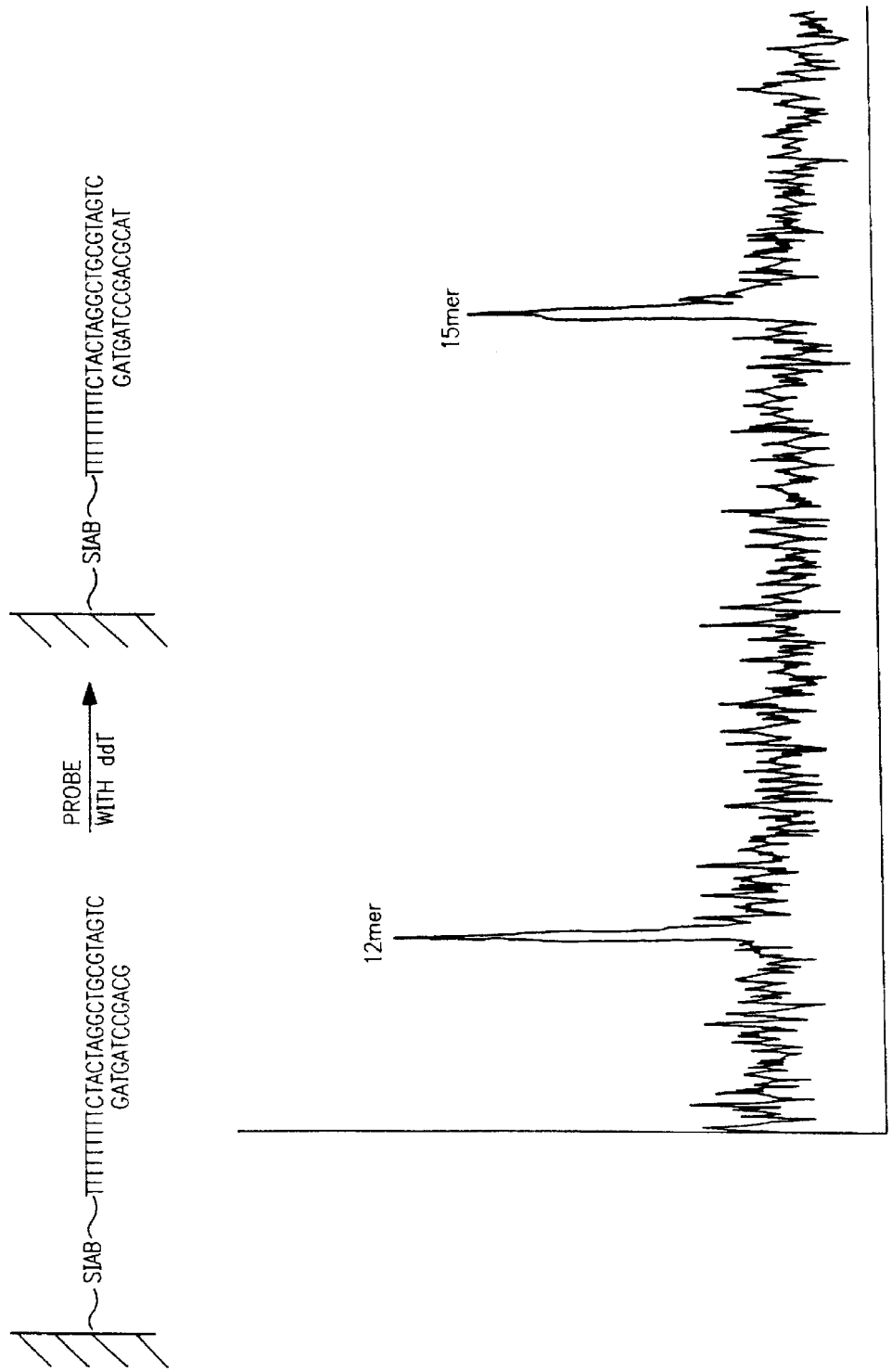
FIG. 18 is an illustration of nucleotide extension of a DNA primer annealed to a thiol-containing DNA template immobilized to the surface of a SIAB-derivatized silicon wafer. A complementary 12-mer oligonucleotide primer [SEQ ID NO: 12] was hybridized to a 27-mer thiol-containing oligonucleotide [SEQ ID NO: 11] immobilized to a silicon support through the SIAB crosslinker. The silicon surface containing the immobilized DNA duplex was incubated with DNA polymerase in the presence of dATP, dCTP, dGTP and ddTTP under extension conditions and subjected to MALDI-TOF MS analysis. The mass spectrum of the silicon wafer revealed the presence of two predominant signals; one of a mass-to-charge ratio equal to the unextended 12-mer oligonucleotide as well as a signal corresponding to a 15-mer DNA molecule that has been extended on the wafer by 3 nucleotides to the first position in the sequence in which a ddTTP was incorporated.

As shown in FIG. 18, a 27-mer oligonucleotide [SEQ ID NO: 11] containing a 3'-free thiol group was coupled to a SIAB-derivatized silicon wafer as described above, for example, in Example 1. A 12-mer ligonucleotide primer [SEQ ID NO: 12] was hybridized to the immobilized oligonucleotide and the primer was extended using a commercially available kit [e.g., Sequenase or ThermoSequenase, U.S. Biochemical Corp]. The addition of Sequenase DNA polymerase or ThermoSequenase DNA polymerase in the presence of three deoxyribonucleoside triphosphates (dNTPs; dATP, dGTP, dCTP) and dideoxyribonucleoside thymidine triphosphate (ddTTP) in buffer according to the instructions provided by the manufacturer resulted in a 3-base extension of the 12-mer primer while still bound to the silicon wafer. The wafer was then analyzed by MALDI-TOF mass spectrometry as described above. As shown in FIG. 18, the mass spectrum results clearly distinguish the 15-mer [SEQ ID NO: 13] from the original unextended 12-mer thus indicating that specific extension can be performed on the surface of a silicon wafer and detected using MALDI-TOF MS analysis.

EXAMPLE 7

Figure 19:
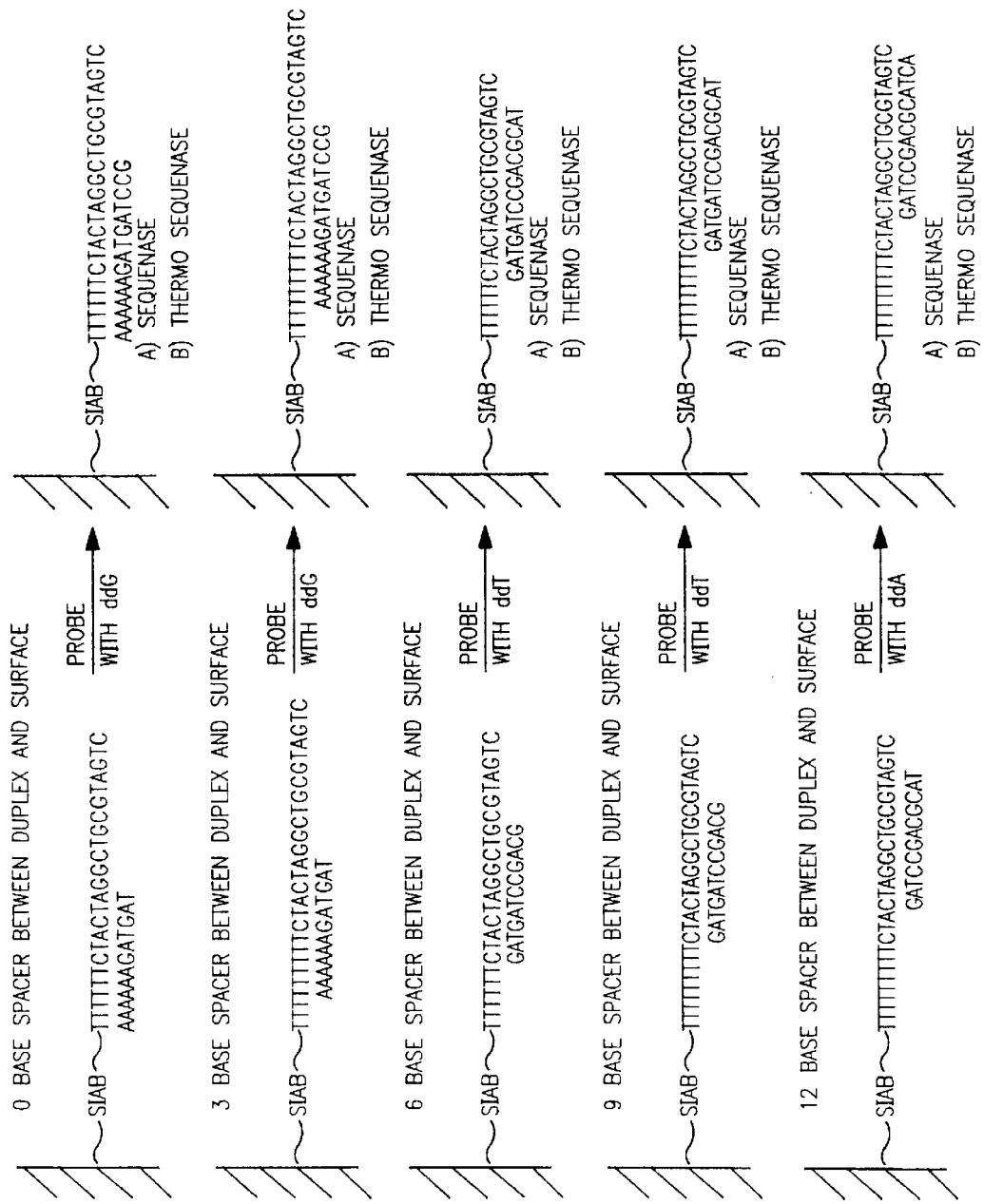
FIG. 19 diagrams an experiment designed to test the effect of the distance between the SIAB-derivatized surface and the DNA duplex formed on primer extension reactions. Two thiol-containing oligonucleotides of different sequence [SEQ ID NOs: 8 & 11] were immobilized to a SIAB-derivatized silicon surface and incubated with specific oligonucleotides that form a DNA duplex with 0, 3, 6, 9 and 12 base spacers between the SIAB-derivatized surface and the DNA duplex formed by the oligonucleotide hybridized to the immobilized thiol-containing DNA. The free 3'-end of the hybridized oligonucleotide was extended using either Sequenase DNA polymerase or ThermoSequenase DNA polymerase in the presence of the three deoxynucleotide triphosphates and the corresponding diddeoxynucleotide triphosphate under extension conditions and the resulting reaction products were subjected to MALDI-TOF MS analysis.

Effect of Linker Length on Polymerase Extension of Hybridized DNA Primers Bound to DNA Templates Immobilized on a Silicon Wafer The effect of the distance between the SIAB-conjugated silicon surface and the duplex DNA formed by hybridization of the target DNA to the immobilized oligomer template was investigated, as well as choice of enzyme [e.g., see FIG. 19].

Two SIAB-derivatized silicon wafers were conjugated to the 3'-end of two free thiol-containing oligonucleotides of identical DNA sequence except for a 3-base poly dT spacer sequence incorporated at the 3'-end [SEQ ID NOs: 8 & 11]. These two oligonuclotides were synthesized and each was separately immobilized to the surface of a silicon wafer through the SIAB cross-linker [e.g., see FIG. 7]. Each wafer was incubated with a 12-mer oligonucleotide [SEQ ID NOs: 12, 14 and 15] complementary to portions of the nucleotide sequences common to both of the oligonucleotides by denaturing at 75° C. and slow cooling the silicon wafer. The wafers were then analyzed by MALDI-TOF mass spectrometry as described above.

Figure 20:
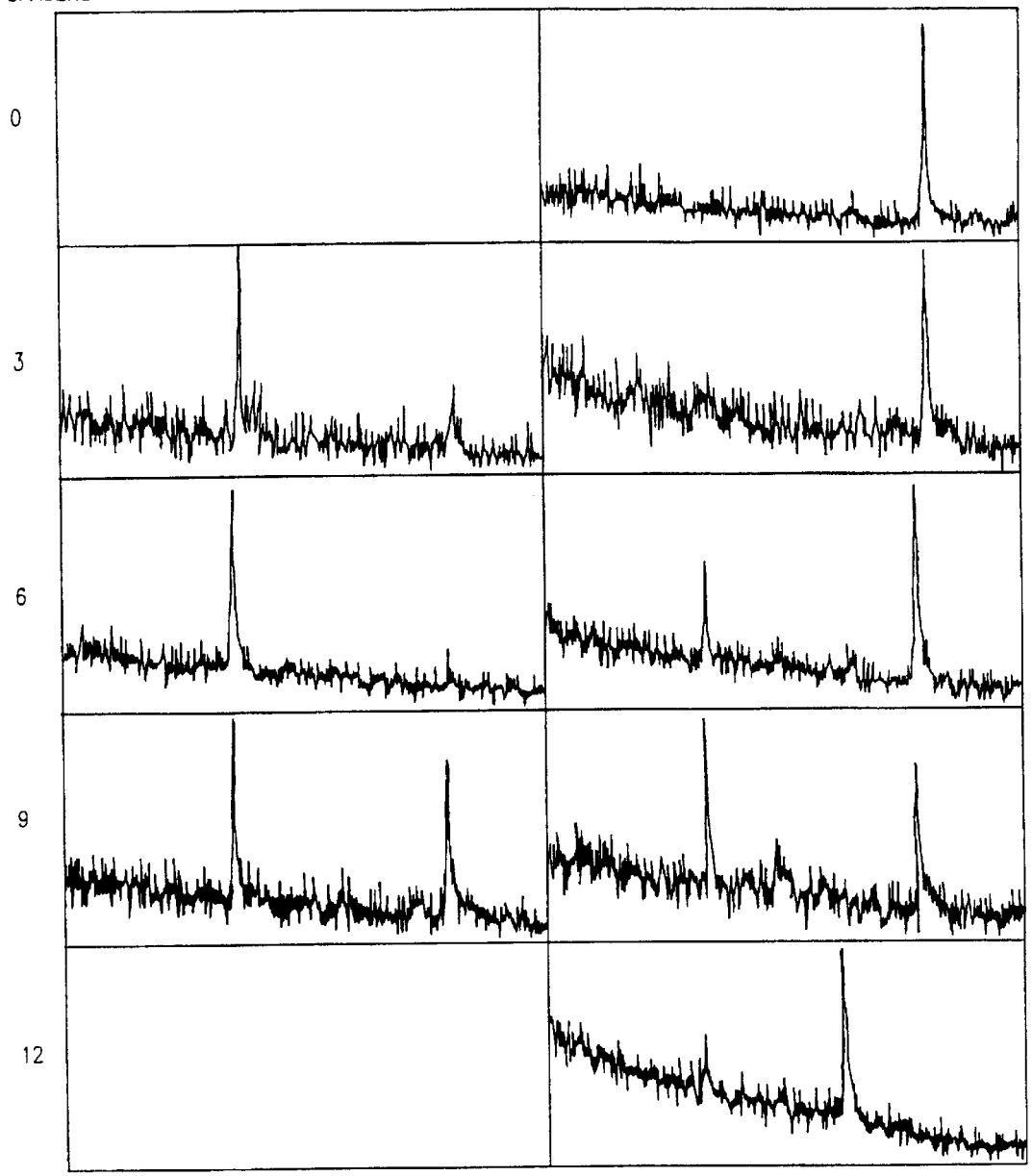
FIG. 20 is a representative MALDI-TOF mass spectrum of the specific extension products of the primer extension experiment illustrated in FIG. 19. The spectra in the left-hand column are those resulting from MALDI-TOF MS analysis of the extension reactions in which Sequenase was used. The spectra in the right-hand column are those resulting from analysis of the extension reactions in which ThermoSequenase was used. ThermoSequenase DNA polymerase was able to extend the 3'-end of the hybridized DNA primer where the distance between the DNA duplex and the surface of the derivatized silicon wafer varied between 0 to 12 nucleotides. Sequenase DNA polymerase also was able to extend the hybridized DNA where the distance between the DNA duplex and the silicon wafer was between 3 and 9 nucleotides.

As previously shown in FIG. 18, a 3-base specific extension of the bound 12-mer oligonucleotide was observed using the oligomer primer where there is a 9-base spacer between the duplex and the surface [SEQ ID NO: 12]. As shown in FIG. 19, similar results were observed when the DNA spacer lengths between the SIAB moiety and the DNA duplex were 0, 3, 6 and 12. The results of MALDI-TOF mass spectrometry analysis of the wafers are shown in FIG. 20. In addition, FIG. 19 also shows that the extension reaction may be performed using a variety of DNA polymerases. Thus, the SIAB linker may be directly coupled to the DNA template or may include a linker sequence without effecting primer extension of the hybridized DNA.

EXAMPLE 8

Detection of Double-Stranded Nucleic Acid Molecules Via Strand Displacement and Hybridization to an Immobilized Complementary Nucleic Acid This example describes immobilization of a 24-mer primer and the specific hybridization of one strand of a duplex DNA molecule, thereby permitting amplification of a selected target molecule in solution phase and permitting detection of the double stranded molecule.

A 24-mer DNA primer CTGATGCGTC GGATCATCTT TTTT [SEQ ID NO: 8], containing a 3'-free thiol group was coupled to a SIAB-derivatized silicon wafer essentially as outlined in FIG. 7 and described in Examples 1 and 2.

An 18-mer synthetic oligonucleotide 5'-CTGATGCGTCGGATCATC-3' [SEQ ID NO: 16] was premixed with a 12-mer oligonucleotide 5'-GATGATCCGACG-3' [SEQ ID NO: 12] that has a sequence that is complementary to 12 base portion of the 18-mer oligonucleotide. The oligonucleotide mix was heated to 75° C. and cooled slowly to room temperature to facilitate the formation of a duplex molecule: 5'-CTGATGCGTCGGATCATC-3' [SEQ ID NO: 16] 3'-GCAGCCTAGTAG-5' [SEQ ID NO: 12].

The specific hybridization of the 12-mer strand of the duplex molecule to the immobilized 24-mer primer was carried out by mixing 1 μM of the duplex molecule using the hybridization conditions described in Example 6.

The wafers were analyzed by mass spectrometry as described above. Specific hybridization was detected in a mass spectrum of the 12-mer with a mass-to-charge ratio of 3682.78 Da.

EXAMPLE 9

1-(2-Nitro-5-(3-O-4,4'-dimethoxytritylpropoxy) phenyl)-1-O-((2-cyanoethoxy)-diisopropylaminophosphino)ethane A. 2-Nitro-5-(3-hydroxypropoxy)benzaldehyde 3-Bromo-1-propanol (3.34 g, 24 mmol) was refluxed in 80 ml of anhydrous acetonitrile with 5-hydroxy-2-nitrobenzaldehyde (3.34 g, 20 mmol), $K_2CO_3$ (3.5 g), and Kl (100 mg) overnight (15 h). The reaction mixture was cooled to room temperature and 150 ml of methylene chloride was added. The mixture was filtered and the solid residue was washed with methylene chloride. The combined organic solution was evaporated to dryness and redissolved in 100 ml methylene chloride. The resulted solution was washed with saturated NaCl solution and dried over sodium sulfate. 4.31 g (96%) of desired product was obtained after removal of the solvent in vacuo.

$R_f$=0.33 (dichloromethane/methanol, 95/5).

UV (methanol) maximum: 313, 240 (shoulder), 215 nm; minimum: 266 nm.

$^1$H NMR (DMSO-$d_6$) δ 10.28 (s, 1H), 8.17 (d, 1H), 7.35 (d, 1H), 7.22 (s, 1H), 4.22(t, 2H), 3.54 (t, 2H), 1.90 (m, 2H).

$^{13}$C NMR (DMSO-$d_6$) δ 189.9, 153.0, 141.6, 134.3, 127.3, 118.4, 114.0, 66.2, 56.9, 31.7.

B. 2-Nitro-5-(3-O-t-butyidimethylsilylpropoxy)benzaldehyde

2-Nitro-5-(3-hydroxypropoxy)benzaldehyde(1 g, 4.44 mmol) was dissolved in 50 ml anhydrous acetonitrile. To this solution, it was added 1 ml of triethylamine, 200 mg of imidazole, and 0.8 g (5.3 mmol) of tBDMSCI. The mixture was stirred at room temperature for 4 h. Methanol (1 ml) was added to stop the reaction. The solvent was removed in vacuo and the solid residue was redissolved in 100 ml methylene chloride. The resulted solution was washed with saturated sodium bicarbonate solution and then water. The organic phase was dried over sodium sulfate and the solvent was removed in vacuo. The crude mixture was subjected to a quick silica gel column with methylene chloride to yield 1.44 g (96%) of 2-nitro-5-(3-O-t-butyidimethylsilylpropoxy)benzaldehyde.

$R_f$=0.67 (hexane/ethyl acetate, 5/1).

UV (methanol), maximum: 317, 243, 215 nm; minimum: 235, 267 nm.

$^1$H NMR (DMSO-$d_6$) δ 10.28 (s, 1H), 8.14 (d, 1H), 7.32 (d, 1H), 7.20 (s, 1H), 4.20 (t, 2H), 3.75 (t, 2H), 1.90 (m, 2H), 0.85 (s, 9H), 0.02 (s, 6H).

$^{13}$C NMR (DMSO-$d_6$) δ 189.6, 162.7, 141.5, 134.0, 127.1, 118.2, 113.8, 65.4, 58.5, 31.2, 25.5, −3.1, −5.7.

C. 1-(2-Nitro-5-(3-O-t-butyidimethylsilylpropoxy)phenyl)ethanol

High vacuum dried 2-nitro-5-(3-O-t-butyidimethylsilylpropoxy)benzaldehyde (1.02 g, 3 mmol) was dissolved 50 ml of anhydrous methylene chloride. 2 M Trimethylaluminium in toluene (3 ml) was added dropwise within 10 min and the reaction mixture was kept at room temperature. It was stirred further for 10 min and the mixture was poured into 10 ml ice cooled water. The emulsion was separated from water phase and dried over 100 g of sodium sulfate to remove the remaining water. The solvent was removed in vacuo and the mixture was applied to a silica gel column with gradient methanol in methylene chloride. 0.94 g (86%) of desired product was isolated.

$R_f$=0.375 (hexane/ethyl acetate, 5/1).

UV (methanol), maximum: 306, 233, 206 nm; minimum: 255, 220 nm.

$^1$H NMR (DMSO-$d_6$) δ 8.00 (d, $_1$H), 7.36 (s, 1H), 7.00 (d, 1H), 5.49 (b, OH), 5.31 (q, 1H), 4.19 (m, 2H), 3.77 (t, 2H), 1.95 (m, 2H), 1.37 (d, 3H), 0.86 (s, 9H), 0.04 (s, 6H).

$^{13}$C NMR (DMSO-$d_6$) δ 162.6, 146.2, 139.6, 126.9, 112.9, 112.5, 64.8, 63.9, 58.7, 31.5, 25.6, 24.9, −3.4, −5.8.

D. 1-(2-Nitro-5-(3-hydroxypropoxy)phenyl)ethanol 1-(2-Nitro-5-(3-O-t-butyldimethylsilylpropoxy)phenyl)ethanol (0.89 g, 2.5 mmol) was dissolved in 30 ml of THF and 0.5 mmol of nBU$_4$NF was added under stirring. The mixture was stirred at room temperature for 5 h and the solvent was removed in vacuo. The remaining residue was applied to a silica gel column with gradient methanol in methylene chloride. 1-(2-Nitro-5-(3-hydroxypropoxy)phenyl)ethanol (0.6 g (99%) was obtained.

$R_f$=0.17 (dichloromethane/methanol, 95/5).

UV (methanol), maximum: 304, 232, 210 nm; minimum: 255, 219 nm.

$^1$H NMR (DMSO-$d_6$) δ 8.00 (d, 1H), 7.33 (s, 1H), 7.00 (d, 1H), 5.50 (d, OH), 5.28 (t, OH), 4.59 (t, 1H), 4.17 (t, 2H), 3.57 (m, 2H), 1.89 (m, 2H), 1.36 (d, 2H).

$^{13}$C NMR (DMOS-$d_6$) δ 162.8, 146.3, 139.7, 127.1, 113.1, 112.6, 65.5, 64.0, 57.0, 31.8, 25.0.

E. 1-(2-Nitro-5-(3-O-4,4'-dimethoxytritylpropoxy)phenyl)ethanol 1-(2-Nitro-5-(3-hydroxypropoxy)phenyl)ethanol (0.482 g, 2 mmol) was co-evaporated with anhydrous pyridine twice and dissolved in 20 ml anhydrous pyridine. The solution was cooled in ice-water bath and 750 mg (2.2 mmol) of DMTCI was added. The reaction mixture was stirred at room temperature overnight and 0.5 ml methanol was added to stop the reaction. The solvent was removed in vacuo and the residue was co-evaporated with toluene twice to remove trace of pyridine. The final residue was applied to a silica gel column with gradient methanol in methylene chloride containing drops of triethylamine to yield 0.96 g (89%) of the desired product 1-(2-nitro-5-(3-O-4,4'-dimethoxytrityl-propoxy)phenyl)ethanol.

$R_f$=0.50 (dichloromethane/methanol, 99/1).

UV (methanol), maximum: 350 (shoulder), 305, 283, 276 (shoulder), 233, 208 nm; minimum: 290, 258, 220 nm.

$^1$H NMR (DMSO-$d_6$) δ 8.00 (d, 1H), 6.82–7.42 (ArH), 5.52 (d, OH), 5.32 (m, 1H), 4.23 (t, 2H), 3.71 (s, 6H), 3.17 (t, 2H), 2.00 (m, 2H), 1.37 (d, 3H).

$^{13}$C NMR (DMOS-$d_6$) δ 162.5, 157.9, 157.7, 146.1, 144.9, 140.1, 139.7, 135.7, 129.5, 128.8, 127.6, 127.5, 127.3, 126.9, 126.4, 113.0, 112.8, 112.6, 85.2, 65.3, 63.9, 59.0, 54.8, 28.9, 24.9.

F. 1-(2-Nitro-5-(3-O-4,4'-dimethoxytritylpropoxy)phenyl)-1-O-((2-cyanoethoxy)-diisopropylaminophosphino)ethane 1-(2-Nitro-5-(3-O-4,4'-dimethoxytritylpropoxy)phenyl) ethanol (400 mg, 0.74 mmol) was dried under high vacuum and was dissolved in 20 ml of anhydrous methylene chloride. To this solution, it was added 0.5 ml N,N-diisopropylethylamine and 0.3 ml (1.34 mmol) of 2-cyanoethyl-N,N-diisopropylchlorophosphoramidite. The reaction mixture was stirred at room temperature for 30 min and 0.5 ml of methanol was added to stop the reaction. The mixture was washed with saturated sodium bicarbonate solution and was dried over sodium sulfate. The solvent was removed in vacuo and a quick silica gel column with 1% methanol in methylene chloride containing drops of triethylamine yield 510 mg (93%) the desired phosphoramidite.

$R_f$=0.87 (dichloromethane/methanol, 99/1).

EXAMPLE 10

1-(4-(3-O-4,4'-Dimethoxytritylpropoxy)-3-methoxy-6-nitrophenyl)-1-O-((2-cyanoethoxy)-diisopropylaminophosphino)ethane A. 4-(3-Hydroxypropoxy)-3-methoxyacetophenone 3-Bromo-1-propanol (53 ml, 33 mmol) was refluxed in 100 ml of anhydrous acetonitrile with 4-hydroxy-3-methoxyacetophenone (5 g, 30 mmol), $K_2CO_3$ (5 g), and KI (300 mg) overnight (15 h). Methylenechloride (150 ml) was added to the reaction mixture after cooling to room temperature. The mixture was filtered and the solid residue was washed with methylene chloride. The combined organic solution was evaporated to dryness and redissolved in 100 ml methylene chloride. The resulted solution was washed with saturated NaCl solution and dried over sodium sulfate. 6.5 g (96.4%) of desired product was obtained after removal of the solvent in vacuo.

$R_f$=0.41 (dichloromethane/methanol, 95/5).

UV (methanol), maximum: 304, 273, 227, 210 nm: minimum: 291, 244, 214 nm.

$^1$H NMR (DMSO-$d_6$) δ 7.64 (d, 1H), 7.46 (s, 1H), 7.04 (d, 1H), 4.58 (b, OH), 4.12 (t, 2H), 3.80 (s, 3H), 3.56 (t, 2H), 2.54 (s, 3H), 1.88 (m, 2H).

$^{13}$C NMR (DMSO-$d_6$) δ 196.3, 152.5, 148.6, 129.7, 123.1, 111.5, 110.3, 65.4, 57.2, 55.5, 31.9, 26.3.

B. 4-(3-Acetoxypropoxy)-3-methoxyacetophenone 4-(3-Hydroxypropoxy)-3-methoxyacetophenone (3.5 g, 15.6 mmol) was dried and dissolved in 80 ml anhydrous acetonitrile. This mixture, 6 ml of triethylamine and 6 ml of acetic anhydride were added. After 4 h, 6 ml methanol was added and the solvent was removed in vacuo. The residue was dissolved in 100 ml dichloromethane and the solution was washed with dilute sodium bicarbonate solution, then water. The organic phase was dried over sodium sulfate and the solvent was removed. The solid residue was applied to a silica gel column with methylene chloride to yield 4.1 g of 4-(3-acetoxypropoxy)-3-methoxyacetophenone (98.6%).

$R_f$=0.22 (dichloromethane/methanol, 99/1).

UV (methanol), maximum: 303, 273, 227, 210 nm; minimum: 290, 243, 214 nm.

$^1$H NMR (DMSO-$d_6$) δ 7.62 (d, 1H), 7.45 (s, 1H), 7.08 (d, 1H), 4.12 (m, 4H, 3.82 (s, 3H), 2.54 (s, 3H), 2.04 (m, 2H), 2.00 (s, 3H).

$^{13}$C NMR (DMSO-$d_6$) δ 196.3, 170.4, 152.2, 148.6, 130.0, 123.0, 111.8, 110.4, 65.2, 60.8, 55.5, 27.9, 26.3, 20.7.

C. 4-(3-Acetoxypropoxy)-3-methoxy-6-nitroacetophenone 4-(3-Acetoxypropoxy)-3-methoxyacetophenone (3.99 g, 15 mmol) was added portionwise to 15 ml of 70% $HNO_3$ in water bath and keep the reaction temperature at the room temperature. The reaction mixture was stirred at room temperature for 30 min and 30 g of crushed ice was added. This mixture was extracted with 100 ml of dichloromethane and the organic phase was washed with saturated sodium bicarbonate solution. The solution was dried over sodium sulfate and the solvent was removed in vacuo. The crude mixture was applied to a silica gel column with gradient methanol in methylene chloride to yield 3.8 g (81.5%) of desired product 4-(3-acetoxypropoxy)-3-methoxy-6-nitroacetophenone and 0.38 g (8%) of ipso-substituted product 5-(3-acetoxypropoxy)-4-methoxy-1,2-dinitrobenzene. Side ipso-substituted product 5-(3-acetoxypropoxy)-4-methoxy-1,2-dinitrobenzene:

$R_f$=0.47 (dichloromethane/methanol, 99/1).

UV (methanol), maximum: 334, 330, 270, 240, 212 nm; minimum: 310, 282, 263, 223 nm.

$^1$H NMR (CDCl$_3$) δ 7.36 (s, 1H), 7.34 (s, 1H), 4.28 (t, 2H), 4.18 (t, 2H), 4.02 (s, 3H), 2.20 (m, 2H), 2.08 (s, 3H).

$^{13}$C NMR (CDCl$^3$) δ 170.9, 152.2, 151.1, 117.6, 111.2, 107.9, 107.1, 66.7, 60.6, 56.9, 28.2, 20.9.

Desired product 4-(3-acetoxypropoxy)-3-methoxy-6-nitroacetophenone:

$R_f$=0.29 (dichloromethane/methanol, 99/1).

UV (methanol), maximum: 344, 300, 246, 213 nm; minimum: 320, 270, 227 nm.

$^1$H NMR (CDCl$_3$) δ 7.62 (s, 1H), 6.74 (s, 1H), 4.28 (t, 2H), 4.20 (t, 2H), 3.96 (s, 3H), 2.48 (s, 3H), 2.20 (m, 2H), 2.08 (s, 3H).

$^{13}$C NMR (CDCl$_3$) δ 200.0, 171.0, 154.3, 148.8, 138.3, 133.0, 108.8, 108.0, 66.1, 60.8, 56.6, 30.4, 28.2, 20.9.

D. 1-(4-(3-Hydroxypropoxy)-3-methoxy-6-nitrophenyl)ethanol 4-(3-Acetoxypropoxy)-3-methoxy-6-nitroacetophenone (3.73 g, 12 mmol) was added 150 ml ethanol and 6.5 g of $K_2CO_3$. The mixture was stirred at room temperature for 4 h and TLC with 5% methanol in dichloromethane indicated the completion of the reaction. To this same reaction mixture, it was added 3.5 g of NaBH$_4$ and the mixture was stirred at room temperature for 2 h. Acetone (10 ml) was added to react with the remaining NaBH$_4$. The solvent was removed in vacuo and the residue was uptaken into 50 g of silica gel. The silica gel mixture was applied on the top of a silica gel column with 5% methanol in methylene chloride to yield 3.15 g (97%) of desired product 1-(4-(3-hydroxypropoxy)-3-methoxy-6-nitrophenyl) ethanol. Intermediate product 4-(3-hydroxypropoxy)-3-methoxy-6-nitroacetophenone after deprotection:

$R_f$=0.60 (dichloromethane/methanol, 95/5).

Final product 1-(4-(3-hydroxypropoxy)-3-methoxy-6-nitrophenyl)ethanol:

$R_f$=0.50 (dichloromethane/methanol, 95/5).

UV (methanol), maximum: 344, 300, 243, 219 nm: minimum: 317, 264, 233 nm.

$^1$H NMR (DMSO-$d_6$) δ 7.54 (s, 1H), 7.36 (s, 1H), 5.47 (d, OH), 5.27 (m, 1H), 4.55 (t, OH), 4.05 (t, 2H), 3.90 (s, 3H), 3.55 (q, 2H), 1.88 (m, 2H), 1.37 (d, 3H).

$^{13}$C NMR (DMSO-$d_6$) δ 153.4, 146.4, 138.8, 137.9, 109.0, 108.1, 68.5, 65.9, 57.2, 56.0, 31.9, 29.6.

E. 1-(4-(3-O-4,4'-Dimethoxytritylpropoxy)-3-methoxy-6-nitrophenyl)ethanol 1-(4-(3-Hydroxypropoxy)-3-methoxy-6-nitrophenyl) ethanol (0.325 g, 1.2 mmol) was co-evaporated with anhydrous pyridine twice and dissolved in 15 ml anhydrous pyridine. The solution was cooled in ice-water bath and 450 mg (1.33 mmol) of DMTCl was added. The reaction mixture was stirred at room temperature overnight and 0.5 ml methanol was added to stop the reaction. The solvent was removed in vacuo and the residue was co-evaporated with toluene twice to remove trace of pyridine. The final residue was applied to a silica gel column with gradient methanol in methylene chloride containing drops of triethylamine to yield 605 mg (88%) of desired product 1-(4-(3-O-4,4'-dimethoxytritylpropoxy)-3-methoxy-6-nitrophenyl)ethanol.

$R_f$=0.50 (dichloromethane/methanol, 95/5).

UV (methanol), maximum: 354, 302, 282, 274, 233, 209 nm; minimum: 322, 292, 263, 222 nm.

$^1$H NMR (DMSO-$d_6$) δ 7.54 (s, 1H), 6.8–7.4 (ArH), 5.48 (d, OH), 5.27 (m, 1H), 4.16 (t, 2H), 3.85 (s, 3H), 3.72 (s, 6H), 3.15 (t, 2H), 1.98 (t, 2H), 1.37 (d, 3H).

$^{13}$C NMR (DMSO-$d_6$) δ 157.8, 153.3, 146.1, 144.9, 138.7, 137.8, 135.7, 129.4, 128.7, 127.5, 127.4, 126.3, 112.9, 112.6, 108.9, 108.2, 85.1, 65.7, 63.7, 59.2, 55.8, 54.8, 29.0, 25.0.

F. 1-(4-(3-O-4,4'-Dimethoxytritylpropoxy)-3-methoxy-6-nitrophenyl)-1-O-((2-cyanoethoxy)-diisopropylaminophosphino)ethane 1-(4-(3-O-4,4'-Dimethoxytritylpropoxy)-3-methoxy-6-nitrophenyl)ethanol (200 mg, 3.5 mmol) was dried under high vacuum and was dissolved in 15 ml of anhydrous methylene chloride. To this solution, it was added 0.5 ml N,N-diisopropylethylamine and 0.2 ml (0.89 mmol) of 2-cyaiioethyl-N,N-diisopropylchlorophosphoramidite. The reaction mixture was stirred at room temperature for 30 min and 0.5 ml of methanol was added to stop the reaction. The mixture was washed with saturated sodium bicarbonate solution and was dried over sodium sulfate. The solvent was removed in vacuo and a quick silica gel column with 1% methanol in methylene chloride containing drops of triethylamine yield 247 mg (91.3%) the desired phosphoramidite 1-(4-(3-O-4,4'-dimethoxytritylpropoxy)-3-methoxy-6-nitrophenyl)-1-O-((2-cyanoethoxy)-diisopropylaminophosphino)ethane.

$R_f$=0.87 (dichloromethane/methanol, 99/1).

EXAMPLE 11

Oligonucleotide Synthesis

The oligonucleotide conjugates containing photocleavable linker were prepared by solid phase nucleic acid synthesis (see: Sinha et al. *Tetrahedron Lett.* 1983, 24, 5843–5846; Sinha et al. *Nucleic Acids Res.* 1984, 12, 4539–4557; Beaucage et al. *Tetrahedron* 1993, 49, 6123–6194; and Matteucci et al. *J. Am. Chem. Soc.* 1981, 103, 3185–3191) under standard conditions. In addition a longer coupling time period was employed for the incorporation of photocleavable unit and the 5' terminal amino group. The coupling efficiency was detected by measuring the absorbance of released DMT cation and the results indicated a comparable coupling efficiency of phosphoramidite 1-(2-nitro-5-(3-O-4,4'-dimethoxytritylpropoxy)phenyl)-1-O-((2-cyanoethoxy)-diisopropylaminophosphino)ethane or 1-(4-(3-O-4,4'-dimethoxytritylpropoxy)-3-methoxy-6-nitrophenyl)-1-O-((2-cyanoethoxy)-diisopropylaminophosphino)ethane with those of common nucleoside phosphoramodites. Deprotection of the base protection and release of the conjugates from the solid support was carried out with concentrated ammonium at 55° C. overnight. Deprotection of the base protection of other conjugates was done by fast deprotection with AMA reagents. Purification of the MMT-on conjugates was done by HPLC (trityl-on) using 0.1 M triethylammonium acetate, pH 7.0 and a gradient of acetonitrile (5% to 25% in 20 minutes). The collected MMT or DMT protected conjugate was reduced in volume, detritylated with 80% aqueous acetic acid (40 min, 0° C.), desalted, stored at −20° C.

EXAMPLE 12

Photolysis Study

In a typical case, 2 nmol of oligonucleotide conjugate containing photocleavable linker in 200 µl distilled water was irradiated with a long wavelength UV lamp (Blak Ray XX-15 UV lamp, Ultraviolet products, San Gabriel, Calif.) at a distance of 10 cm (emission peak 365 nm, lamp intensity=1.1 mW/cm$^2$ at a distance of 31 cm). The resulting mixture was analyzed by HPLC (trityl-off) using 0.1 M triethylammonium acetate, pH 7.0 and a gradient of acetonitrile. Analysis showed that the conjugate was cleaved from the linder within minutes upon UV irradiation.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for synthesizing DNA on the surface of a support, comprising:

reacting the surface of a silicon support or a support with a silicon surface with a solution of 3-aminopropyltriethoxysilane to produce a uniform layer of primary amines on the surface of the support;

derivatizing the surface of the support with iodoacetamido functionalities by reacting the uniform layer of primary amines with a solution of. N-succinimidyl (4-iodoacetyl) aminobenzoate (SIAB);

contacting the surface of the support with a thiol-containing strand of DNA, whereby the thiol-containing DNA is immobilized on the surface of the support by a covalent bond between the thiol group of the thiol-containing DNA and the iodoacetamrido functionality on the surface;

hybridizing a single-strand of DNA that is complementary to a portion of the immobilized thiol-containing DNA; and adding at least one nucleotide to the 3'-end of the hybridized single-strand of DNA by DNA synthesis, whereby DNA is synthesized on the surface of a support; and determining a molecular weight by mass spectrometry of the single-strand of DNA to which at least one nucleotide has been added.

2. The method of claim 1, wherein the immobilized DNA is positioned on the support in the form of an array.

3. The method of claim 1, further comprising: adding one or more dideoxynucleoside triphosphates during DNA synthesis.

4. The method of claim 1, wherein the mass spectrometry analysis is selected from the group consisting of Matrix Assisted Laser Desorption/Ionization, Time-of-Flight (MALDI-TOF) analysis, Electronspray Electrospray (ES), Ion Cyclotron Resonance (ICR) and Fourier transform.

5. A method, comprising:

reacting thiol-containing DNA molecules with a solid support under conditions such that a covalent bond is formed, thereby immobilizing DNA molecules on the insoluble support, wherein:

the resulting covalent linkages and support are stable to laser desorption, and the support is a silicon support or comprises a silicon surface or a silicon dioxide surface;

hybridizing a single-strand of DNA to a portion of the immobilized thiol-containing DNA molecule complementary thereto;

adding at least one deoxynucleotide or dideoxynucleotide to the 3'-end of the hybridized single strand of DNA by enzymatic DNA synthesis; and determining the molecular weight of the hybridized single-strand of DNA to which at least one deoxynucleotide or dideoxynucleotide has been added using mass spectrometry analysis, whereby the sequence of at least a portion of thiol-containing DNA molecule immobilized on the surface of a support is determined.

6. A method for sequencing DNA, comprising:

reacting the surface of a silicon support or support with a silicon surface with a solution of 3-aminopropyltriethoxysilane to produce a uniform layer of primary amines on the surface of the support, derivatizing the surface of the support with iodoacetamido functionalities by reacting the uniform layer of primary amines with a solution of N-succinimidyl (4-iodoacetyl) aminobenzoate (SIAB), reacting the surface of the support with a thiol-containing strand of DNA, whereby the thiol-containing DNA is immobilized on the surface of the support by a covalent bond between the thiol group of the thiol-containing DNA and the iodoacetamido functionality derivatized on the surface of the support, hybridizing a single-strand of DNA to a portion of the immobilized thiol-containing DNA complementary thereto, performing DNA synthesis in the presence of an appropriate mixture of deoxynucleotides containing one or more dideoxynucleotides, wherein at least one deoxynucleotide or dideoxynucleotide is added to the hybridized single-strand of DNA at its 3'-end by enzymatic DNA synthesis; and determining the molecular weight of the hybridized single-strand of DNA containing the enzymatically added deoxynucleotide(s) or dideoxynucleotide(s) using mass spectrometry analysis, whereby at least one base in the sequence is determined.

7. The method of claim 5 or 6, wherein the mass spectrometry analysis is selected from the group consisting of Matrix Assisted Laser Desorption/Ionization, Time-of-Flight (MALDI-TOF) analysis, Electrospray (ES), Ion Cyclotron Resonance (ICR) and Fourier transform.

8. The method of claim 5, or 6 wherein the immobilized DNA is positioned on the support in the form of an array.

* * * * *

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 1:

GAATTCGAGC TCGGTACCCG G                21

-continued (2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 2:

CCGGGTACCG AGCTCGAATT C                                           21

(2) INFORMATION FOR SEQ ID NO: 3:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 3:

CCTCTTGGGA ACTGTGTAGT ATT                                         23

(2) INFORMATION FOR SEQ ID NO: 4:

(i) SEQUENCE CHARACTERISTICS:
        (A) LENGTH: 112 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 4:

AGGCTGTCTC TCTCCCTCTC TCATACACAC ACACACACAC ACACACACAC ACACACACAC    60

ACACACACAC TCACACTCAC CCACANNNAA ATACTACACA GTTCCCAAGA GG          112

(2) INFORMATION FOR SEQ ID NO: 5:

(i) SEQUENCE CHARACTERISTICS:
        (A) LENGTH: 49 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 5:

TAATACGACT CACTATAGGG CGAAGGCTGT CTCTCTCCCT CTCTCATAC                49

(2) INFORMATION FOR SEQ ID NO: 6:

(i) SEQUENCE CHARACTERISTICS:
             (A) LENGTH: 135 base pairs
             (B) TYPE: nucleic acid
             (C) STRANDEDNESS: single
             (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 6:

TAATACGACT CACTATAGGG CGAAGGCTGT CTCTCTCCCT CTCTCATACA CACACACACA      60

CACACACACA CACACACACA CACACACACA CACTCACACT CACCCACANN NAAATACTAC     120

ACAGTTCCCA AGAGG                                                     135

(2) INFORMATION FOR SEQ ID NO: 7:

(i) SEQUENCE CHARACTERISTICS:
             (A) LENGTH: 12 base pairs
             (B) TYPE: nucleic acid
             (C) STRANDEDNESS: single
             (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 7:

AATACTACAC AG                                                         12

(2) INFORMATION FOR SEQ ID NO: 8:

(i) SEQUENCE CHARACTERISTICS:
             (A) LENGTH: 24 base pairs
             (B) TYPE: nucleic acid
             (C) STRANDEDNESS: unknown
             (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 8:

CTGATGCGTC GGATCATCTT TTTT                                          24

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 9:

GATGATCCGA CGCATCAGAA TGT                                           23

(2) INFORMATION FOR SEQ ID NO: 10:

(i) SEQUENCE CHARACTERISTICS:
        (A) LENGTH: 29 base pairs
        (B) TYPE: nucleic acid
        (C) STRANDEDNESS: unknown
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 10:

GATCTAGCTG GGCCGAGCTA GGCCGTTGA                                     29

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

CTGATGCGTC GGATCATCTT TTTTTTT                                       27

(2) INFORMATION FOR SEQ ID NO: 12:

```
        (i) SEQUENCE CHARACTERISTICS:
            (A) LENGTH: 12 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

GATGATCCGA CG                                                              12

(2) INFORMATION FOR SEQ ID NO: 13:

(i) SEQUENCE CHARACTERISTICS:
            (A) LENGTH: 15 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

GATGATCCGA CGCAT                                                           15

(2) INFORMATION FOR SEQ ID NO: 14:

(i) SEQUENCE CHARACTERISTICS:
            (A) LENGTH: 12 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

AAAAAAGATG AT                                                              12

(2) INFORMATION FOR SEQ ID NO: 15:

(i) SEQUENCE CHARACTERISTICS:
            (A) LENGTH: 12 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO
```

-continued (iv) ANTI-SENSE: NO (v) FRAGMENT TYPE: <Unknown>

(vi) ORIGINAL SOURCE:

(xi) SEQUENCE DESCRIPTION: SEQ ID NO: 15:

GATCCGACGC AT                                                    12

(2) INFORMATION FOR SEQ ID NO: 16:

(i) SEQUENCE CHARACTERISTICS:
            (A) LENGTH: 18 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

CTGATGCGTC GGATCATC                                              18

(2) INFORMATION FOR SEQ ID NO: 17:

(i) SEQUENCE CHARACTERISTICS:
            (A) LENGTH: 50 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

GCCTGGTACA CTGCCAGGCG CTTCTGCAGG TCATCGGCAT CGCGGAGGAG            50

(2) INFORMATION FOR SEQ ID NO: 18:

(i) SEQUENCE CHARACTERISTICS:
            (A) LENGTH: 50 base pairs
            (B) TYPE: nucleic acid
            (C) STRANDEDNESS: single
            (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

GCCTGGTACA CTGCCAGGCA CTTCTGCAGG TCATCGGCAT CGCGGAGGAG            50

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

GATGCCGATG ACCTGCAGAAG                                      21